(12) United States Patent
Schultheiss et al.

(10) Patent No.: US 11,708,583 B2
(45) Date of Patent: *Jul. 25, 2023

(54) FUNGAL RESISTANT PLANTS EXPRESSING RLK1

(71) Applicant: BASF PLANT SCIENCE COMPANY GMBH, Ludwigshafen (DE)

(72) Inventors: Holger Schultheiss, Limburgerhof (DE); Tobias Mentzel, Mannheim (DE)

(73) Assignee: BASF PLANT SCIENCE COMPANY GMBH, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 17/498,484

(22) Filed: Oct. 11, 2021

(65) Prior Publication Data

US 2022/0127636 A1    Apr. 28, 2022

Related U.S. Application Data

(63) Continuation of application No. 16/451,984, filed on Jun. 25, 2019, now Pat. No. 11,142,774, which is a continuation of application No. 14/419,510, filed as application No. PCT/IB2013/056112 on Jul. 25, 2013, now Pat. No. 10,329,580.

(60) Provisional application No. 61/681,161, filed on Aug. 9, 2012.

(30) Foreign Application Priority Data

Aug. 9, 2012  (EP) .................................... 12179859

(51) Int. Cl.
C12N 15/82    (2006.01)
C12N 9/12     (2006.01)

(52) U.S. Cl.
CPC ....... *C12N 15/8282* (2013.01); *C12N 9/1205* (2013.01); *C12Y 207/01037* (2013.01); *C12Y 207/11* (2013.01)

(58) Field of Classification Search
None
See application file for complete search history.

(56) References Cited

U.S. PATENT DOCUMENTS

| | | | |
|---|---|---|---|
| 7,968,765 B2 | 6/2011 | Frankard et al. | |
| 10,329,580 B2 | 6/2019 | Schultheiss et al. | |
| 11,142,774 B2 | 10/2021 | Schultheiss et al. | |
| 2004/0034888 A1 | 2/2004 | Liu et al. | |
| 2008/0057093 A1 | 3/2008 | Wan et al. | |
| 2012/0216314 A1 | 8/2012 | Kondo et al. | |
| 2017/0037426 A1 | 2/2017 | Alexandrov et al. | |

FOREIGN PATENT DOCUMENTS

| | | |
|---|---|---|
| CN | 101023176 A | 8/2007 |
| CN | 102575262 A | 7/2012 |
| WO | WO-00/4761 A1 | 2/2000 |
| WO | WO-02/10210 A2 | 2/2002 |
| WO | WO-02/46439 A2 | 6/2002 |
| WO | WO 2009/091518 * | 7/2009 |
| WO | WO-2009/091518 A2 | 7/2009 |
| WO | WO-2010/037714 A1 | 4/2010 |
| WO | WO-2012/023099 A1 | 2/2012 |
| WO | WO-2012/023111 A1 | 2/2012 |
| WO | WO-2012/172498 A1 | 12/2012 |
| WO | WO-2013/001435 A1 | 1/2013 |
| WO | WO-2013/092275 A2 | 6/2013 |
| WO | WO-2013/093738 A1 | 6/2013 |
| WO | WO-2013/149801 A1 | 10/2013 |
| WO | WO-2013/149804 A1 | 10/2013 |
| WO | WO-2013/152917 A1 | 10/2013 |
| WO | WO-2014/024079 A2 | 2/2014 |
| WO | WO-2014/024090 A2 | 2/2014 |
| WO | WO-2014/024102 A1 | 2/2014 |
| WO | WO-2014/041444 A1 | 3/2014 |
| WO | WO-2014/076614 A1 | 5/2014 |
| WO | WO-2014/117988 A1 | 8/2014 |
| WO | WO-2014/117990 A1 | 8/2014 |
| WO | WO-2014/118018 A1 | 8/2014 |

OTHER PUBLICATIONS

GenBank Accession No. BAC42100, Putative receptor kinase [*Arabidopsis thaliana*], dated Feb. 14, 2004.
GenBank Accession No. BAC42570, Putative receptor protein kinase [*Arabidopsis thaliana*], dated Feb. 14, 2004.
GenBank Accession No. NP_176532, Putative LRR receptor-like serine/threonine-protein kinase [*Arabidopsis thaliana*], dated May 28, 2011.
Guo et al., Protein tolerance to random amino acid change, Proc. Natl. Acad. Sci. USA, 101(25):9205-10 (Jun. 2004).
Heath, Cellular interactions between biotrophic fungal pathogens and host or nonhost plants, Can. J. Plant Pathol., 24:259-264 (2002).
International Search Report and Written Opinion for Application No. PCT/IB2013/056112 dated Feb. 6, 2014.
Morillo et al., Functional analysis of receptor-like kinases in monocots and dicots, Current Opinion in Plant Biology,9:460-469 (2006).
Neu et al., Cytological and molecular analysis of the Hordeum vulgare-Puccinia triticina nonhost interaction, MPMI, 16(7):626-633 (2003).

(Continued)

*Primary Examiner* — Anne Kubelik
(74) *Attorney, Agent, or Firm* — Marshall, Gerstein & Borun LLP

(57) ABSTRACT

The present invention relates to a method of increasing resistance against fungal pathogens of the order Pucciniales, preferably the family Phacopsoraceae, in plants and/or plant cells. This is achieved by increasing the expression of an RLK1protein or fragment thereof in a plant, plant part and/or plant cell in comparison to wild type plants, wild type plant parts and/or wild type plant cells. Furthermore, the invention relates to transgenic plants, plant parts, and/or plant cells having an increased resistance against fungal pathogens, in particular, pathogens of the order Pucciniales, preferably the family Phacopsoraceae, and to recombinant expression vectors comprising a sequence that is identical or homologous to a sequence encoding an RLK1protein.

8 Claims, 11 Drawing Sheets

Specification includes a Sequence Listing.

(56) References Cited

OTHER PUBLICATIONS

Nurnberger et al., Trends in Plant Science, 11:519-522 (2006).
Office Action, European patent application No. 12 17 9859, dated Nov. 20, 2012.
Rytter et al., Additional alternative hosts of Phakopsora pachyrhizi, causal agent of soybean rust, Plant Dis., 87:818-819 (1984).
Sinclair et al., (eds.) Proceedings of the Soybean Rust Workshop, Aug. 9-11, 1995. Urbana, IL: National Soybean Research Laboratory, (1995).
UniProt Accession No. Q9FLL2, Leucine-rich repeat receptor-like protein kinase dated Mar. 1, 2001.
Yariv et al., The LysM receptor-like kinase LysM RLK1 is required to activate defense and abiotic-stress resposnes induced by overexpression of fungal chitinases in *Arabidopsis* plants, Molecular Plant, 5(5):1113-1124 (2012).
Zhang et al., Plant immunity triggered by microbial molecular signatures, Molecular Plant, 3(5):783-793 (2010).

* cited by examiner

Figure 3:

```
   1 ATGAGACTTT ACTTATCTTC AACGATGCAG CTTTCTCTTA TGAGTCTTGT
  51 TCTAGGGTTC CTCTTTGTTT CCTGTGACGC GTTTGCCTCT AAAGAAGTTG
 101 AAGCAGTTAG AAGATTCAAG GAAGCCATTT ATAAGGACCC ATTGCTAGTT
 151 ATGTCTAATT GGAATGTCCC CAATTTGAGT CCTTGTGATT GGAATGGCAT
 201 TAAATGTTCT CCATCTAAGG ATCACATTAT CAAGATAAAT ATATCGGGGA
 251 CATCGATGAG AGGGTTTCTT GTGCCAGAAC TTGGTCAAAT AACCTACTTG
 301 CAAGAACTGA TCCTGCGTGG GAACATTCTA ATGGGGACAA TACCAAAGGA
 351 GATAGGAAAG TTAAAGAAAC TCAAGATCTT AGACCTGGGA AACAATCATT
 401 TGACAGGACC GATTCCAGCA GAGATCGGGA AATTGTCAAG GATTAAGACA
 451 ATAAACCTTC AGTCCAATGG TTTAATAGGA AAGTTACCTC CAGAGATTGG
 501 AAACTTGAAG CACCTTAAAG AACTTCTTAT TGGCAGGAAT AGGCTTCGAG
 551 GAAGTATTCC TATTGCCGCG AAAACATCAA AAAAGTATGC TTCAAATCCA
 601 AGTGCAAACA TCAGTGGTTT GTGCAAGTCT TCTCTATTTA AAGTGGCAGA
 651 TTTCTCTTAC AACTTTTTCG AGGGAAGAGT TCCGAGTTGC TTGGATTACC
 701 TCCCAATAAC GAGCTTTCAA GGAAACTGCA TGAAAACCAT GGATGTTAAG
 751 CAGAGACCTC TTTCAGAATG TGCTCGCTTA GCTGTAACCG TGGCCAAGAA
 801 GAAGCATCGA GCATCGAGAC AAACATGGCT TCGGAATTTT GAGATAGTCA
 851 CGGGATCATC AGTTGGCTTG CTCTTTCTAG TCGTAATGTT CTCTGCATGT
 901 AGCTTGTGCA AAATAAAGCG CTCTCTCATC GTTCCCTGGA AGAAATCTGC
 951 AAGTGAAAAG GAGAAGTTCA CGGTCTACGT TGATTCTGAA ATGCTGAAGG
1001 ATGTTTCAAG ATATACAAGA CAAGAGCTAG AAGTAGCATG TGAAGACTTC
1051 AGCAACATCA TTGATTCTAG TGCAGAGAGT CAGATTTACA AAGGAACGAT
1101 CAAAGGCGGG ACTGAGATCG CGGTTATCTC TCTCTGCGTT AAAGAAGAAA
1151 ATTGGACTGG ATATCTTGAG CTTAATTTCC AGAGAGAGGT TGCGGCTTTG
1201 GCTAGATTAA ACCATGAGAA TGCGGGGAAA TTACTGGGAT ACTGTAAAGA
1251 GAGTACACCG TTCACAAGAA TGCTTGTGTT TGAGTATGCA TCAAACGGGA
1301 CACTATACGA CCATCTCCAC TATGCGGACG GGAGTTTAGT ATCGTGGGCA
1351 AAACGCATGA AAATTGTTAT AGGCATCGCA CGTGGTCTCA AGTACCTTCA
1401 TACTGAACTC CATCCTCCAT TTACAGTCTC TGAGTTGAGC TCAACTGCAG
1451 TGTATCTCAC TGAAGATTTT ACTCCCAAAC TGGTTGATTT CGAATGCTGG
1501 AAGATTATTC AGGTGAGATC AGAGAAGAAC CTGAAGAATA TCTGTAATGA
1551 AGGAGCAATA TGTGTACTTC CCAATGCAAT GGAACACCGA GATATGGATT
1601 TACAAGGGAA TATCTACTCA TTTGGCATAC TTTTGCTGGA AATTGTAAGC
1651 GGAAGACCTT CTTATTGCCA AGACAGAGGT TGCTTGGTTG AATGGGTAAG
1701 GGAGAAAAAC CTTGGTGCAC CAGATGTGAT GGCTAGCTTG GTGGATCCTG
1751 AGCTCAAGCA TTTCAAGCAA AAAGAACTTG AGGCAGTATG TGAAGTGGCA
1801 AGCCAATGTC TGAACTTGGA CCAGAATGAA AAAGACAAGG ATAAGCTTTC
1851 TTGTTCGATT CAAGCGCTTT GTGAGACACT AGAGAGTAGA ATCACTGTGT
1901 CCATTTCTGC AGAATTCAAA TCGTCTTCTC TGGCGTGGGC CGAGCTAGCG
1951 CTGGCCTCGC CTTCTAACGA AGACGACGAT GATAGGAGTA AATAA
```

Figure 4:

```
MRLYLSSTMQLSLMSLVLGFLFVSCDAFASKEVEAVRRFKEAIYKDPLLV  50
MSNWNVPNLSPCDWNGIKCSPSKDHIIKINISGTSMRGFLVPELGQITYL 100
QELILRGNILMGTIPKEIGKLKKLKILDLGNNHLTGPIPAEIGKLSRIKT 150
INLQSNGLIGKLPPEIGNLKHLKELLIGRNRLRGSIPIAAKTSKKYASNP 200
SANISGLCKSSLFKVADFSYNFFEGRVPSCLDYLPITSFQGNCMKTMDVK 250
QRPLSECARLAVTVAKKKHRASRQTWLRNFEIVTGSSVGLLFLVVMFSAC 300
SLCKIKRSLIVPWKKSASEKEKFTVYVDSEMLKDVSRYTRQELEVACEDF 350
SNIIDSSAESQIYKGTIKGGTEIAVISLCVKEENWTGYLELNFQREVAAL 400
ARLNHENAGKLLGYCKESTPFTRMLVFEYASNGTLYDHLHYADGSLVSWA 450
KRMKIVIGIARGLKYLHTELHPPFTVSELSSTAVYLTEDFTPKLVDFECW 500
KIIQVRSEKNLKNICNEGAICVLPNAMEHRDMDLQGNIYSFGILLLEIVS 550
GRPSYCQDRGCLVEWVREKNLGAPDVMASLVDPELKHFKQKELEAVCEVA 600
SQCLNLDQNEKDKDKLSCSIQALCETLESRITVSISAEFKSSSLAWAELA 650
LASPSNEDDDDRSK*
```

Figure 5:

```
   1 TTAAAATTTA TTGGAAACGT ATATATTTTG TTTTTATTTA ATGTAATAAT
  51 ATTTTGTCTT CTTTCACATT TTAAGCAGGT TATATATTGA CTATAAATGT
 101 TTCACAGATA GATGCATGTT GATACATTTT TCCTTGTATA CAAAATACAC
 151 ATTACAGTTA AATAAATTTA TTTATTTCTG GCTTACAATT AGAGATATTA
 201 CTGTGAAGTG TGAACATGCA TTAGATGGGA AAGAAATATA AAACAATTTC
 251 ATTACATAAA ATTGGGATCT ATTACTAATT AAATGTGGAA TAATCTTAAT
 301 TTTAGTCAAA GTTATAGGGA CACATATTTA AATAAAGTG ATATCTTTCT
 351 TTTCTAAAAG ACAAAATTGA AAAGCAAAAT GTCTTCTTCT CCGTTTAGAA
 401 TAGAACAACA ACAAAAAAAA AACTGTCTTT GAATCCAAGT CTCTCTCTTT
 451 TGTCACCATC TCTGTTACTT ACTAAGAAAC TTCTTTTTCT TTAATGGTTT
 501 TTTTGCTAAA TACCCGTAAT ATTATTAATT AAAGCATTTT CCTTTTTCTG
 551 CTAAATCTTG CTTTGCTCTT TAAGCTCTTG TCATTGTTGT TAATTGTCTC
 601 CTGGAGGCTG GAGGCTGGAG ATTATTTGGT CTTTTGTGAT GACTATAATG
 651 TGAGAAATTC TGGGTTTTGC TAGAATTTGA AGAAATCTTT GAGCAAGGAG
 701 GAAAAAAGAA TGAGACTTTA CTTATCTTCA ACGATGCAGC TTTCTCTTAT
 751 GAGTCTTGTT CTAGGGTTCC TCTTTGTTTC CTGTGACGCG TTTGCCTCTA
 801 AAGAAGGTAT TTTGATTTCT CCATTTTCTC CAATTTTTGG ATGCTGAGAA
 851 AGTTTAGTCT TTTTAGCCTC TGTCTGTTAA CACTTGCTCA TTGAGTTGAT
 901 CTAGAAAGTT AGAAACTTTA GTTTTGTTAC TGATCATTTA GAAGTATTTG
 951 ATGTTTTGCT GTTTTGTATT CAGTTGAAGC AGTTAGAAGA TTCAAGGAAG
1001 CCATTTATAA GGACCCATTG CTAGTTATGT CTAATTGGAA TGTCCCCAAT
1051 TTGAGTCCTT GTGATTGGAA TGGCATTAAA TGTTCTCCAT CTAAGGATCA
1101 CATTATCAAG ATGTAGGAAA CTTTGATCTC TTTCTATCAG TAAAATCAGT
1151 TATGTTTAGT ATGATGATGA TTTGGTATCT GTTTCATGCT GTGAAACTTG
1201 CAGAAATATA TCGGGACAT CGATGAGAGG GTTTCTTGTG CCAGAACTTG
1251 GTCAAATAAC CTACTTGCAA GAACTGTATG GTTTTGATTC ATATTGACAA
1301 TACCTGAAGA TATAAGTTTG ATGATTGGTA CTGTTTGTAA ATGTTTAGAT
1351 GACTTTGTTT TTTCTGTGTT GAATGCTTCT TTAGGATCCT GCGTGGGAAC
1401 ATTCTAATGG GGACAATACC AAAGGAGATA GGAAAGTTAA AGAAACTCAA
1451 GATCTTAGAC CTGGGAAACA ATCATTTGAC AGGACCGATT CCAGCAGAGA
1501 TCGGGAAATT GTCAAGGATT AAGACAATGT AAGAAAATCT TTAAGAGAAT
1551 GTCATCTATC CGATAATGTG CTGAGATAAC CATTTGTGT CTCTTTAACA
1601 CCACAGAAAC CTTCAGTCCA ATGGTTTAAT AGGAAAGTTA CCTCCAGAGA
1651 TTGGAAACTT GAAGCACCTT AAAGAACTTC TTATTGGCAG GAATAGGCTT
1701 CGAGGAAGTA TTCCTATTGC CGCGAAAACA TCAAAAAGT GAGTTTAGCT
1751 AATAGTCCAA GGTAGCATAA GATGGAAACT TAATGTTTAT GATTGAAATG
1801 TTAATGTATC TTCTTTTTGT GTTGGTCAGG TATGCTTCAA ATCCAAGTGC
1851 AAACATCAGT GGTTTGTGCA AGTCTTCTCT ATTTAAAGTG GCAGATTTCT
1901 CTTACAACTT TTTCGAGGGA AGAGTTCCGA GTTGCTTGGA TTACCTCCCA
1951 ATGTATTTCT TATAAGACCC TTTTTCTAGC TTTCCTTTAT TTTTCTCATT
2001 TGATAATATC TCTCTGTATC ATTGAACATC ATTGTAGAAC GAGCTTTCAA
2051 GGAAACTGCA TGAAAACCAT GGATGTTAAG CAGAGACCTC TTTCAGAATG
2101 TGGTTTGTAG AATATGAGTT TCACTTTCTT GATGCTGATA ATCGTTTCTT
2151 TATCTTGTTT TTCATTTTGA AATTGTTTCA ATTGGTTAGC TCGCTTAGCT
2201 GTAACCGTGG CCAAGAAGAA GCATCGAGCA TCGAGACAAA CATGGCTTCG
2251 GAATTTTGAG ATAGTCACGG GATCATCAGT TGGCTTGCTC TTTCTAGTCG
2301 TAATGTTCTC TGCATGTAGC TTGTGCAAAA TAAAGCGCTC TCTCATCGTT
2351 CCCTGGAAGA AATCTGCAAG TGAAAGGAG AAGTTCACGG TCTACGTTGG
2401 TTAGAAACTC TTAAAAATTC TAAGATTTCA ATACAAATAA CTGAAAGAGC
2451 TTCCAGAGAT GAAAAAATTA CTGATAAACT GTTTTTCTAC AGATTCTGAA
2501 ATGCTGAAGG ATGTTTCAAG ATATACAAGA CAAGAGCTAG AAGTAGCATG
2551 TGAAGACTTC AGCAACATCA TTGATTCTAG TGCAGAGAGT CAGATTTACA
2601 AAGGAACGAT CAAAGGCGGG ACTGAGATCG CGGTTATCTC TCTCTGCGTT
2651 AAAGAAGAAA ATTGGACTGG ATATCTTGAG CTTAATTTCC AGAGAGAGGT
2701 TCTTCTTCTT ATGGTTGTTT ATCACCAAGT CACTTGCAAG AAAACATCAG
```

Figure 5 - continued:

```
2751 TATTAAACTT GATTTTATTA ATATTCATTG TTTCAGGTTG CGGCTTTGGC
2801 TAGATTAAAC CATGAGAATG CGGGGAAATT ACTGGGATAC TGTAAAGAGA
2851 GTACACCGTT CACAAGAATG CTTGTGTTTG AGTATGCATC AAACGGGACA
2901 CTATACGACC ATCTCCACTG TAATATATAA TCAAACTTCT TCAGAGCTCT
2951 TTCTTTGGTA GGACTGATAA TGATACCAAA TGATGATAAA AATTTGATGC
3001 AGATGCGGAC GGGAGTTTAG TATCGTGGGC AAAACGCATG AAAATTGTTA
3051 TAGGCATCGC ACGTGGTCTC AAGTACCTTC ATACTGAACT CCATCCTCCA
3101 TTTACAGTCT CTGAGTTGAG CTCAACTGCA GTGTATCTCA CTGAAGATTT
3151 TACTCCCAAA GTAAATTTGA TCCTCTTTTT TCTATGCGGT TAGCTAAGCT
3201 TTGCTACTAT CTCTATACTC TTATTTGAT CCTCTTATTT CTATGCAGCT
3251 GGTTGATTTC GAATGCTGGA AGATTATTCA GGTGAGATCA GAGAAGAACC
3301 TGAAGAATAT CTGTAATGAA GGAGCAATAT GTGTACTTCC CAATGCAATG
3351 GAACACCGAG ATATGGATTT ACAAGGGAAT ATCTACTCAT TTGGCATACT
3401 TTTGCTGGAA ATTGTAAGCG GAAGACCTTC TTATTGCCAA GACAGAGGTT
3451 GCTTGGTTGA ATGGGTAAGA ATAGCTTTTC TCTATAAGCT TAAAGCTGAG
3501 TACTTATAAT AAGTCTCTCT CTCTCTCTTA GCGGTTTACG TGTTTTCATG
3551 CGTTTGATGC TGAGGATTTG ATTCAAACTC CTAAATATTG CAGGTAAGGG
3601 AGAAAAACCT TGGTGCACCA GATGTGATGG CTAGCTTGGT GGATCCTGAG
3651 CTCAAGCATT TCAAGCAAAA AGAACTTGAG GCAGTATGTG AAGTGGCAAG
3701 CCAATGTCTG AACTTGGACC AGAATGAAAA AGACAAGGAT AAGCTTTCTT
3751 GTTCGATTCA AGCGCTTTGT GAGACACTAG AGAGTAGAAT CACTGTGTCC
3801 ATTTCTGCAG AATTCAAATC GTCTTCTCTG GCGTGGGCCG AGCTAGCGCT
3851 GGCCTCGCCT TCTAACGAAG ACGACGATGA TAGGAGTAAA TAAAATTGGC
3901 TTTGTTGTTA TGACATTGAC ATACACTTGT TCGAACATTT TTGCTTCAAT
3951 TTTGCATTCG GTTTTGATAG CACCGACCAT GCCTTGGATA AGTTATCAGG
4001 TAGGTTGTTA CGGTCGGTCT ATTGTTAATA CCAATAAACT GGAGGTGTAA
4051 TCTTGTATAC CAAGTTCTTG ACGAATGAAA TTGTGTTGAG CCAAAAAAGA
4101 AAAAAATGAC AGGTAGCTTG AAACTAGAGG AATACATCTG TGAACCGAAT
4151 AAAAAGTTAT AAACTCTCAC CTTTTCAAAC TAGTTTTGGA CTTCAAACAA
4201 CAATCAGAAA GAAAAAGTAA AAGTACAAAA AAGAGACAAA ATCGTTGGCA
4251 TCTGAAGTAC AGGAGATGTT TGTTGTGTAG GAGAAACAAA GATCAGTGCA
4301 TAGAACGAGA GTAATGGTTG TCATTAGGGT TTCTTTTCTG GCTGAAAACC
4351 GACATAGCTT TTCTCACAGG AGGCTGCAAT GGCGCCTTTC TATCACTATG
4401 ATGGTTCAAG AACACATCAT CTGATACGAA GTACTCATCA CCCTGCAAAC
4451 AACAGCATAA TTTACCTTAA GATTTCAATC AAAGTTACAG ATTTGAGTTT
4501 GAGATAGAAG ACACGAAGAG ACTAACCGGT TTGCTTGCTT TCTTCTTGGT
4551 CCTAGGGTGG AGAAGCTTTT GAGGGAGTTG ATCTTCCCGT AGAATCAGAT
4601 TCTTGGTGAT TGCCTCTCTT CC
```

Figure 6:

```
                    671                                                          730
genomic   (671)  TAGAATTTGAAGAAATCTTTGAGCAAGGAGGAAAAAAGAATGAGACTTTACTTATCTTCA
  RLK-1     (1)  ---------------------------------------ATGAGACTTTACTTATCTTCA
                    731                                                          790
genomic   (731)  ACGATGCAGCTTTCTCTTATGAGTCTTGTTCTAGGGTTCCTCTTTGTTTCCTGTGACGCG
  RLK-1    (22)  ACGATGCAGCTTTCTCTTATGAGTCTTGTTCTAGGGTTCCTCTTTGTTTCCTGTGACGCG
                    791                                                          850
genomic   (791)  TTTGCCTCTAAAGAAGGTATTTTGATTTCTCCATTTTCTCCAATTTTTGGATGCTGAGAA
  RLK-1    (82)  TTTGCCTCTAAAGAAG--------------------------------------------
                    851                                                          910
genomic   (851)  AGTTTAGTCTTTTTAGCCTCTGTCTGTTAACACTTGCTCATTGAGTTGATCTAGAAAGTT
  RLK-1    (98)  ------------------------------------------------------------
                    911                                                          970
genomic   (911)  AGAAACTTTAGTTTTGTTACTGATCATTTAGAAGTATTTGATGTTTTGCTGTTTTGTATT
  RLK-1    (98)  ------------------------------------------------------------
                    971                                                         1030
genomic   (971)  CAGTTGAAGCAGTTAGAAGATTCAAGGAAGCCATTTATAAGGACCCATTGCTAGTTATGT
  RLK-1    (98)  ---TTGAAGCAGTTAGAAGATTCAAGGAAGCCATTTATAAGGACCCATTGCTAGTTATGT
                   1031                                                         1090
genomic  (1031)  CTAATTGGAATGTCCCCAATTTGAGTCCTTGTGATTGGAATGGCATTAAATGTTCTCCAT
  RLK-1   (155)  CTAATTGGAATGTCCCCAATTTGAGTCCTTGTGATTGGAATGGCATTAAATGTTCTCCAT
                   1091                                                         1150
genomic  (1091)  CTAAGGATCACATTATCAAGATGTAGGAAACTTTGATCTCTTTCTATCAGTAAAATCAGT
  RLK-1   (215)  CTAAGGATCACATTATCAAGAT--------------------------------------
                   1151                                                         1210
genomic  (1151)  TATGTTTAGTATGATGATGATTTGGTATCTGTTTCATGCTGTGAAACTTGCAGAAATATA
  RLK-1   (237)  ------------------------------------------------------AAATATA
                   1211                                                         1270
genomic  (1211)  TCGGGGACATCGATGAGAGGGTTTCTTGTGCCAGAACTTGGTCAAATAACCTACTTGCAA
  RLK-1   (244)  TCGGGGACATCGATGAGAGGGTTTCTTGTGCCAGAACTTGGTCAAATAACCTACTTGCAA
                   1271                                                         1330
genomic  (1271)  GAACTGTATGGTTTTGATTCATATTGACAATACCTGAAGATATAAGTTTGATGATTGGTA
  RLK-1   (304)  GAACTG------------------------------------------------------
                   1331                                                         1390
genomic  (1331)  CTGTTTGTAAATGTTTAGATGACTTTGTTTTTTCTGTGTTGAATGCTTCTTTAGGATCCT
  RLK-1   (310)  ----------------------------------------------------ATCCT
                   1391                                                         1450
genomic  (1391)  GCGTGGGAACATTCTAATGGGGACAATACCAAAGGAGATAGGAAAGTTAAAGAAACTCAA
  RLK-1   (315)  GCGTGGGAACATTCTAATGGGGACAATACCAAAGGAGATAGGAAAGTTAAAGAAACTCAA
                   1451                                                         1510
genomic  (1451)  GATCTTAGACCTGGGAAACAATCATTTGACAGGACCGATTCCAGCAGAGATCGGGAAATT
  RLK-1   (375)  GATCTTAGACCTGGGAAACAATCATTTGACAGGACCGATTCCAGCAGAGATCGGGAAATT
                   1511                                                         1570
genomic  (1511)  GTCAAGGATTAAGACAATGTAAGAAAATCTTTAAGAGAATGTCATCTATCCGATAATGTG
  RLK-1   (435)  GTCAAGGATTAAGACAAT------------------------------------------
                   1571                                                         1630
genomic  (1571)  CTGAGATAACCATTTTGTGTCTCTTTAACACCACAGAAACCTTCAGTCCAATGGTTTAAT
  RLK-1   (453)  -------------------------------------AAACCTTCAGTCCAATGGTTTAAT
                   1631                                                         1690
genomic  (1631)  AGGAAAGTTACCTCCAGAGATTGGAAACTTGAAGCACCTTAAAGAACTTCTTATTGGCAG
  RLK-1   (477)  AGGAAAGTTACCTCCAGAGATTGGAAACTTGAAGCACCTTAAAGAACTTCTTATTGGCAG
                   1691                                                         1750
genomic  (1691)  GAATAGGCTTCGAGGAAGTATTCCTATTGCCGCGAAAACATCAAAAAAGTGAGTTTAGCT
  RLK-1   (537)  GAATAGGCTTCGAGGAAGTATTCCTATTGCCGCGAAAACATCAAAAAAGT----------
                   1751                                                         1810
genomic  (1751)  AATAGTCCAAGGTAGCATAAGATGGAAACTTAATGTTTATGATTGAAATGTTAATGTATC
  RLK-1   (587)  ------------------------------------------------------------
                   1811                                                         1870
genomic  (1811)  TTCTTTTTGTGTTGGTCAGGTATGCTTCAAATCCAAGTGCAAACATCAGTGGTTTGTGCA
  RLK-1   (587)  ------------------ATGCTTCAAATCCAAGTGCAAACATCAGTGGTTTGTGCA
                   1871                                                         1930
genomic  (1871)  AGTCTTCTCTATTTAAAGTGGCAGATTTTCTCTTACAACTTTTTCGAGGGAAGAGTTCCGA
  RLK-1   (626)  AGTCTTCTCTATTTAAAGTGGCAGATTTTCTCTTACAACTTTTTCGAGGGAAGAGTTCCGA
                   1931                                                         1990
```

Figure 6 - continued:

```
genomic   (1931)  GTTGCTTGGATTACCTCCCAATGTATTTCTTATAAGACCCTTTTTCTAGCTTTCCTTTAT
  RLK-1    (686)  GTTGCTTGGATTACCTCCCAAT---------------------------------------
                  1991                                                        2050
genomic   (1991)  TTTTCTCATTTGATAATATCTCTCTGTATCATTGAACATCATTGTAGAACGAGCTTTCAA
  RLK-1    (708)  ------------------------------------------------AACGAGCTTTCAA
                  2051                                                        2110
genomic   (2051)  GGAAACTGCATGAAAACCATGGATGTTAAGCAGAGACCTCTTTCAGAATGTGGTTTGTAG
  RLK-1    (721)  GGAAACTGCATGAAAACCATGGATGTTAAGCAGAGACCTCTTTCAGAATGTG--------
                  2111                                                        2170
genomic   (2111)  AATATGAGTTTCACTTTCTTGATGCTGATAATCGTTTCTTTATCTTGTTTTTCATTTTGA
  RLK-1    (773)  ------------------------------------------------------------
                  2171                                                        2230
genomic   (2171)  AATTGTTTCAATTGGTTAGCTCGCTTAGCTGTAACCGTGGCCAAGAAGAAGCATCGAGCA
  RLK-1    (773)  ------------------GTCGCTTAGCTGTAACCGTGGCCAAGAAGAAGCATCGAGCA
                  2231                                                        2290
genomic   (2231)  TCGAGACAAACATGGCTTCGGAATTTTGAGATAGTCACGGGATCATCAGTTGGCTTGCTC
  RLK-1    (814)  TCGAGACAAACATGGCTTCGGAATTTTGAGATAGTCACGGGATCATCAGTTGGCTTGCTC
                  2291                                                        2350
genomic   (2291)  TTTCTAGTCGTAATGTTCTCTGCATGTAGCTTGTGCAAAATAAAGCGCTCTCTCATCGTT
  RLK-1    (874)  TTTCTAGTCGTAATGTTCTCTGCATGTAGCTTGTGCAAAATAAAGCGCTCTCTCATCGTT
                  2351                                                        2410
genomic   (2351)  CCCTGGAAGAAATCTGCAAGTGAAAAGGAGAAGTTCACGGTCTACGTTGGTTAGAAACTC
  RLK-1    (934)  CCCTGGAAGAAATCTGCAAGTGAAAAGGAGAAGTTCACGGTCTACGTTG-----------
                  2411                                                        2470
genomic   (2411)  TTAAAAATTCTAAGATTTCAATACAAATAACTGAAAGAGCTTCCAGAGATGAAAAAATTA
  RLK-1    (983)  ------------------------------------------------------------
                  2471                                                        2530
genomic   (2471)  CTGATAAACTGTTTTTCTACAGATTCTGAAATGCTGAAGGATGTTTCAAGATATACAAGA
  RLK-1    (983)  ----------------------ATTCTGAAATGCTGAAGGATGTTTCAAGATATACAAGA
                  2531                                                        2590
genomic   (2531)  CAAGAGCTAGAAGTAGCATGTGAAGACTTCAGCAACATCATTGATTCTAGTGCAGAGAGT
  RLK-1   (1021)  CAAGAGCTAGAAGTAGCATGTGAAGACTTCAGCAACATCATTGATTCTAGTGCAGAGAGT
                  2591                                                        2650
genomic   (2591)  CAGATTTACAAAGGAACGATCAAAGGCGGGACTGAGATCGCGGTTATCTCTCTCTGCGTT
  RLK-1   (1081)  CAGATTTACAAAGGAACGATCAAAGGCGGGACTGAGATCGCGGTTATCTCTCTCTGCGTT
                  2651                                                        2710
genomic   (2651)  AAAGAAGAAAATTGGACTGGATATCTTGAGCTTAAATTTCCAGAGAGAGGTTCTTCTTCTT
  RLK-1   (1141)  AAAGAAGAAAATTGGACTGGATATCTTGAGCTTAAATTTCCAGAGAGAGGTT---------
                  2711                                                        2770
genomic   (2711)  ATGGTTGTTTATCACCAAGTCACTTGCAAGAAAACATCAGTATTAAACTTGATTTTATTA
  RLK-1   (1192)  ------------------------------------------------------------
                  2771                                                        2830
genomic   (2771)  ATATTCATTGTTTCAGGTTGCGGCTTTGGCTAGATTAAACCATGAGAATGCGGGGAAATT
  RLK-1   (1192)  ------------------GCGGCTTTGGCTAGATTAAACCATGAGAATGCGGGGAAATT
                  2831                                                        2890
genomic   (2831)  ACTGGGATACTGTAAAGAGAGTACACCGTTCACAAGAATGCTTGTGTTTGAGTATGCATC
  RLK-1   (1233)  ACTGGGATACTGTAAAGAGAGTACACCGTTCACAAGAATGCTTGTGTTTGAGTATGCATC
                  2891                                                        2950
genomic   (2891)  AAACGGGACACTATACGACCATCTCCACTGTAATATATAATCAAACTTCTTCAGAGCTCT
  RLK-1   (1293)  AAACGGGACACTATACGACCATCTCCACT-------------------------------
                  2951                                                        3010
genomic   (2951)  TTCTTTGGTAGGACTGATAATGATACCAAATGATGATAAAAATTTGATGCAGATGCGGAC
  RLK-1   (1322)  ---------------------------------------------------ATGCGGAC
                  3011                                                        3070
genomic   (3011)  GGGAGTTTAGTATCGTGGGCAAAACGCATGAAAATTGTTATAGGCATCGCACGTGGTCTC
  RLK-1   (1330)  GGGACTTTAGTATCGTGGGCAAAACGCATGAAAATTGTTATAGGCATCGCACGTGGTCTC
                  3071                                                        3130
genomic   (3071)  AAGTACCTTCATACTGAACTCCATCCTCCATTTACAGTCTCTGAGTTGAGCTCAACTGCA
  RLK-1   (1390)  AAGTACCTTCATACTGAACTCCATCCTCCATTTACAGTCTCTGAGTTGAGCTCAACTGCA
                  3131                                                        3190
genomic   (3131)  GTGTATCTCACTGAAGATTTTACTCCCAAAGTAAATTTGATCCTCTTTTTTCTATGCGGT
  RLK-1   (1450)  GTGTATCTCACTGAAGATTTTACTCCCAAA------------------------------
                  3191                                                        3250
genomic   (3191)  TAGCTAAGCTTTGCTACTATCTCTATACTCTTATTTTGATCCTCTTATTTCTATGCAGCT
```

Figure 6 – continued:

```
   RLK-1  (1480)  ------------------------------------------------------------C T
                  3251                                                         3310
 genomic  (3251)  GGTTGATTTCGAATGCTGGAAGATTATTCAGGTGAGATCAGAGAAGAACCTGAAGAATAT
   RLK-1  (1482)  GGTTGATTTCGAATGCTGGAAGATTATTCAGGTGAGATCAGAGAAGAACCTGAAGAATAT
                  3311                                                         3370
 genomic  (3311)  CTGTAATGAAGGAGCAATATGTGTACTTCCCAATGCAATGGAACACCGAGATATGGATT
   RLK-1  (1542)  CTGTAATGAAGGAGCAATATGTGTACTTCCCAATGCAATGGAACACCGAGATATGGATT
                  3371                                                         3430
 genomic  (3371)  ACAAGGGAATATCTACTCATTTGGCATACTTTGCTGGAAATTGTAAGCGGAAGACCTTC
   RLK-1  (1602)  ACAAGGGAATATCTACTCATTTGGCATACTTTGCTGGAAATTGTAAGCGGAAGACCTTC
                  3431                                                         3490
 genomic  (3431)  TTATTGCCAAGACAGAGGTTGCTTGGTTGAATGGGTAAGAATAGCTTTTCTCTATAAGCT
   RLK-1  (1662)  TTATTGCCAAGACAGAGGTTGCTTGGTTGAATGGGTAAG---------------------
                  3491                                                         3550
 genomic  (3491)  TAAAGCTGAGTACTTATAATAAGTCTCTCTCTCTCTTAGCGGTTTACGTGTTTTCATG
   RLK-1  (1701)  ------------------------------------------------------------
                  3551                                                         3610
 genomic  (3551)  CGTTTGATGCTGAGGATTTGATTCAAACTCCTAAATATTGCAGGTAAGGGAGAAAAACCT
   RLK-1  (1701)  ----------------------------------------------CGAGAAAAACCT
                  3611                                                         3670
 genomic  (3611)  TGGTGCACCAGATGTGATGGCTAGCTTGGTGGATCCTGAGCTCAAGCATTTCAAGCAAAA
   RLK-1  (1713)  TGGTGCACCAGATGTGATGGCTAGCTTGGTGGATCCTGAGCTCAAGCATTTCAAGCAAAA
                  3671                                                         3730
 genomic  (3671)  AGAACTTGAGGCAGTATGTGAAGTGGCAAGCCAATGTCTGAACTTGGACCAGAATGAAAA
   RLK-1  (1773)  AGAACTTGAGGCAGTATGTGAAGTGGCAAGCCAATGTCTGAACTTGGACCAGAATGAAAA
                  3731                                                         3790
 genomic  (3731)  AGACAAGGATAAGCTTTCTTGTTCGATTCAAGCGCTTTGTGAGACACTAGAGAGTAGAAT
   RLK-1  (1833)  AGACAAGGATAAGCTTTCTTGTTCGATTCAAGCGCTTTGTGAGACACTAGAGAGTAGAAT
                  3791                                                         3850
 genomic  (3791)  CACTGTGTCCATTTCTGCAGAATTCAAATCGTCTTCTCTGGCGTGGGCCGAGCTAGCGCT
   RLK-1  (1893)  CACTGTGTCCATTTCTGCAGAATTCAAATCGTCTTCTCTGGCGTGGGCCGAGCTAGCGCT
                  3851                                                         3910
 genomic  (3851)  GGCCTCGCCTTCTAACGAAGACGACGATGATAGGAGTAAATAAAATTGGCTTTGTTGTTA
   RLK-1  (1953)  GGCCTCGCCTTCTAACGAAGACGACGATGATAGGAGTAAATAA-----------------
                  3911       3929
 genomic  (3911)  TGACATTGACATACACTTG
   RLK-1  (1996)  -------------------
```

Figure 7:

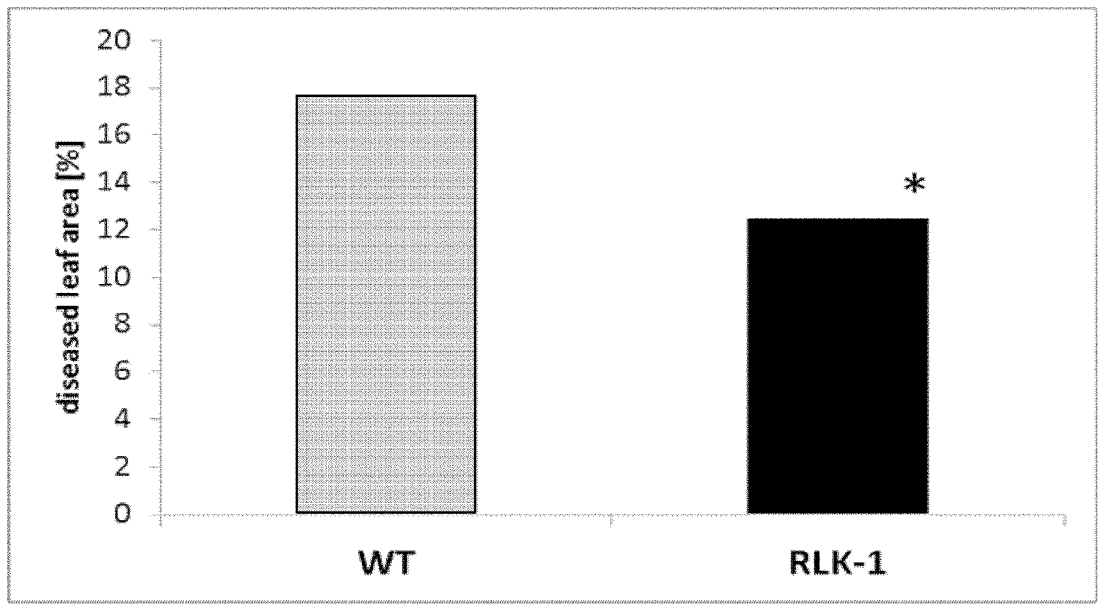

Figure 8:

| SEQ ID NO: | Description of the sequence listing |
|---|---|
| 1 | Nucleotide sequence RLK1 cDNA; Arabidopsis thaliana |
| 2 | Amino acid sequence RLK1; Arabidopsis thaliana |
| 3 | Nucleotide sequence RLK1 genomic sequence; Arabidopsis thaliana |
| 4 | RLK1 forward primer |
| 5 | RLK1 reverse primer |
| 6 | RLK1 forward reamplification primer |
| 7 | RLK1 reverse reamplification primer |
| 8 | Nucleotide sequence RLK1 genomic sequence; truncated as in Fig. 6; Arabidopsis thaliana |
| 9 | Nucleotide sequence RLK1; variant of cDNA; Arabidopsis thaliana |
| 10 | Amino acid sequence RLK1; variant of cDNA; Arabidopsis thaliana |
| 11 | Nucleotide sequence RLK1, variant 1 |
| 12 | Nucleotide sequence RLK1, variant 2 |
| 13 | Nucleotide sequence RLK1, variant 3 |
| 14 | Nucleotide sequence RLK1, variant 4 |
| 15 | Nucleotide sequence RLK1, variant 5 |
| 16 | Nucleotide sequence RLK1, variant 6 |

Figure 8 (continued):

| SEQ ID NO: | Description of the sequence listing |
|---|---|
| 17 | Nucleotide sequence RLK1, variant 7 |
| 18 | Nucleotide sequence RLK1, variant 8 |
| 19 | Nucleotide sequence RLK1, variant 9 |
| 20 | Amino acid sequence RLK1, variant 9 |
| 21 | Nucleotide sequence RLK1, variant 10 |
| 22 | Amino acid sequence RLK1, variant 10 |
| 23 | Nucleotide sequence RLK1, variant 11 |
| 24 | Amino acid sequence RLK1, variant 11 |
| 25 | Nucleotide sequence RLK1, variant 12 |
| 26 | Amino acid sequence RLK1, variant 12 |
| 27 | Nucleotide sequence RLK1, variant 13 |
| 28 | Amino acid sequence RLK1, variant 13 |
| 29 | Nucleotide sequence RLK1, variant 14 |
| 30 | Amino acid sequence RLK1, variant 14 |
| 31 | Nucleotide sequence RLK1, variant 15 |
| 32 | Amino acid sequence RLK1, variant 15 |
| 33 | Nucleotide sequence RLK1, variant 16 |
| 34 | Amino acid sequence RLK1, variant 16 |

SEQUENCE LISTING

```
<160> NUMBER OF SEQ ID NOS: 34

<210> SEQ ID NO 1
<211> LENGTH: 1995
<212> TYPE: DNA
<213> ORGANISM: Arabidopsis thaliana
```

```
<220> FEATURE:
<221> NAME/KEY: source
<222> LOCATION: 1..1995
<223> OTHER INFORMATION: /organism="Arabidopsis thaliana"
      /mol_type="unassigned DNA"

<400> SEQUENCE: 1
atgagacttt acttatcttc aacgatgcag ctttctctta tgagtcttgt tctagggttc      60
ctctttgttt cctgtgacgc gtttgcctct aaagaagttg aagcagttag aagattcaag     120
gaagccattt ataaggaccc attgctagtt atgtctaatt ggaatgtccc caatttgagt     180
ccttgtgatt ggaatggcat taaatgttct ccatctaagg atcacattat caagataaat     240
atatcgggga catcgatgag agggtttctt gtgccagaac ttggtcaaat aacctacttg     300
caagaactga tcctgcgtgg gaacattcta atggggacaa taccaaagga gataggaaag     360
ttaaagaaac tcaagatctt agacctggga aacaatcatt tgacaggacc gattccagca     420
gagatcggga aattgtcaag gattaagaca ataaaccttc agtccaatgg tttaatagga     480
aagttacctc cagagattgg aaacttgaag caccttaaag aacttcttat tggcaggaat     540
aggcttcgag gaagtattcc tattgccgcg aaaacatcaa aaagtatgc ttcaaatcca      600 agtgcaaaca tcagtggttt gtgcaagtct tctctattta aagtggcaga tttctcttac     660
aactttttcg agggaagagt tccgagttgc ttggattacc tcccaataac gagctttcaa     720
ggaaactgca tgaaaaccat ggatgttaag cagagacctc tttcagaatg tgctcgctta     780
gctgtaaccg tggccaagaa gaagcatcga gcatcgagac aaacatggct tcggaatttt     840
gagatagtca cgggatcatc agttggcttg ctctttctag tcgtaatgtt ctctgcatgt     900
agcttgtgca aaataaagcg ctctctcatc gttccctgga gaaatctgc aagtgaaaag      960 gagaagttca cggtctacgt tgattctgaa atgctgaagg atgtttcaag atatacaaga    1020
caagagctag aagtagcatg tgaagacttc agcaacatca ttgattctag tgcagagagt    1080
cagatttaca aaggaacgat caaaggcggg actgagatcg cggttatctc tctctgcgtt    1140
aaagaagaaa attggactgg atatcttgag cttaatttcc agagagaggt tgcggctttg    1200
gctagattaa accatgagaa tgcggggaaa ttactgggat actgtaaaga gagtacaccg    1260
ttcacaagaa tgcttgtgtt tgagtatgca tcaaacggga cactatacga ccatctccac    1320
tatgcggacg ggagtttagt atcgtgggca aaacgcatga aaattgttat aggcatcgca    1380
cgtggtctca agtaccttca tactgaactc catcctccat ttacagtctc tgagttgagc    1440
tcaactgcag tgtatctcac tgaagatttt actcccaaac tggttgattt cgaatgctgg    1500
aagattattc aggtgagatc agagaagaac ctgaagaata tctgtaatga aggagcaata    1560
tgtgtacttc ccaatgcaat ggaacaccga gatatggatt tacaagggaa tatctactca    1620
tttggcatac ttttgctgga aattgtaagc ggaagaccct cttattgcca agacagaggt    1680
tgcttggttg aatgggtaag ggagaaaaac cttggtgcac cagatgtgat ggctagcttg    1740
gtggatcctg agctcaagca tttcaagcaa aaagaacttg aggcagtatg tgaagtggca    1800
agccaatgtc tgaacttgga ccagaatgaa aaagacaagg ataagctttc ttgttcgatt    1860
caagcgcttt gtgagacact agagagtaga atcactgtgt ccatttctgc agaattcaaa    1920
tcgtcttctc tggcgtgggc cgagctagcg ctggcctcgc cttctaacga agacgacgat    1980
gataggagta aataa                                                     1995

<210> SEQ ID NO 2
<211> LENGTH: 664
```

```
<212> TYPE: PRT
<213> ORGANISM: Arabidopsis thaliana

<400> SEQUENCE: 2

Met Arg Leu Tyr Leu Ser Ser Thr Met Gln Leu Ser Leu Met Ser Leu
1               5                   10                  15

Val Leu Gly Phe Leu Phe Val Ser Cys Asp Ala Phe Ala Ser Lys Glu
            20                  25                  30

Val Glu Ala Val Arg Arg Phe Lys Glu Ala Ile Tyr Lys Asp Pro Leu
        35                  40                  45

Leu Val Met Ser Asn Trp Asn Val Pro Asn Leu Ser Pro Cys Asp Trp
    50                  55                  60

Asn Gly Ile Lys Cys Ser Pro Ser Lys Asp His Ile Ile Lys Ile Asn
65                  70                  75                  80

Ile Ser Gly Thr Ser Met Arg Gly Phe Leu Val Pro Glu Leu Gly Gln
                85                  90                  95

Ile Thr Tyr Leu Gln Glu Leu Ile Leu Arg Gly Asn Ile Leu Met Gly
            100                 105                 110

Thr Ile Pro Lys Glu Ile Gly Lys Leu Lys Lys Leu Lys Ile Leu Asp
        115                 120                 125

Leu Gly Asn Asn His Leu Thr Gly Pro Ile Pro Ala Glu Ile Gly Lys
    130                 135                 140

Leu Ser Arg Ile Lys Thr Ile Asn Leu Gln Ser Asn Gly Leu Ile Gly
145                 150                 155                 160

Lys Leu Pro Pro Glu Ile Gly Asn Leu Lys His Leu Lys Glu Leu Leu
                165                 170                 175

Ile Gly Arg Asn Arg Leu Arg Gly Ser Ile Pro Ile Ala Ala Lys Thr
            180                 185                 190

Ser Lys Lys Tyr Ala Ser Asn Pro Ser Ala Asn Ile Ser Gly Leu Cys
        195                 200                 205

Lys Ser Ser Leu Phe Lys Val Ala Asp Phe Ser Tyr Asn Phe Phe Glu
    210                 215                 220

Gly Arg Val Pro Ser Cys Leu Asp Tyr Leu Pro Ile Thr Ser Phe Gln
225                 230                 235                 240

Gly Asn Cys Met Lys Thr Met Asp Val Lys Gln Arg Pro Leu Ser Glu
                245                 250                 255

Cys Ala Arg Leu Ala Val Thr Val Ala Lys Lys Lys His Arg Ala Ser
            260                 265                 270

Arg Gln Thr Trp Leu Arg Asn Phe Glu Ile Val Thr Gly Ser Ser Val
        275                 280                 285

Gly Leu Leu Phe Leu Val Val Met Phe Ser Ala Cys Ser Leu Cys Lys
    290                 295                 300

Ile Lys Arg Ser Leu Ile Val Pro Trp Lys Ser Ala Ser Glu Lys
305                 310                 315                 320

Glu Lys Phe Thr Val Tyr Val Asp Ser Glu Met Leu Lys Asp Val Ser
                325                 330                 335

Arg Tyr Thr Arg Gln Glu Leu Glu Val Ala Cys Glu Asp Phe Ser Asn
            340                 345                 350

Ile Ile Asp Ser Ser Ala Glu Ser Gln Ile Tyr Lys Gly Thr Ile Lys
        355                 360                 365

Gly Gly Thr Glu Ile Ala Val Ile Ser Leu Cys Val Lys Glu Glu Asn
    370                 375                 380

Trp Thr Gly Tyr Leu Glu Leu Asn Phe Gln Arg Glu Val Ala Ala Leu
385                 390                 395                 400
```

-continued

Ala Arg Leu Asn His Glu Asn Ala Gly Lys Leu Leu Gly Tyr Cys Lys
            405                 410                 415

Glu Ser Thr Pro Phe Thr Arg Met Leu Val Phe Glu Tyr Ala Ser Asn
        420                 425                 430

Gly Thr Leu Tyr Asp His Leu His Tyr Ala Asp Gly Ser Leu Val Ser
            435                 440                 445

Trp Ala Lys Arg Met Lys Ile Val Gly Ile Ala Arg Gly Leu Lys
    450                 455                 460

Tyr Leu His Thr Glu Leu His Pro Pro Phe Thr Val Ser Glu Leu Ser
465                 470                 475                 480

Ser Thr Ala Val Tyr Leu Thr Glu Asp Phe Thr Pro Lys Leu Val Asp
                485                 490                 495

Phe Glu Cys Trp Lys Ile Ile Gln Val Arg Ser Glu Lys Asn Leu Lys
            500                 505                 510

Asn Ile Cys Asn Glu Gly Ala Ile Cys Val Leu Pro Asn Ala Met Glu
        515                 520                 525

His Arg Asp Met Asp Leu Gln Gly Asn Ile Tyr Ser Phe Gly Ile Leu
    530                 535                 540

Leu Leu Glu Ile Val Ser Gly Arg Pro Ser Tyr Cys Gln Asp Arg Gly
545                 550                 555                 560

Cys Leu Val Glu Trp Val Arg Glu Lys Asn Leu Gly Ala Pro Asp Val
                565                 570                 575

Met Ala Ser Leu Val Asp Pro Glu Leu Lys His Phe Lys Gln Lys Glu
            580                 585                 590

Leu Glu Ala Val Cys Glu Val Ala Ser Gln Cys Leu Asn Leu Asp Gln
        595                 600                 605

Asn Glu Lys Asp Lys Asp Lys Leu Ser Cys Ser Ile Gln Ala Leu Cys
    610                 615                 620

Glu Thr Leu Glu Ser Arg Ile Thr Val Ser Ile Ser Ala Glu Phe Lys
625                 630                 635                 640

Ser Ser Ser Leu Ala Trp Ala Glu Leu Ala Leu Ala Ser Pro Ser Asn
                645                 650                 655

Glu Asp Asp Asp Arg Ser Lys
            660

<210> SEQ ID NO 3
<211> LENGTH: 4622
<212> TYPE: DNA
<213> ORGANISM: Arabidopsis thaliana
<220> FEATURE:
<221> NAME/KEY: source
<222> LOCATION: 1..4622
<223> OTHER INFORMATION: /organism="Arabidopsis thaliana"
      /mol_type="unassigned DNA"

<400> SEQUENCE: 3
ttaaaattta ttggaaacgt atatattttg tttttattta atgtaataat attttgtctt      60
ctttcacatt ttaagcaggt tatatattga ctataaatgt ttcacagata gatgcatgtt     120
gatacatttt tccttgtata caaaatacac attacagtta aataaattta tttatttctg     180
gcttacaatt agagatatta ctgtgaagtg tgaacatgca ttagatggga agaaatata      240 aaacaatttc attacataaa attgggatct attactaatt aaatgtggaa taatcttaat     300
tttagtcaaa gttataggga cacatattta aataaaagtg atatctttct tttctaaaag     360
acaaaattga aaagcaaaat gtcttcttct ccgtttagaa tagaacaaca acaaaaaaaa     420

```
aactgtcttt gaatccaagt ctctctcttt tgtcaccatc tctgttactt actaagaaac    480 ttcttttttct ttaatggttt ttttgctaaa tacccgtaat attattaatt aaagcatttt    540 ccttttctg ctaaatcttg ctttgctctt taagctcttg tcattgttgt taattgtctc    600
ctggaggctg gaggctggag attatttggt cttttgtgat gactataatg tgagaaattc    660
tgggttttgc tagaatttga agaaatcttt gagcaaggag gaaaaagaa tgagacttta    720 cttatcttca acgatgcagc tttctcttat gagtcttgtt ctagggttcc tctttgtttc    780
ctgtgacgcg tttgcctcta aagaaggtat tttgatttct ccatttctc caattttggg    840 atgctgagaa agtttagtct ttttagcctc tgtctgttaa cacttgctca ttgagttgat    900
ctagaaagtt agaaacttta gttttgttac tgatcattta gaagtatttg atgttttgct    960
gttttgtatt cagttgaagc agttagaaga ttcaaggaag ccatttataa ggacccattg   1020
ctagttatgt ctaattggaa tgtccccaat ttgagtcctt gtgattggaa tggcattaaa   1080
tgttctccat ctaaggatca cattatcaag atgtaggaaa ctttgatctc tttctatcag   1140
taaaatcagt tatgtttagt atgatgatga tttggtatct gtttcatgct gtgaaacttg   1200
cagaaatata tcggggacat cgatgagagg gtttcttgtg ccagaacttg gtcaaataac   1260
ctacttgcaa gaactgtatg gttttgattc atattgacaa tacctgaaga tataagtttg   1320
atgattggta ctgtttgtaa atgtttagat gactttgttt tttctgtgtt gaatgcttct   1380
ttaggatcct gcgtgggaac attctaatgg ggacaatacc aaaggagata ggaaagttaa   1440
agaaactcaa gatcttagac ctgggaaaca atcatttgac aggaccgatt ccagcagaga   1500
tcgggaaatt gtcaaggatt aagacaatgt aagaaaatct taagagaat gtcatctatc   1560 cgataatgtg ctgagataac cattttgtgt ctctttaaca ccacagaaac cttcagtcca   1620
atggtttaat aggaaagtta cctccagaga ttggaaactt gaagcacctt aaagaacttc   1680
ttattggcag gaataggctt cgaggaagta ttcctattgc cgcgaaaaca tcaaaaagt   1740 gagtttagct aatagtccaa ggtagcataa gatggaaact taatgtttat gattgaaatg   1800
ttaatgtatc ttcttttgt gttggtcagg tatgcttcaa atccaagtgc aaacatcagt   1860
ggtttgtgca agtcttctct atttaaagtg gcagatttct cttacaactt tttcgaggga   1920
agagttccga gttgcttgga ttacctccca atgtatttct tataagaccc tttttctagc   1980
tttcctttat ttttctcatt tgataatatc tctctgtatc attgaacatc attgtagaac   2040
gagctttcaa ggaaactgca tgaaaaccat ggatgttaag cagagacctc tttcagaatg   2100
tggtttgtag aatatgagtt tcactttctt gatgctgata tcgttctt tatcttgttt     2160 ttcattttga aattgtttca attggttagc tcgcttagct gtaaccgtgg ccaagaagaa   2220
gcatcgagca tcgagacaaa catggcttcg gaattttgag atagtcacgg gatcatcagt   2280
tggcttgctc tttctagtcg taatgttctc tgcatgtagc ttgtgcaaaa taaagcgctc   2340
tctcatcgtt ccctggaaga aatctgcaag tgaaaggag aagttcacgg tctacgttgg    2400
ttagaaactc ttaaaaattc taagatttca atacaaataa ctgaaagagc ttccagagat   2460 gaaaaatta ctgataaact gttttctac agattctgaa atgctgaagg atgtttcaag    2520
atatacaaga caagagctag aagtagcatg tgaagacttc agcaacatca ttgattctag   2580
tgcagagagt cagatttaca aaggaacgat caaaggcggg actgagatcg cggttatctc   2640
tctctgcgtt aaagaagaaa attggactgg atatcttgag cttaatttcc agagagaggt   2700
tcttcttctt atggttgttt atcaccaagt cacttgcaag aaaacatcag tattaaactt   2760
gatttattta atattcattg tttcaggttg cggctttggc tagattaaac catgagaatg   2820
```

```
cggggaaatt actgggatac tgtaaagaga gtacaccgtt cacaagaatg cttgtgtttg      2880
agtatgcatc aaacgggaca ctatacgacc atctccactg taatatataa tcaaacttct      2940
tcagagctct ttctttggta ggactgataa tgataccaaa tgatgataaa aatttgatgc      3000
agatgcggac gggagtttag tatcgtgggc aaaacgcatg aaaattgtta taggcatcgc      3060
acgtggtctc aagtaccttc atactgaact ccatcctcca tttacagtct ctgagttgag      3120
ctcaactgca gtgtatctca ctgaagattt tactcccaaa gtaaatttga tcctcttttt      3180
tctatgcggt tagctaagct ttgctactat ctctatactc ttattttgat cctcttattt      3240
ctatgcagct ggttgatttc gaatgctgga agattattca ggtgagatca gagaagaacc      3300
tgaagaatat ctgtaatgaa ggagcaatat gtgtacttcc caatgcaatg gaacaccgag      3360
atatggattt acaagggaat atctactcat ttggcatact tttgctggaa attgtaagcg      3420 gaagacccttc ttattgccaa gacagaggtt gcttggttga atgggtaaga atagcttttc     3480
tctataagct taaagctgag tacttataat aagtctctct ctctctctta gcggtttacg      3540
tgttttcatg cgtttgatgc tgaggatttg attcaaactc ctaaatattg caggtaaggg      3600
agaaaaacct tggtgcacca gatgtgatgg ctagcttggt ggatcctgag ctcaagcatt      3660
tcaagcaaaa agaacttgag gcagtatgtg aagtggcaag ccaatgtctg aacttggacc      3720
agaatgaaaa agacaaggat aagctttctt gttcgattca agcgctttgt gagacactag      3780
agagtagaat cactgtgtcc atttctgcag aattcaaatc gtcttctctg gcgtgggccg      3840
agctagcgct ggcctcgcct tctaacgaag acgacgatga taggagtaaa taaaattggc      3900
tttgttgtta tgacattgac atacacttgt tcgaacattt ttgcttcaat tttgcattcg      3960
gttttgatag caccgaccat gccttggata agttatcagg taggttgtta cggtcggtct      4020
attgttaata ccaataaact ggaggtgtaa tcttgtatac caagttcttg acgaatgaaa      4080
ttgtgttgag ccaaaaaaga aaaaatgac aggtagcttg aaactagagg aatacatctg       4140
tgaaccgaat aaaaagttat aaactctcac cttttcaaac tagttttgga cttcaaacaa      4200
caatcagaaa gaaaaagtaa aagtacaaaa aagagacaaa atcgttggca tctgaagtac      4260
aggagatgtt tgttgtgtag gagaaacaaa gatcagtgca tagaacgaga gtaatggttg      4320
tcattagggt ttcttttctg gctgaaaacc gacatagctt ttctcacagg aggctgcaat      4380
ggcgcctttc tatcactatg atggttcaag aacacatcat ctgatacgaa gtactcatca      4440
ccctgcaaac aacagcataa tttaccttaa gatttcaatc aaagttacag atttgagttt      4500
gagatagaag acacgaagag actaaccggt ttgcttgctt tcttcttggt cctagggtgg      4560
agaagctttt gagggagttg atcttcccgt agaatcagat tcttggtgat gcctctcttt      4620
cc                                                                    4622
```

<210> SEQ ID NO 4
<211> LENGTH: 24
<212> TYPE: DNA
<213> ORGANISM: Artificial sequence
<220> FEATURE:
<221> NAME/KEY: source
<222> LOCATION: 1..24
<223> OTHER INFORMATION: /organism="Artificial sequence"
     /note="RLK1 forward primer"
     /mol_type="unassigned DNA"

<400> SEQUENCE: 4

```
ggctggaggc tggagattat ttgg                                              24
```

<210> SEQ ID NO 5
<211> LENGTH: 20
<212> TYPE: DNA
<213> ORGANISM: Artificial sequence
<220> FEATURE:
<221> NAME/KEY: source
<222> LOCATION: 1..20
<223> OTHER INFORMATION: /organism="Artificial sequence"
 /note="RLK1 reverse primer"
 /mol_type="unassigned DNA"

<400> SEQUENCE: 5
aaggcatggt cggtgctatc                                          20

<210> SEQ ID NO 6
<211> LENGTH: 46
<212> TYPE: DNA
<213> ORGANISM: Artificial sequence
<220> FEATURE:
<221> NAME/KEY: source
<222> LOCATION: 1..46
<223> OTHER INFORMATION: /organism="Artificial sequence"
 /note="RLK1 forward reamplification primer"
 /mol_type="unassigned DNA"

<400> SEQUENCE: 6
ggggacaagt ttgtacaaaa aagcaggcta tgagacttta cttatc             46

<210> SEQ ID NO 7
<211> LENGTH: 51
<212> TYPE: DNA
<213> ORGANISM: Artificial sequence
<220> FEATURE:
<221> NAME/KEY: source
<222> LOCATION: 1..51
<223> OTHER INFORMATION: /organism="Artificial sequence"
 /note="RLK1 reverse reamplification primer"
 /mol_type="unassigned DNA"

<400> SEQUENCE: 7
ggggaccact ttgtacaaga aagctgggtt tatttactcc tatcatcgtc g        51

<210> SEQ ID NO 8
<211> LENGTH: 3259
<212> TYPE: DNA
<213> ORGANISM: Arabidopsis thaliana
<220> FEATURE:
<221> NAME/KEY: source
<222> LOCATION: 1..3259
<223> OTHER INFORMATION: /organism="Arabidopsis thaliana"
 /mol_type="unassigned DNA"

<400> SEQUENCE: 8
tagaatttga agaaatcttt gagcaaggag gaaaaaagaa tgagacttta cttatcttca    60
acgatgcagc tttctcttat gagtcttgtt ctagggttcc tctttgtttc ctgtgacgcg   120
tttgcctcta agaaggtat tttgatttct ccatttttctc caattttttgg atgctgagaa   180 agtttagtct tttttagcctc tgtctgttaa cacttgctca ttgagttgat ctagaaagtt   240
agaaacttta gttttgttac tgatcattta gaagtatttg atgttttttgct gttttgtatt   300 cagttgaagc agttagaaga ttcaaggaag ccatttataa ggacccattg ctagttatgt   360
ctaattggaa tgtccccaat ttgagtcctt gtgattggaa tggcattaaa tgttctccat   420
ctaaggatca cattatcaag atgtaggaaa ctttgatctc tttctatcag taaaatcagt   480
tatgtttagt atgatgatga tttggtatct gtttcatgct gtgaaacttg cagaaatata   540

-continued

```
tcggggacat cgatgagagg gtttcttgtg ccagaacttg gtcaaataac ctacttgcaa      600
gaactgtatg gttttgattc atattgacaa tacctgaaga tataagtttg atgattggta      660
ctgtttgtaa atgtttagat gactttgttt tttctgtgtt gaatgcttct ttaggatcct      720
gcgtgggaac attctaatgg ggacaatacc aaaggagata ggaaagttaa agaaactcaa      780
gatcttagac ctgggaaaca atcatttgac aggaccgatt ccagcagaga tcgggaaatt      840
gtcaaggatt aagacaatgt aagaaaatct ttaagagaat gtcatctatc cgataatgtg      900
ctgagataac cattttgtgt ctctttaaca ccacagaaac cttcagtcca atggtttaat      960
aggaaagtta cctccagaga ttggaaactt gaagcacctt aaagaacttc ttattggcag     1020
gaataggctt cgaggaagta ttcctattgc cgcgaaaaca tcaaaaaagt gagtttagct     1080
aatagtccaa ggtagcataa gatggaaact taatgtttat gattgaaatg ttaatgtatc     1140 ttcttttgt gttggtcagg tatgcttcaa atccaagtgc aaacatcagt ggtttgtgca     1200
agtcttctct atttaaagtg gcagatttct cttacaactt tttcgaggga agagttccga     1260
gttgcttgga ttacctccca atgtatttct tataagaccc ttttctagc tttccttat     1320 ttttctcatt tgataatatc tctctgtatc attgaacatc attgtagaac gagcttcaa     1380 ggaaactgca tgaaaaccat ggatgttaag cagagacctc tttcagaatg tggtttgtag     1440
aatatgagtt tcactttctt gatgctgata atcgtttctt tatcttgttt tcattttga     1500 aattgtttca attggttagc tcgcttagct gtaaccgtgg ccaagaagaa gcatcgagca     1560
tcgagacaaa catggcttcg gaattttgag atagtcacgg gatcatcagt tggcttgctc     1620
tttctagtcg taatgttctc tgcatgtagc ttgtgcaaaa taaagcgctc tctcatcgtt     1680
ccctggaaga aatctgcaag tgaaaaggag aagttcacgg tctacgttgg ttagaaactc     1740
ttaaaaattc taagatttca atacaaataa ctgaaagagc ttccagagat gaaaaaatta     1800
ctgataaact gttttttctac agattctgaa atgctgaagg atgtttcaag atatacaaga     1860
caagagctag aagtagcatg tgaagacttc agcaacatca ttgattctag tgcagagagt     1920
cagatttaca aaggaacgat caaaggcggg actgagatcg cggttatctc tctctgcgtt     1980
aaagaagaaa attggactgg atatcttgag cttaatttcc agagagaggt tcttcttctt     2040
atggttgttt atcaccaagt cacttgcaag aaaacatcag tattaaactt gattttatta     2100
atattcattg tttcaggttg cggctttggc tagattaaac catgagaatg cggggaaatt     2160
actgggatac tgtaaagaga gtacaccgtt cacaagaatg cttgtgtttg agtatgcatc     2220
aaacgggaca ctatacgacc atctccactg taatatataa tcaaacttct tcagagctct     2280
ttctttggta ggactgataa tgataccaaa tgatgataaa aatttgatgc agatgcggac     2340
gggagtttag tatcgtgggc aaaacgcatg aaaattgtta taggcatcgc acgtggtctc     2400
aagtaccttc atactgaact ccatcctcca tttacagtct ctgagttgag ctcaactgca     2460
gtgtatctca ctgaagattt tactcccaaa gtaaatttga tcctctttt tctatgcggt     2520 tagctaagct ttgctactat ctctatactc ttatttgat cctcttattt ctatgcagct     2580
ggttgatttc gaatgctgga agattattca ggtgagatca gagaagaacc tgaagaatat     2640
ctgtaatgaa ggagcaatat gtgtacttcc caatgcaatg gaacaccgag atatggattt     2700
acaagggaat atctactcat ttggcatact tttgctggaa attgtaagcg gaagaccttc     2760
ttattgccaa gacagaggtt gcttggttga atgggtaaga atagcttttc tctataagct     2820
taaagctgag tacttataat aagtctctct ctctctctta gcggtttacg tgttttcatg     2880
cgtttgatgc tgaggatttg attcaaactc ctaaatattg caggtaaggg agaaaaacct     2940
```

| | |
|---|---|
| tggtgcacca gatgtgatgg ctagcttggt ggatcctgag ctcaagcatt tcaagcaaaa | 3000 |
| agaacttgag gcagtatgtg aagtggcaag ccaatgtctg aacttggacc agaatgaaaa | 3060 |
| agacaaggat aagcttttctt gttcgattca agcgctttgt gagacactag agagtagaat | 3120 |
| cactgtgtcc atttctgcag aattcaaatc gtcttctctg gcgtgggccg agctagcgct | 3180 |
| ggcctcgcct tctaacgaag acgacgatga taggagtaaa taaaattggc tttgttgtta | 3240 |
| tgacattgac atacacttg | 3259 |

<210> SEQ ID NO 9
<211> LENGTH: 1995
<212> TYPE: DNA
<213> ORGANISM: Artificial sequence
<220> FEATURE:
<221> NAME/KEY: source
<222> LOCATION: 1..1995
<223> OTHER INFORMATION: /organism="Artificial sequence"
　　　　/note="A. thaliana RLK1 sequence modified"
　　　　/mol_type="unassigned DNA"

<400> SEQUENCE: 9

| | |
|---|---|
| atgaggctct accttagctc tactatgcag cttagcctga tgagccttgt gctcggattc | 60 |
| ctgttcgtta gttgcgacgc cttcgctagt aaagaggttg aggccgttag gcgttttaaa | 120 |
| gaggctatct ataaggaccc cctcctcgtg atgtctaact ggaacgttcc caaccttagc | 180 |
| ccctgcgact ggaacggtat taagtgctca cctagtaagg atcacattat taagattaac | 240 |
| attagcggca ctagtatgag gggctttatc gtgccagaga tcggtcagat cacctacctt | 300 |
| caagagctga tccttagggg taatatcctg atggctacta tccctaaaga gatcggtaag | 360 |
| cttaagaagc ttaggattct cgacctcggt aacaatcacc tcaccggacc tattccagcc | 420 |
| gagattggta aacttagtag gattaagact attaaccttc agtctaacgg ccttatcggt | 480 |
| aagctcccac cagagattgg taaccttaag caccttaaag agctgctgat cggccgtaat | 540 |
| aggcttaggg gatcagttcc tattgccgct aagactagta agaagtacgc tagtaaccct | 600 |
| agcgctaata ttagtggcct ctgtaagtct agcctgttta aggtggccga ctttagctat | 660 |
| aacttcttcg agggtagagt gcctagctgc cttgattacc tccctatcac tagctttcag | 720 |
| ggcaactgta tgaaaactat ggacgttaag cagaggcccc ttagtgagtg cgctagactt | 780 |
| gctgttaccg tggctaagaa gaagcacagg gctagtaggc aaacctggct taggaacttc | 840 |
| gagatcgtga ccggatctag cgtgggactt cttttccttg tggtgatgtt tagcgcctgc | 900 |
| tcactctgta agattaagcg tagccttatc gtgccctgga gaaaatcagc tagcgagaaa | 960 |
| gaaaagttca ccgtttacgt ggactcagag atgcttaagg acgttagccg ttacactagg | 1020 |
| caagagcttg aagtggcttg cgaggactt agcaatatta tcgactctag cgccgagtct | 1080 |
| cagatctata agggcactat taagggcggc accgagatcg ctgttattag cctttgcgtt | 1140 |
| aaggaagaga actggaccgg ttacctcgag cttaactttc agagggaagt ggctgctctc | 1200 |
| gctaggctta atcacgaaaa cgctggtaag ctcctcggct actgtaaaga gtctaccccc | 1260 |
| ttcactagga tgctcgtgtt cgaatacgct agtaacggca ccctctacga tcaccttcac | 1320 |
| tacgctgacg gatcactcgt tagttgggct aagaggatga gatcgtgat cggaatcgct | 1380 |
| aggggcctta agtaccttca cactgaactt cacccacccct tcaccgttag cgagcttagt | 1440 |
| tctaccgctg tttacctcac cgaggacttc acccctaagc ttgttgattt cgagtgctgg | 1500 |
| aagattattc aggttaggtc agagaagaac cttaagaata tctgtaacga gggcgctatc | 1560 |

-continued

```
tgcgtgctcc ctaacgctat ggaacacagg gatatggacc ttcagggtaa tatctatagc    1620
ttcggaatcc tgctcctcga gatcgttagt ggtaggccta gctactgtca agatagggt     1680 tgccttgttg agtgggttag ggaaaagaac cttggtgctc cagacgtgat ggctagcctt    1740
gttgatccag agcttaagca ctttaagcag aaagaactcg aggccgtgtg cgaagttgct    1800
agtcagtgcc ttaacctcga tcagaacgag aaggataagg ataagcttag ctgctctatt    1860
caggccctct gcgagactct tgagtctagg attaccgtta gtattagcgc cgagtttaag    1920
tctagctcac tcgcttgggc tgagttggct cttgctagtc ctagtaacga ggacgacgac    1980
gataggtcta agtga                                                      1995
```

<210> SEQ ID NO 10
<211> LENGTH: 664
<212> TYPE: PRT
<213> ORGANISM: Artificial sequence
<220> FEATURE:
<223> OTHER INFORMATION: RLK1 protein sequence optimized

<400> SEQUENCE: 10

```
Met Arg Leu Tyr Leu Ser Ser Thr Met Gln Leu Ser Leu Met Ser Leu
1               5                   10                  15

Val Leu Gly Phe Leu Phe Val Ser Cys Asp Ala Phe Ala Ser Lys Glu
            20                  25                  30

Val Glu Ala Val Arg Arg Phe Lys Glu Ala Ile Tyr Lys Asp Pro Leu
        35                  40                  45

Leu Val Met Ser Asn Trp Asn Val Pro Asn Leu Ser Pro Cys Asp Trp
    50                  55                  60

Asn Gly Ile Lys Cys Ser Pro Ser Lys Asp His Ile Ile Lys Ile Asn
65                  70                  75                  80

Ile Ser Gly Thr Ser Met Arg Gly Phe Ile Val Pro Glu Ile Gly Gln
                85                  90                  95

Ile Thr Tyr Leu Gln Glu Leu Ile Leu Arg Gly Asn Ile Leu Met Ala
            100                 105                 110

Thr Ile Pro Lys Glu Ile Gly Lys Leu Lys Lys Leu Arg Ile Leu Asp
        115                 120                 125

Leu Gly Asn Asn His Leu Thr Gly Pro Ile Pro Ala Glu Ile Gly Lys
    130                 135                 140

Leu Ser Arg Ile Lys Thr Ile Asn Leu Gln Ser Asn Gly Leu Ile Gly
145                 150                 155                 160

Lys Leu Pro Pro Glu Ile Gly Asn Leu Lys His Leu Lys Glu Leu Leu
                165                 170                 175

Ile Gly Arg Asn Arg Leu Arg Gly Ser Val Pro Ile Ala Ala Lys Thr
            180                 185                 190

Ser Lys Lys Tyr Ala Ser Asn Pro Ser Ala Asn Ile Ser Gly Leu Cys
        195                 200                 205

Lys Ser Ser Leu Phe Lys Val Ala Asp Phe Ser Tyr Asn Phe Phe Glu
    210                 215                 220

Gly Arg Val Pro Ser Cys Leu Asp Tyr Leu Pro Ile Thr Ser Phe Gln
225                 230                 235                 240

Gly Asn Cys Met Lys Thr Met Asp Val Lys Gln Arg Pro Leu Ser Glu
                245                 250                 255

Cys Ala Arg Leu Ala Val Thr Val Ala Lys Lys Lys His Arg Ala Ser
            260                 265                 270

Arg Gln Thr Trp Leu Arg Asn Phe Glu Ile Val Thr Gly Ser Ser Val
        275                 280                 285
```

-continued

```
Gly Leu Leu Phe Leu Val Val Met Phe Ser Ala Cys Ser Leu Cys Lys
    290                 295                 300

Ile Lys Arg Ser Leu Ile Val Pro Trp Lys Lys Ser Ala Ser Glu Lys
305                 310                 315                 320

Glu Lys Phe Thr Val Tyr Val Asp Ser Glu Met Leu Lys Asp Val Ser
                325                 330                 335

Arg Tyr Thr Arg Gln Glu Leu Glu Val Ala Cys Glu Asp Phe Ser Asn
            340                 345                 350

Ile Ile Asp Ser Ser Ala Glu Ser Gln Ile Tyr Lys Gly Thr Ile Lys
        355                 360                 365

Gly Gly Thr Glu Ile Ala Val Ile Ser Leu Cys Val Lys Glu Asn
    370                 375                 380

Trp Thr Gly Tyr Leu Glu Leu Asn Phe Gln Arg Glu Val Ala Ala Leu
385                 390                 395                 400

Ala Arg Leu Asn His Glu Asn Ala Gly Lys Leu Leu Gly Tyr Cys Lys
                405                 410                 415

Glu Ser Thr Pro Phe Thr Arg Met Leu Val Phe Glu Tyr Ala Ser Asn
            420                 425                 430

Gly Thr Leu Tyr Asp His Leu His Tyr Ala Asp Gly Ser Leu Val Ser
        435                 440                 445

Trp Ala Lys Arg Met Lys Ile Val Ile Gly Ile Ala Arg Gly Leu Lys
    450                 455                 460

Tyr Leu His Thr Glu Leu His Pro Pro Phe Thr Val Ser Glu Leu Ser
465                 470                 475                 480

Ser Thr Ala Val Tyr Leu Thr Glu Asp Phe Thr Pro Lys Leu Val Asp
                485                 490                 495

Phe Glu Cys Trp Lys Ile Ile Gln Val Arg Ser Glu Lys Asn Leu Lys
            500                 505                 510

Asn Ile Cys Asn Glu Gly Ala Ile Cys Val Leu Pro Asn Ala Met Glu
        515                 520                 525

His Arg Asp Met Asp Leu Gln Gly Asn Ile Tyr Ser Phe Gly Ile Leu
    530                 535                 540

Leu Leu Glu Ile Val Ser Gly Arg Pro Ser Tyr Cys Gln Asp Arg Gly
545                 550                 555                 560

Cys Leu Val Glu Trp Val Arg Glu Lys Asn Leu Gly Ala Pro Asp Val
                565                 570                 575

Met Ala Ser Leu Val Asp Pro Glu Leu Lys His Phe Lys Gln Lys Glu
            580                 585                 590

Leu Glu Ala Val Cys Glu Val Ala Ser Gln Cys Leu Asn Leu Asp Gln
        595                 600                 605

Asn Glu Lys Asp Lys Asp Lys Leu Ser Cys Ser Ile Gln Ala Leu Cys
    610                 615                 620

Glu Thr Leu Glu Ser Arg Ile Thr Val Ser Ile Ser Ala Glu Phe Lys
625                 630                 635                 640

Ser Ser Ser Leu Ala Trp Ala Glu Leu Ala Leu Ala Ser Pro Ser Asn
                645                 650                 655

Glu Asp Asp Asp Asp Arg Ser Lys
            660
```

<210> SEQ ID NO 11
<211> LENGTH: 1995
<212> TYPE: DNA
<213> ORGANISM: Artificial Sequence
<220> FEATURE:

<210> NAME/KEY: source
<222> LOCATION: 1..1995
<223> OTHER INFORMATION: /organism="Artificial Sequence"
/note="Nucleotide sequence RLK1, variant 1"
/mol_type="unassigned DNA"

<400> SEQUENCE: 11

```
atgcgcctat atttatcaag tacaatgcaa ttgtcgatga tgagtctggt cttggggttt      60
atgtttgtga gctgtgatgc ttttgcttct aaggaagtcg aagcagtccg acggttcaaa     120
gaagccatat acaaagatcc actacttgta atgtccaatt ggaatgtgcc gaatctgtca     180
ccatgtgatt ggaatggaat caaatgttct ccctcaaaag accatataat caagataaat     240
atctcaggta cgtctatgcg gggattcata gttcccgaaa tcggacaaat aacgtatcta     300
caggaaatga tattgcgcgg gaacattatg atggcaacaa taccaaagga aattggcaaa     360
ctgaaaaaac tccggatcct tgatctgggt aataaccatc tgacagggcc gatccccgca     420
gaaatcggaa agctgtctcg aattaaaacg atcaatttac aatccaatgg tctaattggg     480
aaactcccgc ccgaaatagg caatctaaaa caccttaagg aaatgatgat agggagaaat     540
agattacggg gatcggtacc aatcgccgca aaaacgtcca aaaaatatgc gtccaatccg     600
tcggcgaaca tcagcggtct gtgcaaatcc tcgatgttca aagtcgctga tttctcttac     660
aatttttttg aaggtcgggt cccctcctgt ttggactatc ttccgattac cagtttccaa     720
ggaaattgca tgaagacgat ggatgtaaaa caacgccctt aagtgaatg tgctcggtta     780
gcagtgacgg tagctaaaaa aaaacatcgg gcgtcacggc agacttggct acgtaatttt     840
gaaattgtaa ccggttcttc tgtaggtctt ttgttttttgg tagtgatgtt cagtgcatgt     900
agcctctgca aaatcaaaag atcattgatt gtaccatgga aaagagtgc ctcagaaaag     960
gagaaattta cagtatatgt tgattcagaa atgttaaaag atgtctcaag gtatacccga    1020
caggaactgg aggttgcgtg tgaagatttc tccaacataa tagattcctc tgctgagagc    1080
cagatataca aagggacgat caagggaggt acagaaattg ccgtcatatc actatgtgtc    1140
aaagaagaaa attggactgg ctatctagaa ctgaattttc aaagagaggt cgcggctcta    1200
gccagattga accatgagaa tgcaggaaaa ttactaggtt attgcaagga atccacgcca    1260
tttacacgca tgcttgtctt tgagtatgcg agcaatggga ccctgtatga ccatcttcat    1320
tatgccgatg ggtccttggt aagctgggca aaaagaatga aaattgttat gggatagca    1380
cgaggtctga atatttgca taccgagtta catccccccat ttactgtaag cgaactctcg    1440
agtacggcgg tgtatttaac cgaagatttt accccccaaac tcgtagactt tgaatgttgg    1500
aaaataatcc aagtgcggag tgaaaaaaat ctcaaaaaca tttgcaatga agggcgata    1560
tgtgtcctcc ccaatgcaat ggagcataga gacatggatc ttcaaggtaa catatactcc    1620
tttggcatta tgttgctgga aatagtatct ggacgaccct cctattgcca ggaccgcggc    1680
tgtcttgtag aatgggtacg tgagaaaaat ctaggcgctc ctgatgttat ggcctcacta    1740
gtagaccctg aattaaaaca tttcaaacaa aaggagctgg aagcggtatg tgaggtcgcc    1800
tcccaatgtt taaatctaga ccaaaatgaa aaagacaaag acaaactgtc ctgttcaatc    1860
caagctctgt gtgaaaccct cgagtcgcgg ataacggtat ccatctcggc ggaattcaaa    1920
tctagctcgc tagcctgggc agaaatggcg ttagcgtccc cctccaatga agatgatgac    1980
gacagaagca aataa                                                    1995
```

<210> SEQ ID NO 12
<211> LENGTH: 1995

```
<212> TYPE: DNA
<213> ORGANISM: Artificial Sequence
<220> FEATURE:
<221> NAME/KEY: source
<222> LOCATION: 1..1995
<223> OTHER INFORMATION: /organism="Artificial Sequence"
      /note="Nucleotide sequence RLK1, variant 2"
      /mol_type="unassigned DNA"

<400> SEQUENCE: 12
```

| | | | | | |
|---|---|---|---|---|---|
| atgcgcctat | atctatcatc | gaccatgcaa | ttatcgatga | tgagcctagt | gttgggtttc | 60 |
| atgtttgtga | gttgtgatgc | attcgcatcc | aaggaagtag | aagcagtacg | tcgattcaag | 120 |
| gaagccatct | acaaagatcc | tttgctcgtt | atgtctaact | ggaatgtacc | taatttatcg | 180 |
| ccatgtgact | ggaatggaat | taagtgctct | ccctccaagg | accatatcat | caaaattaat | 240 |
| attagcggta | cgtccatgcg | tggattcatt | gttcctgaaa | taggccaaat | tacgtattta | 300 |
| caggaaatga | tccttagggg | aaatataatg | atggcgacca | tcccaaagga | gatcggtaag | 360 |
| ttaaaaaaat | tacgaatcct | cgatctaggt | aataatcatc | ttacgggacc | tatccctgca | 420 |
| gaaataggca | agctgtcacg | cataaagacg | ataaacttac | aatcgaatgg | gttgatagga | 480 |
| aaactgcccc | ctgaaatcgg | gaatcttaaa | catcttaagg | aaatgatgat | aggaaggaat | 540 |
| cgtttgcggg | gtagtgttcc | gatcgcggca | aagacgtcga | aaaaatatgc | ttcgaatccc | 600 |
| tcagcgaaca | tctccggact | gtgtaaatcg | tctatgttca | aagtagcgga | tttcagttac | 660 |
| aatttctttg | aaggacgagt | accgtcttgt | ctcgactatc | ttccaatcac | ttcattccaa | 720 |
| gggaattgca | tgaagacgat | ggacgtaaaa | caacgtcccc | tatcagaatg | tgcacgtctt | 780 |
| gcggttactg | tcgcaaaaaa | aaaacacagg | gcctcccgtc | aaacctggct | tcggaatttt | 840 |
| gaaattgtca | ctggatctag | tgttgggcta | ctctttcttg | ttgtgatgtt | cagcgcgtgt | 900 |
| tctctgtgca | aaataaagcg | tagcttaatc | gtgccttgga | aaagtcagc | ttccgaaaag | 960 |
| gagaaattta | cggtatatgt | cgatagtgaa | atgctgaaag | atgtaagcag | atatacgcgc | 1020 |
| caggaactag | aagtggcgtg | tgaggatttc | agtaatatta | ttgattcaag | tgcagagtca | 1080 |
| caaatctaca | aaggaactat | caaaggtggg | actgagatag | cggttatctc | gctgtgtgtt | 1140 |
| aaagaggaaa | attggaccgg | atatcttgaa | ctgaacttcc | aacgggaagt | agccgcactc | 1200 |
| gcgaggctaa | accatgagaa | tgctggaaag | ctgcttgggt | attgcaagga | atctactccg | 1260 |
| ttcaccagga | tgttggtctt | tgagtatgcc | tcgaatggca | ccttatatga | tcatcttcat | 1320 |
| tatgccgatg | gctcactcgt | cagttgggca | aaacgaatga | agatagtaat | tggcatagcc | 1380 |
| aggggcttaa | aatatttgca | cacggagctg | catcccccgt | tcacagtcag | tgaactctct | 1440 |
| tccacggccg | tttatttgac | agaagatttt | acgccaaaac | tggtagactt | tgaatgttgg | 1500 |
| aagatcatac | aagttaggtc | agaaaaaaac | ttaaaaaaca | tctgtaatga | aggagccatt | 1560 |
| tgcgtgctac | cgaatgcgat | ggagcataga | gacatggatc | ttcaagggaa | tatatactcc | 1620 |
| tttggcatac | tgctcctcga | gatagtaagc | ggcagaccta | gttattgtca | ggaccggggc | 1680 |
| tgtctagtgg | aatgggtccg | cgaaaaaaac | ttaggcgccc | cagacgtcat | ggcgtctcta | 1740 |
| gtagatccag | agctgaaaca | tttcaaacaa | aaggagctgg | aagctgtttg | tgaggttgcc | 1800 |
| agtcaatgcc | ttaacctcga | ccagaatgaa | aaagacaaag | acaagttatc | ttgttcaata | 1860 |
| caggctcttt | gcgaaacgtt | ggagtcccga | atcactgttt | caatatctgc | agaattcaaa | 1920 |
| agcagcagtc | tcgcgtgggc | tgaaatggcg | cttgcgtcac | cgtcaaatga | agatgacgat | 1980 |
| gaccggtcca | agtga | | | | | 1995 |

<210> SEQ ID NO 13
<211> LENGTH: 1995
<212> TYPE: DNA
<213> ORGANISM: Artificial Sequence
<220> FEATURE:
<221> NAME/KEY: source
<222> LOCATION: 1..1995
<223> OTHER INFORMATION: /organism="Artificial Sequence"
/note="Nucleotide sequence RLK1, variant 3"
/mol_type="unassigned DNA"

<400> SEQUENCE: 13

```
atgcgcctct atttaagctc tacgatgcag cttagtatga tgagccttgt tctcggattc      60
ctgtttgttt cttgtgatgc cttgcagt aaagaagtag aagccgttcg ccgatttaaa       120
gaggctatct acaaggatcc cctactggta atgtcaaact ggaacgttcc caatttgagt    180
ccatgtgact ggaatggcat aaaatgtagc cccagtaaag accacatcat caaaataaat    240
attagtggta caagtatgcg tggctttata gtacccgaaa tcggccagat cacatacctt    300
caagagctga ttttgagagg caacatcatg atggcaacta ttccaaaaga gatcggcaaa    360
ttgaaaaaac tcagaatact ggacctgggt aataaccatc tgaccgggcc tatcccggct    420
gaaatcggaa agctgtcgag gatcaaaact atcaatttgc aatctaacgg ccttatcggt    480
aaactcccgc cggaaattgg caaccttaag caccttaagg aactgatgat cggccgtaat    540
aggcttcgtg gttcagtacc cattgcagcc aagacttcga agaagtacgc ttccaatcca    600
tccgccaaca taagtggact ctgcaagtcc tcgctgttta agtcgcaga cttcagctac    660
aacttttcg aaggcagagt cccaagctgc ctagactatc ttcctatcac tagcttccaa    720
ggcaactgca tgaagaccat ggatgtgaag caacgacccc ttagtgagtg tgctcggttg    780
gctgttactg ttgccaagaa aaagcacagg gccagtcgtc agacctggct aaggaatttt    840
gagattgtca caggatcgag cgtcggcctg ttgtttcttg tggtgatgtt ctcagcatgt    900
tccctctgca aaatcaaacg tagtttaatc gtaccctgga aaaaaagcgc gagtgaaaag    960
gagaaattta ccgtatacgt cgatagcgag atgcttaaag acgtgtcacg gtacactagg   1020
caggaacttg aggtcgcctg tgaggatttc agcaacatta tagatagtag tgcagagtcc   1080
cagatctata aaggcactat caaggggggc acagaaatcg cagtgattag cctctgcgtt   1140
aaagaggaaa attggacggg atatctcgag ctgaactttc aacgcgaggt agctgctctc   1200
gcaaggctca accatgagaa tgccggtaag cttcttggtt attgtaagga atctacaccg   1260
tttaccagga tgctcgtttt cgagtacgct agtaatggaa cgttgtatga ccatctacat   1320
tatgcggacg gctcactcgt ctcatgggcc aaacgtatga agatcgtcat tggaatcgct   1380
cgagggttga aatatctaca taccgaactc caccccacct ttactgtatc agaactgtct   1440
tctacagctg tgtatctgac cgaagacttt acacctaaat tagttgattt cgaatgttgg   1500
aaaataatac aagtgcgttc ggaaaagaat ttaaagaaca tttgtaacga gggagctatc   1560
tgcgtcctac cgaatgctat ggagcatcgg gacatggacc tacaaggtaa catctacagc   1620
tttggaatcc tgctcttaga aattgtttcg ggtaggccta gctattgcca ggacaggggg   1680
tgtttggttg aatgggtacg tgagaaaaat cttgggcgc cagacgtaat ggcgtcgctg   1740
gtagatccag aacttaaaca cttcaagcaa aaggagttag aggctgtttg tgaggtggcg   1800
tcacaatgtc ttaatctcga tcagaacgaa aaagacaaag acaaactgtc gtgcagtatc   1860
caagccttgt gtgaaactct tgagtcacga attactgtta gtatatctgc tgaatttaaa   1920
tctagttcct tggcatgggc agagatggct cttgcatccc ccagtaatga agacgatgat   1980
```
gaccggtcta aatag                                              1995

<210> SEQ ID NO 14
<211> LENGTH: 1995
<212> TYPE: DNA
<213> ORGANISM: Artificial Sequence
<220> FEATURE:
<221> NAME/KEY: source
<222> LOCATION: 1..1995
<223> OTHER INFORMATION: /organism="Artificial Sequence"
      /note="Nucleotide sequence RLK1, variant 4"
      /mol_type="unassigned DNA"

<400> SEQUENCE: 14

| | | |
|---|---|---|
| atgaggctgt acttgagctc tacaatgcaa ctaagcctga tgtcactcgt cttgggatttt | 60 |
| atgtttgtta gctgcgatgc tttcgctagt aaggaggttg aagccgttag acgcttcaaa | 120 |
| gaggctatct ataaggaccc cctactcgtg atgagtaatt ggaatgtgcc caacttatcc | 180 |
| ccttgcgact ggaatggcat caaatgttca ccaagtaaag accacataat taagattaat | 240 |
| ataagtggaa cttcaatgag gggctttatc gtccctgaaa ttggtcagat tacctatctg | 300 |
| caggaaatga tcctgagggg gaacatcctg atggctacca tacctaagga gataggtaag | 360 |
| ctgaagaaac ttcggatact cgacctcggc aataaccatc tcaccgggcc tatccccgcc | 420 |
| gagatcggta agcttagtag gattaaaact ataaatctcc aaagcaatgg cttgatcggt | 480 |
| aagctcccgc cagagatagg taaccttaag catcttaaag agctgatgat aggacgtaat | 540 |
| cgtcttcgtg gatcagttcc cattgccgca aaaacgagta agaagtacgc cagcaaccct | 600 |
| tctgctaaca tcagtggact ctgcaaatct tcactgttta aggttgccga tttctcgtat | 660 |
| aacttttttg agggtcgtgt accaagttgt ctggattacc tcccgatcac ttccttccaa | 720 |
| gggaactgca tgaaaactat ggacgttaaa cagaggccat tgagtgagtg tgccagactt | 780 |
| gccgttaccg tcgcgaagaa gaagcatagg gcaagtaggc aaacctggtt gaggaatttt | 840 |
| gagatcgtca ccggatcttc agtcggacta ctttttcttg tggtcatgtt cagcgcttgc | 900 |
| tcactctgta agattaagcg gtcgcttata gtgccatgga agaaatctgc ttccgaaaaa | 960 |
| gaaaagttca ctgtttacgt ggattctgag atgcttaaag acgtctcccg ttatacgagg | 1020 |
| caggaacttg aagtggcttg cgaagatttc tcaaacatta tcgattcttc ggctgaaagt | 1080 |
| caaatttaca agggcaccat taaggaggc acagaaatcg ctgttatctc gctttgcgtt | 1140 |
| aaggaggaga actggaccgg ttatctcgaa cttaattttc aacgtgaagt ggctgcactc | 1200 |
| gccaggctca atcacgaaaa tgctgggaag ctccttggat attgtaagga atctaccccc | 1260 |
| tttactcgaa tgttagtgtt cgaatacgcg tccaacggta cattatacga tcatcttcac | 1320 |
| tacgctgacg ggtcattggt tagttgggct aagcgaatga aaatcgtaat cggaatagcg | 1380 |
| cggggactga agtatctaca cactgagcta cacccccccat ttacggtgtc tgagcttagt | 1440 |
| agtaccgctg tgtatcttac agaagacttc accccgaaac tcgttgattt cgaatgctgg | 1500 |
| aagataattc aagttcgaag cgagaaaaat cttaaaaata tatgtaatga aggcgctata | 1560 |
| tgcgtgctcc ctaacgctat ggagcatcga gatatggatc tacagggtaa tatctatagt | 1620 |
| tttggtatac tgctcctgga aatcgtttca ggaaggcctt cgtactgtca agacaggggt | 1680 |
| tgccttgttg aatgggtccg ggagaagaac cttggtgctc cagatgtcat ggctagcctc | 1740 |
| gtcgacccgg agcttaagca ctttaagcaa aaagagttgg aggctgtgtg cgaagtggcc | 1800 |
| agtcagtgtc ttaatttgga tcagaacgaa aaggacaaag ataaacttag ctgttctatc | 1860 |

```
caggccttat gtgagactct tgaatcacgt attacagtta gcataagtgc cgagttcaag    1920
tctagttcac tcgcttgggc agaaatggct cttgcttccc caagtaacga ggacgatgac    1980
gataggtcta agtga                                                    1995

<210> SEQ ID NO 15
<211> LENGTH: 1995
<212> TYPE: DNA
<213> ORGANISM: Artificial Sequence
<220> FEATURE:
<221> NAME/KEY: source
<222> LOCATION: 1..1995
<223> OTHER INFORMATION: /organism="Artificial Sequence"
      /note="Nucleotide sequence RLK1, variant 5"
      /mol_type="unassigned DNA"

<400> SEQUENCE: 15
atgaggctct atttatcgtc tactatgcag ctttcaatga tgtcgcttgt tctcggattc      60
ctgttcgtta gttgcgacgc cttcgcgagc aaagaggttg aggccgtaag gcgtttcaag     120
gaagctatct acaaggatcc cctcctcgtg atgagcaatt ggaacgttcc caaccttagt     180
ccctgcgact ggaacggtat caagtgttca cctagtaaag atcacataat taagattaat     240
atttcaggca ctagtatgcg tggctttatc gtgccagaaa tcggtcagat cacctacctt     300
caagaactga tccttagggg aaacattatg atggcgacta taccgaagga gatcggcaaa     360
cttaagaagc ttaggatcct cgatctcggt aataaccacc tcaccggacc aattccagcc     420
gagattggta aactgagtag gatcaaaact attaaccttc agtctaatgg cctcatcggt     480
aagcttccac cagaaattgg taaccttaaa catcttaagg agtgctgat cgggagaaat     540 aggcttaggg gttcagtacc tattgccgct aaaacttcaa agaaatacgc ttctaaccct     600
agcgctaata tcagcggcct atgtaaatcc tcgctgttta aggtggccga ttttagctac     660
aacttcttcg aggggagagt ccccagctgt cttgattatc tgccgatcac ttcatttcaa     720
ggcaactgta tgaaaactat ggacgttaag caaaggcccc ttagtgagtg cgctcgtctt     780
gctgttaccg tggctaaaaa gaagcaccgc gcttctaggc agacctggct taggaacttc     840
gaaatcgtga cgggaagcag cgtcggactt ctattccttg tagtgatgtt tagcgcatgc     900
agcctctgta agatcaagcg tagcctcatt gtaccctgga agaaatcagc tagtgaaaaa     960
gaaaagttta ccgtctatgt ggactcagag atgcttaaag atgttagccg ttacactagg    1020
caagagcttg aagtcgcttg cgaagacttt agtaatatta tcgactcttc ggccgagtca    1080
cagatatata agggaaccat taaaggcggc accgagatag cagtgatttc tctctgcgtt    1140
aaggaagaga actggaccgg ttatctcgag cttaactttc aaagggaagt ggccgctctt    1200
gcgaggctta atcacgaaaa tgctggcaaa ctcttaggct attgtaaaga gtctacccca    1260
ttcactagga tgctcgtctt tgaatatgcg agtaacggca cccttacga ccacttgcac     1320 tacgctgacg gctctttagt tagttgggct aagagaatga agatcgtcat aggcatcgct    1380
aggggcctta agtaccttca tactgagctt cacccgccct tcaccgtttc ggagcttagt    1440
tcgacagctg tttatctcac ggaggatttc accccgaaac ttgttgactt cgagtgttgg    1500
aagattattc aggttagatc agaaaagaac cttaaaaata tctgtaacga gggggctatc    1560
tgtgtgctcc ccaacgctat ggaacaccgc gatatggatc ttcagggtaa tatctattct    1620
ttcggaatca tgctcctgga gattgttagt ggtaggccta gttactgcca agatagggt     1680 tgtctggtag agtgggtgag ggaaaagaac cttggtgctc ccgacgtgat ggctagcctt    1740
gttgatccag aacttaaaca ttttaagcag aaagagctag aggccgtgtg cgaggttgct    1800
```

```
tcacaatgct tgaacctcga ccagaacgaa aaggataaag acaagcttag ctgctctatt    1860
caggctctct gcgagacttt ggaatccagg atcaccgtta gtatcagcgc cgagttcaaa    1920
tctagctcac tggcttgggc tgagttggct cttgctagtc cttctaatga ggacgacgac    1980
gacaggtcta aatga                                                    1995

<210> SEQ ID NO 16
<211> LENGTH: 1995
<212> TYPE: DNA
<213> ORGANISM: Artificial Sequence
<220> FEATURE:
<221> NAME/KEY: source
<222> LOCATION: 1..1995
<223> OTHER INFORMATION: /organism="Artificial Sequence"
      /note="Nucleotide sequence RLK1, variant 6"
      /mol_type="unassigned DNA"

<400> SEQUENCE: 16
atgaggctct accttagctc tactatgcag cttagcatga tgagcctcgt tctcgggttt      60
ctgttcgtca gttgtgacgc ctttgctagt aaagaggttg aggccgtaag gcgttttaaa     120
gaggctatct ataaggaccc gctcctcgta atgtctaact ggaacgttcc caatcttagc     180
ccctgcgatt ggaatggtat taagtgctca ccttcaaaag atcacattat caagattaat     240
attagcggca ctagtatgag gggctttatc gtaccagaga ttggtcaaat cacctacctt     300
caagagctga tacttagggg taacatcctg atggctacta ttcctaaaga gatcggtaaa     360
cttaagaaac ttaggattct cgatctcggt aacaaccacc tcaccggacc tattccagcc     420
gagattggta aacttagtcg gattaagact attaaccttc agtctaacgg ccttatcgga     480
aagctccccc cagagatagg caacctaaag catctgaaag gatgctgat cggccgcaac      540 aggcttaggg gaagtgttcc gattgcggcg aagacgagta aaaaatacgc tagtaaccct     600
agcgccaata ttagtggcct ctgtaaatct agcctgttta aggtagccga tttcagctat     660
aacttcttcg agggtcgcgt gccgtcttgc cttgattacc tccctatcac aagcttttcaa    720 ggcaattgta tgaaaactat ggatgtgaag caacggcccc ttagtgaatg tgccagactt     780
gccgtcactg ttgctaagaa gaagcacagg gcgtctaggc agacctggct taggaacttc     840
gaaatcgtaa ccggatctag cgtgggactt ctgttccttg tggtcatgtt cagcgcctgc     900
tcactctgta aaattaagcg tagcttgatc gtgccctgga aaaatcagc tagcgagaag      960 gaaaagttca ccgtttacgt tgactcagag atgcttaagg acgtgagccg gtacactagg    1020
caagagcttg aagtggcttg tgaagactttt tcaaatatca tcgactctag tgccgagagc    1080
caaatctata agggcaccat taagggcgga acggagattg ctgttatctc tttgtgtgtt    1140
aaggaggaaa attggaccgg ttacctcgag ttgaacttcc agagggaagt agctgctctc    1200
gctaggctta accacgagaa cgccggaaag ctcctgggct actgtaaaga atcgaccccc    1260
ttcactagga tgctcgtgtt cgagtatgct agtaacggca cactctacga ccatctgcac    1320
tacgctgacg gatcattagt tagttgggcg aagcggatga aaattgtgat tggaatcgct    1380
cgaggcctga agtaccttca cactgaactt cacccaccgt tcaccgttag cgaacttagt    1440
tctaccgctg tttacctgac agaggacttc accccctaagc ttgttgactt cgagtgctgg    1500
aaaattattc aggttaggtc agagaagaac cttaagaata tctgtaacga gggtgctatc    1560
tgcgtcctcc ctaacgccat ggaacatagg gacatggatc ttcagggtaa tatctacagc    1620
tttggaatca tgctccttga gatcgttagt ggtaggccta gctattgcca agacagggt    1680
```

-continued

```
tgtcttgttg agtgggttag ggaaaaaaac cttggagctc cagacgtgat ggcttccctg    1740
gttgatccag agcttaagca ctttaagcag aaagaactcg aggccgtgtg cgaagtggct    1800
tcacagtgcc ttaacctcga tcagaacgag aaggataagg ataagttgag ctgctctatt    1860
caggcactct gcgagacgct tgagtctcgc attaccgtga gtattagcgc agagtttaag    1920
tctagctcac tcgcatgggc tgagttggct cttgctagtc ctagtaacga ggacgacgac    1980
gacaggtcta aatga                                                     1995
```

<210> SEQ ID NO 17
<211> LENGTH: 1995
<212> TYPE: DNA
<213> ORGANISM: Artificial Sequence
<220> FEATURE:
<221> NAME/KEY: source
<222> LOCATION: 1..1995
<223> OTHER INFORMATION: /organism="Artificial Sequence"
    /note="Nucleotide sequence RLK1, variant 7"
    /mol_type="unassigned DNA"

<400> SEQUENCE: 17

```
atgcgactct accttagctc gactatgcag cttagcctga tgagcttggt gttaggattc      60
ctgttcgtaa gttgcgacgc cttcgctagt aaagaggttg aagccgttag cgttttaaa     120 gaagctatct ataaggatcc tctcctcgtg atgtctaact ggaacgttcc taatcttagc     180
ccctgcgatt ggaacggtat taagtgctca cctagtaagg atcacattat aaagattaac     240
attagcggca ctagtatgag gggttttatc gtgccagaga ttggtcagat cacctacctt     300
caggagctga tccttagggg taatattctg atggctacta ttcctaaaga gatcggtaag     360
cttaagaagc ttaggatact cgacctcggt aacaatcacc tcaccggacc tattccggcc     420
gagattggta aacttagtag gattaaaacg attaaccttc agtctaacgg ccttataggt     480
aaactcccac cagaaattgg taaccttaag caccttaaag agatgctgat cggccgtaac     540
aggcttaggg ggtccgttcc tattgctgct aagactagta agaagtacgc tagtaaccct     600
tccgctaata ttagtggcct ctgtaaatct agcctgttca aggtcgccga cttcagctat     660
aacttcttcg agggtagagt gcccagctgc cttgactatc tccctatcac tagcttttcag    720 ggcaactgta tgaaaactat ggacgttaag cagaggcccc ttagtgagtg tgctagactt     780
gctgttaccg tggcgaagaa aaagcatcga gcttcgaggc aaacctggtt aaggaacttt     840
gagatcgtga ccggatctag cgtgggactt cttttccttg tcgtgatgtt tagcgcctgc     900
tcactctgca agatcaagcg ttctcttatc gtgccctgga aaaaatcagc tagcgagaaa     960
gaaaagttca ccgtttatgt ggactcagag atgcttaagg acgttagccg ttacactagg    1020
caagaacttg aagtggcttg cgaggatttt agcaatatta tcgactctag cgccgagtct    1080
cagatctaca agggcactat taagggaggc acagaaatcg ctgttattag cctttgcgtt    1140
aaggaagaga actggaccgg atacttggag cttaactttc aaagggaagt ggctgctctc    1200
gctcgcctta atcacgaaaa cgctggtaag ctcctcggct actgtaaaga gtctaccct     1260 ttcactagga tgctcgtttt tgaatacgcc tcgaacggca ccctgtacga tcaccttcat    1320
tacgctgatg gttcactcgt ttcgtgggct aagaggatga agatcgtgat cggaatagct    1380
cgtggcctta agtaccttca tactgaactt cacccaccgt tcaccgttag cgagcttagt    1440
tctaccgctg tttacctaac cgaggacttc accctaagc ttgttgattt cgagtgttgg     1500
aaaattattc aggttaggtc agagaaaaat cttaagaata tctgtaatga gggcgctata    1560
tgcgtgctcc ctaacgctat ggaacacagg gatatggacc ttcagggtaa catctatagc    1620
```

```
ttcggaatcc tgctcctcga gatcgttagt ggtaggccta gctactgcca agatagaggt    1680
tgccttgtgg agtgggttag ggaaaagaac cttggtgctc cagacgtgat ggctagcctt    1740
gttgatccag agcttaaaca cttttaagcag aaagaactcg aggccgtgtg cgaagtagct   1800
agtcagtgtc ttaacctcga tcagaacgaa aaggataagg ataagcttag ctgctctatt    1860
caggccctct gcgagactct tgagtcaagg attacggtta gtatttcggc cgagttcaaa    1920
agcagctcac tcgcttgggc tgagttggct cttgctagtc ctagtaacga ggatgacgac    1980
gaccgctcta agtga                                                     1995
```

<210> SEQ ID NO 18
<211> LENGTH: 1995
<212> TYPE: DNA
<213> ORGANISM: Artificial Sequence
<220> FEATURE:
<221> NAME/KEY: source
<222> LOCATION: 1..1995
<223> OTHER INFORMATION: /organism="Artificial Sequence"
       /note="Nucleotide sequence RLK1, variant 8"
       /mol_type="unassigned DNA"

<400> SEQUENCE: 18

```
atgaggctct accttagctc tacaatgcag cttagcctga tgagccttgt gctcggattc    60
atgttcgtta gttgcgacgc cttcgctagt aaggaggttg aggccgttag gcgttttaaa    120
gaggctatct ataaggaccc cctcctcgtg atgtctaact ggaacgttcc caaccttagc    180
ccctgcgact ggaacggtat taagtgctca cctagtaagg atcacattat taagattaac    240
attagcggca ctagtatgag gggctttatc gtgccagaga tcggtcagat cacctactta    300
caagagctga tacttagggg taatatcctg atggctacaa tccctaaaga gatcggaaag    360
ttgaagaagc ttaggattct cgacctcggt aacaatcacc tcaccggacc tattccagcc    420
gagatcggaa aacttagtag gattaagact attaaccttc agtccaacgg ccttatcggc    480
aagctcccac cagagatcgg taaccttaaa caccttaaag agctgctgat cggccgtaat    540
aggcttagag gatcagttcc tattgccgct aagactagta agaagtacgc cagtaaccct    600
agcgctaata ttagtggcct ctgtaagtct agcatgttta aggtggccga ctttagctac    660
aacttcttcg agggtagagt gcctagctgc cttgactacc tccctatcac tagctttcag    720
ggcaactgta tgaaaactat ggatgttaag cagaggcctc ttagtgagtg tgctagactt    780
gctgttaccg tggctaaaaa gaagcacagg gctagtaggc aaacctggct aaggaacttc    840
gagatcgtaa ccggatctag cgtgggactg ctttttcctcg tggtgatgtt tagcgcctgc    900
tcactctgta agattaagcg tagccttatc gtgccctgga agaagtcagc tagcgagaaa    960
gaaaagttta ccgtttacgt ggactcagag atgcttaagg acgttagccg ttacactagg    1020
caagaacttg aagtggcttg cgaggacttt agcaatatta tcgactctag cgcggagtct    1080
cagatctata agggcactat tagggggggc accgagatcg ctgttattag cctttgcgtt    1140
aaggaagaga actggaccgg gtacctcgag cttaactttc agagggaagt agctgctctc    1200
gctcgactta atcacgaaaa cgctggtaag ctcctcggct actgtaagga gtctaccccc    1260
ttcactagga tgctcgtctt cgaatatgcc agtaacggca ccctctacga tcaccttcac    1320
tacgctgacg gatcactcgt tagttgggct aagcgcatga agattgtgat cggaatcgct    1380 agggggcctta agtaccttca cactgaactg caccccaccct tcaccgttag cgagcttagt    1440
tctaccgctg tttacctcac cgaggacttc acccctaagt tagttgattt cgagtgctgg    1500
```

```
aagattattc aggttaggtc agagaaaaac cttaagaata tctgtaacga aggcgctatc    1560
tgcgtgctcc ctaacgctat ggaacaccga gatatggact tacagggtaa catctattcc    1620
ttcggaatcc tgttgttgga aatcgttagt ggtcgtccta gctactgcca agatagggggt   1680 tgccttgtgg agtgggttag ggaaaagaac cttggtgctc cagacgtgat ggctagcctg    1740
gttgatccag agcttaagca ttttaagcag aaagaactcg aggccgtgtg cgaagttgct    1800
agtcagtgcc ttaacctcga tcagaacgag aaggataagg ataagcttag ctgctctatt    1860
caggccttgt gcgagactct tgagtctagg attaccgtta gtattagcgc cgagttcaag    1920
tcgagctcac tcgcttgggc tgagttggct cttgctagtc ctagtaacga ggacgacgac    1980
gataggtcta agtga                                                     1995

<210> SEQ ID NO 19
<211> LENGTH: 1992
<212> TYPE: DNA
<213> ORGANISM: Artificial Sequence
<220> FEATURE:
<221> NAME/KEY: source
<222> LOCATION: 1..1992
<223> OTHER INFORMATION: /organism="Artificial Sequence"
      /note="Nucleotide sequence RLK1, variant 9"
      /mol_type="unassigned DNA"

<400> SEQUENCE: 19
atgagactgt acctgagcag caccatgcag ctgagcctga tgagcctggt gctgggcttc      60
ctgttcgtga gctgcgacgc cttcgccagc aaggaggtgg aggccgtgag aagattcaag     120
gaggccatct acaaggaccc cctgctggtg atgagcaact ggaacgtgcc caacctgagc     180
ccctgcgact ggaacggcat caagtgcagc cccagcaagg accacatcat caagatcaac     240
atcagcggca ccagcatgag aggcttcatc gtgcccgaga tcggccagat cacctacctg     300
caggagctga tcctgagagg caacatcctg atggccacca tccccaagga gatcggcaag     360
ctgaagaagc tgagaatcct ggacctgggc aacaaccacc tgaccggccc catccccgcc     420
gagatcggca agctgagcag aatcaagacc atccagctgc agtgcaacgc cctgctggcc     480
cacgcccccc ccgagggcgg ccaggtgaag cacctgagag agctgctgat cctgagacag     540
cacctgcacc tgagcatccc cgtggtggcc agatgcagca agagatacgc cagccagccc     600
agcctgcagc tgtgcgtgct gtgcaagtgc agcgcctgga gctggccgga ctggagcttc     660
aactacttcg acggccacgg ccccagctgc ggcgactacc tgcccgcctg ctgctaccag     720
ggccagaccg tgcacaccat ggagctgaag aaccacccc tgagcgagtg catcagactg      780
gtggtgagcg tggccaagaa gagaaagcac gcctgcagac agaccttcgt gaagaactgg     840
gacatcgtgt gcggcagctg cgtgggcgcc ctgttcggcg tggccatgtg gaccatgtgc     900
agcatgtgcc acggcaagaa gagcgtgatc atcccctgga agaagagcat cagcgacaga     960
gacagatgga ccctgttcat ggacaccgag atgctgaagg acgtgagcag atacaccaga    1020
caggagctgg aggtggcctg cgaggacttc agcaacatca tcgacagcag cgccgagagc    1080
cagatctaca agggcaccat caagggcggc accgagatcg ccgtgatcag cctgtgcgtg    1140
aaggaggacc agttcagcgg ctacatggag gtgaactggc agagagacgg catggtggcc    1200
gccagaggcc agcacgagca gatgatccac ctgctgggct acaccaagga gaccagcccc    1260
ttcaccaagg ccctggtgtt cgagtacgcc tgccagggca gcctgttcga ccacatcaga    1320
tggatcgacg gctgcctggc cagctgggtg aagaaggtga agctggtgat gggcgccgcc    1380
agaatcgcca gatacctgca ctgcgacgtg aagccccct tcagcggctg cgagctgacc    1440
```

-continued

```
tgcagcgcca tctacgccag cgaggactac accccccacg ccgtggacta cgagtgcttc    1500
aagatcgcca acgtgcacag cgacaagaac atgagacaga tcacccagga cggcctgatc    1560
tgcgtgctgc ccaacgccat ggagcacaga gacatggacc tgcagggcaa catctacagc    1620
ttcggcatcc tgctgctgga gatcgtgagc ggcagaccca gctactgcca ggacagaggc    1680
tgcctggtgg agtgggtgag agagaagaac ctgggcgccc ccgacgtgat ggccagcctg    1740
gtggagcccg agatgaagag ataccaccag cacgagctgg agatggccag cgacggcgcc    1800
agccagtgcc tgaacatgga ccagaacgac aaggagcacg agagactgtg cagcagcatc    1860
caggccctgt gcgagaccct ggagagcaga ctgagcgtgt gcatcagcct ggactaccac    1920
agcaccagcg ccgtgtgggt ggagggcgcc gtgctgaccc ccagccagga ggacgaggac    1980
gagagaagca ga                                                       1992
```

<210> SEQ ID NO 20
<211> LENGTH: 664
<212> TYPE: PRT
<213> ORGANISM: Artificial Sequence
<220> FEATURE:
<223> OTHER INFORMATION: Amino acid sequence RLK1, variant 9

<400> SEQUENCE: 20

```
Met Arg Leu Tyr Leu Ser Ser Thr Met Gln Leu Ser Leu Met Ser Leu
1               5                   10                  15

Val Leu Gly Phe Leu Phe Val Ser Cys Asp Ala Phe Ala Ser Lys Glu
            20                  25                  30

Val Glu Ala Val Arg Arg Phe Lys Glu Ala Ile Tyr Lys Asp Pro Leu
        35                  40                  45

Leu Val Met Ser Asn Trp Asn Val Pro Asn Leu Ser Pro Cys Asp Trp
    50                  55                  60

Asn Gly Ile Lys Cys Ser Pro Ser Lys Asp His Ile Ile Lys Ile Asn
65                  70                  75                  80

Ile Ser Gly Thr Ser Met Arg Gly Phe Ile Val Pro Glu Ile Gly Gln
                85                  90                  95

Ile Thr Tyr Leu Gln Glu Leu Ile Leu Arg Gly Asn Ile Leu Met Ala
            100                 105                 110

Thr Ile Pro Lys Glu Ile Gly Lys Leu Lys Lys Leu Arg Ile Leu Asp
        115                 120                 125

Leu Gly Asn Asn His Leu Thr Gly Pro Ile Pro Ala Glu Ile Gly Lys
    130                 135                 140

Leu Ser Arg Ile Lys Thr Ile Gln Leu Gln Cys Asn Ala Leu Leu Ala
145                 150                 155                 160

His Ala Pro Pro Glu Gly Gly Gln Val Lys His Leu Arg Glu Leu Leu
                165                 170                 175

Ile Leu Arg Gln His Leu His Leu Ser Ile Pro Val Val Ala Arg Cys
            180                 185                 190

Ser Lys Arg Tyr Ala Ser Gln Pro Ser Leu Gln Leu Cys Val Leu Cys
        195                 200                 205

Lys Cys Ser Ala Trp Lys Leu Ala Asp Trp Ser Phe Asn Tyr Phe Asp
    210                 215                 220

Gly His Gly Pro Ser Cys Gly Asp Tyr Leu Pro Ala Cys Cys Tyr Gln
225                 230                 235                 240

Gly Gln Thr Val His Thr Met Glu Leu Lys Asn His Pro Leu Ser Glu
                245                 250                 255
```

-continued

```
Cys Ile Arg Leu Val Val Ser Val Ala Lys Lys Arg Lys His Ala Cys
            260                 265                 270

Arg Gln Thr Phe Val Lys Asn Trp Asp Ile Val Cys Gly Ser Cys Val
            275                 280                 285

Gly Ala Leu Phe Gly Val Ala Met Trp Thr Met Cys Ser Met Cys His
            290                 295                 300

Gly Lys Lys Ser Val Ile Ile Pro Trp Lys Lys Ser Ile Ser Asp Arg
305                 310                 315                 320

Asp Arg Trp Thr Leu Phe Met Asp Thr Glu Met Leu Lys Asp Val Ser
                325                 330                 335

Arg Tyr Thr Arg Gln Glu Leu Glu Val Ala Cys Glu Asp Phe Ser Asn
            340                 345                 350

Ile Ile Asp Ser Ser Ala Glu Ser Gln Ile Tyr Lys Gly Thr Ile Lys
            355                 360                 365

Gly Gly Thr Glu Ile Ala Val Ile Ser Leu Cys Val Lys Glu Asp Gln
370                 375                 380

Phe Ser Gly Tyr Met Glu Val Asn Trp Gln Arg Asp Gly Met Val Ala
385                 390                 395                 400

Ala Arg Gly Gln His Glu Gln Met Ile His Leu Leu Gly Tyr Thr Lys
                405                 410                 415

Glu Thr Ser Pro Phe Thr Lys Ala Leu Val Phe Glu Tyr Ala Cys Gln
            420                 425                 430

Gly Ser Leu Phe Asp His Ile Arg Trp Ile Asp Gly Cys Leu Ala Ser
            435                 440                 445

Trp Val Lys Lys Val Lys Leu Val Met Gly Ala Ala Arg Ile Ala Arg
450                 455                 460

Tyr Leu His Cys Asp Val Lys Pro Pro Phe Ser Gly Cys Glu Leu Thr
465                 470                 475                 480

Cys Ser Ala Ile Tyr Ala Ser Glu Asp Tyr Thr Pro His Ala Val Asp
                485                 490                 495

Tyr Glu Cys Phe Lys Ile Ala Asn Val His Ser Asp Lys Asn Met Arg
            500                 505                 510

Gln Ile Thr Gln Asp Gly Leu Ile Cys Val Leu Pro Asn Ala Met Glu
            515                 520                 525

His Arg Asp Met Asp Leu Gln Gly Asn Ile Tyr Ser Phe Gly Ile Leu
530                 535                 540

Leu Leu Glu Ile Val Ser Gly Arg Pro Ser Tyr Cys Gln Asp Arg Gly
545                 550                 555                 560

Cys Leu Val Glu Trp Val Arg Glu Lys Asn Leu Gly Ala Pro Asp Val
                565                 570                 575

Met Ala Ser Leu Val Glu Pro Glu Met Lys Arg Tyr His Gln His Glu
            580                 585                 590

Leu Glu Met Ala Ser Asp Gly Ala Ser Gln Cys Leu Asn Met Asp Gln
            595                 600                 605

Asn Asp Lys Glu His Glu Arg Leu Cys Ser Ser Ile Gln Ala Leu Cys
610                 615                 620

Glu Thr Leu Glu Ser Arg Leu Ser Val Cys Ile Ser Leu Asp Tyr His
625                 630                 635                 640

Ser Thr Ser Ala Val Trp Val Glu Gly Ala Val Leu Thr Pro Ser Gln
                645                 650                 655

Glu Asp Glu Asp Glu Arg Ser Arg
            660
```

```
<210> SEQ ID NO 21
<211> LENGTH: 1992
<212> TYPE: DNA
<213> ORGANISM: Artificial Sequence
<220> FEATURE:
<221> NAME/KEY: source
<222> LOCATION: 1..1992
<223> OTHER INFORMATION: /organism="Artificial Sequence"
      /note="Nucleotide sequence RLK1, variant 10"
      /mol_type="unassigned DNA"

<400> SEQUENCE: 21
atgagactgt acctgagcag caccatgcag ctgagcctga tgagcctggt gctgggcttc      60
ctgttcgtga gctgcgacgc cttcgccagc aaggaggtgg aggccgtgag aagattcaag     120
gaggccatct acaaggaccc cctgctggtg atgagcaact ggaacgtgcc caacctgagc     180
ccctgcgact ggaacggcat caagtgcagc cccagcaagg accacatcat caagatcaac     240
atcagcggca ccagcatgag aggcttcatc gtgcccgaga tcggccagat cacctacctg     300
caggagctga tcctgagagg caacatcctg atggccacca tccccaagga gatcggcaag     360
ctgaagaagc tgagaatcct ggacctgggc aacaaccacc tgaccggccc catccccgcc     420
gagatcggca agctgagcag aatcaagacc atccaggtgc agacccaggg cctggccggc     480
aagatgcccc ccgagatcgg caacggcaga cacgtgagag atgggcgc cggcagacag       540 aaggtgagag caccctgcc catcgtggcc aagtgctgca gaagattcgc caccaacccc      600
agcggccaga tgagcggcct gtgcagaacc agcctgttca agatcggcga ctggtgcttc     660
aacttcttcg agatgaaggt gcccacctgc ctggactggc tgcccggcac cagcttcaac     720
ggcaacagcc tgaagaccgg cgaggtgaag aacagacccc tgtgcgactg cgccagactg     780
gccatctgcg tgatgcacaa gaagcacaga ggcagcagaa acagctggct gaagaactgg     840
gacatcatga ccggcaccac catgggcggc ctgttcatgg tggtgatgtt caccgccacc     900
agcggctgcc acatcaagag aagcatcctg tgccctgga gagaagcgc ctgcgacaag       960 gagcacttct gcatctacct ggacaccgag atgctgaagg acgtgagcag atacaccaga    1020
caggagctgg aggtggcctg cgaggacttc agcaacatca tcgacagcag cgccgagagc    1080
cagatctaca gggcaccat caagggcggc accgagatcg ccgtgatcag cctgtgcgtg     1140
aaggacgaga ctggaccgg ctacctggac gtgaacttcc agagagacgt ggccatcctg     1200
ggcagaggcc agcacgacca ggccgtgcac ctgggcatct tcagccacga gtgcacccc    1260 ttcaccagaa tcggcggctt cgagtacgcc agccagggca ccctgttcga gagactgcac    1320
ttcgccgacc tgagcatggt gagctgggtg aagcacctga gctggccat cggcatcgcc    1380 agagccatga gtacgccca ccgaggcc agacccccct tcaccgtgag cgacgccagc       1440
accaccgtgg tgtacctgac cgacgacttc tgcccccacc tggtggactt cgagtgcttc    1500
aagatcatca acgtgagaag cgacaagcag gccaagaaca tcacccagga gggcgccatc    1560
tgcgtgctgc ccaacgccat ggagcacaga gacatggacc tgcagggcaa catctacagc    1620
ttcggcatcc tgctgctgga gatcgtgagc ggcagaccca gctactgcca ggacagaggc    1680
tgcctggtgg agtgggtgag agagaagaac ctgggcgccc ccgacgtgat ggccagcctg    1740
gtggagcccg acctgagaag attcaagcag cacgagctgg aggccctgtg cgaggtgggc    1800
acccagtgcg ccaacatgga ccagaacgag aaggagagag agagaggcac ctgcaccctg    1860
cagatcctgt gcgactgcct ggagaccaag atcaccgtga gcatcagcgc cgagtggaag    1920
agcaccagcg gcgcctggct ggagctggcc atcatcaccc ccagcaacga ggacgacgac    1980
```
gaccacagca ag                                                             1992

<210> SEQ ID NO 22
<211> LENGTH: 664
<212> TYPE: PRT
<213> ORGANISM: Artificial Sequence
<220> FEATURE:
<223> OTHER INFORMATION: Amino acid sequence RLK1, variant 10

<400> SEQUENCE: 22

```
Met Arg Leu Tyr Leu Ser Ser Thr Met Gln Leu Ser Leu Met Ser Leu
1               5                   10                  15

Val Leu Gly Phe Leu Phe Val Ser Cys Asp Ala Phe Ala Ser Lys Glu
            20                  25                  30

Val Glu Ala Val Arg Arg Phe Lys Glu Ala Ile Tyr Lys Asp Pro Leu
        35                  40                  45

Leu Val Met Ser Asn Trp Asn Val Pro Asn Leu Ser Pro Cys Asp Trp
    50                  55                  60

Asn Gly Ile Lys Cys Ser Pro Ser Lys Asp His Ile Ile Lys Ile Asn
65                  70                  75                  80

Ile Ser Gly Thr Ser Met Arg Gly Phe Ile Val Pro Glu Ile Gly Gln
                85                  90                  95

Ile Thr Tyr Leu Gln Glu Leu Ile Leu Arg Gly Asn Ile Leu Met Ala
            100                 105                 110

Thr Ile Pro Lys Glu Ile Gly Lys Leu Lys Leu Arg Ile Leu Asp
        115                 120                 125

Leu Gly Asn Asn His Leu Thr Gly Pro Ile Pro Ala Glu Ile Gly Lys
    130                 135                 140

Leu Ser Arg Ile Lys Thr Ile Gln Val Gln Thr Gln Gly Leu Ala Gly
145                 150                 155                 160

Lys Met Pro Pro Glu Ile Gly Asn Gly Arg His Val Arg Glu Met Gly
                165                 170                 175

Ala Gly Arg Gln Lys Val Arg Gly Thr Leu Pro Ile Val Ala Lys Cys
            180                 185                 190

Cys Arg Arg Phe Ala Thr Asn Pro Ser Gly Gln Met Ser Gly Leu Cys
        195                 200                 205

Arg Thr Ser Leu Phe Lys Ile Gly Asp Trp Cys Phe Asn Phe Phe Glu
    210                 215                 220

Met Lys Val Pro Thr Cys Leu Asp Trp Leu Pro Gly Thr Ser Phe Asn
225                 230                 235                 240

Gly Asn Ser Leu Lys Thr Gly Glu Val Lys Asn Arg Pro Leu Cys Asp
                245                 250                 255

Cys Ala Arg Leu Ala Ile Cys Val Met His Lys Lys His Arg Gly Ser
            260                 265                 270

Arg Asn Ser Trp Leu Lys Asn Trp Asp Ile Met Thr Gly Thr Thr Met
        275                 280                 285

Gly Gly Leu Phe Met Val Met Phe Thr Ala Thr Ser Gly Cys His
    290                 295                 300

Ile Lys Arg Ser Ile Leu Val Pro Trp Lys Arg Ser Ala Cys Asp Lys
305                 310                 315                 320

Glu His Phe Cys Ile Tyr Leu Asp Thr Glu Met Leu Lys Asp Val Ser
                325                 330                 335

Arg Tyr Thr Arg Gln Glu Leu Glu Val Ala Cys Glu Asp Phe Ser Asn
            340                 345                 350

Ile Ile Asp Ser Ser Ala Glu Ser Gln Ile Tyr Lys Gly Thr Ile Lys
```

```
                      355                 360                 365
Gly Gly Thr Glu Ile Ala Val Ile Ser Leu Cys Val Lys Asp Glu Asn
              370                 375                 380

Trp Thr Gly Tyr Leu Asp Val Asn Phe Gln Arg Asp Val Ala Ile Leu
385                 390                 395                 400

Gly Arg Gly Gln His Asp Gln Ala Val His Leu Gly Ile Phe Ser His
              405                 410                 415

Glu Cys Thr Pro Phe Thr Arg Ile Gly Gly Phe Glu Tyr Ala Ser Gln
              420                 425                 430

Gly Thr Leu Phe Glu Arg Leu His Phe Ala Asp Leu Ser Met Val Ser
              435                 440                 445

Trp Val Lys His Leu Lys Leu Ala Ile Gly Ile Ala Arg Ala Met Lys
              450                 455                 460

Tyr Ala His Thr Glu Ala Arg Pro Pro Phe Thr Val Ser Asp Ala Ser
465                 470                 475                 480

Thr Thr Val Val Tyr Leu Thr Asp Asp Phe Cys Pro His Leu Val Asp
              485                 490                 495

Phe Glu Cys Phe Lys Ile Ile Asn Val Arg Ser Asp Lys Gln Ala Lys
              500                 505                 510

Asn Ile Thr Gln Glu Gly Ala Ile Cys Val Leu Pro Asn Ala Met Glu
              515                 520                 525

His Arg Asp Met Asp Leu Gln Gly Asn Ile Tyr Ser Phe Gly Ile Leu
              530                 535                 540

Leu Leu Glu Ile Val Ser Gly Arg Pro Ser Tyr Cys Gln Asp Arg Gly
545                 550                 555                 560

Cys Leu Val Glu Trp Val Arg Glu Lys Asn Leu Gly Ala Pro Asp Val
              565                 570                 575

Met Ala Ser Leu Val Glu Pro Asp Leu Arg Arg Phe Lys Gln His Glu
              580                 585                 590

Leu Glu Ala Leu Cys Glu Val Gly Thr Gln Cys Ala Asn Met Asp Gln
              595                 600                 605

Asn Glu Lys Glu Arg Glu Arg Gly Thr Cys Thr Leu Gln Ile Leu Cys
              610                 615                 620

Asp Cys Leu Glu Thr Lys Ile Thr Val Ser Ile Ser Ala Glu Trp Lys
625                 630                 635                 640

Ser Thr Ser Gly Ala Trp Leu Glu Leu Ala Ile Ile Thr Pro Ser Asn
              645                 650                 655

Glu Asp Asp Asp Asp His Ser Lys
              660

<210> SEQ ID NO 23
<211> LENGTH: 1992
<212> TYPE: DNA
<213> ORGANISM: Artificial Sequence
<220> FEATURE:
<221> NAME/KEY: source
<222> LOCATION: 1..1992
<223> OTHER INFORMATION: /organism="Artificial Sequence"
      /note="Nucleotide sequence RLK1, variant 11"
      /mol_type="unassigned DNA"

<400> SEQUENCE: 23
atgagactgt acctgagcag caccatgcag ctgagcctga tgagcctggt gctgggcttc      60
ctgttcgtga gctgcgacgc cttcgccagc aaggaggtgg aggccgtgag aagattcaag     120
gaggccatct acaaggaccc cctgctggtg atgagcaact ggaacgtgcc caacctgagc     180
```

```
ccctgcgact ggaacggcat caagtgcagc cccagcaagg accacatcat caagatcaac      240
atcagcggca ccagcatgag aggcttcatc gtgcccgaga tcggccagat cacctacctg      300
caggagctga tcctgagagg caacatcctg atggccacca tccccaagga gatcggcaag      360
ctgaagaagc tgagaatcct ggacctgggc aacaaccacc tgaccggccc catccccgcc      420
gagatcggca agctgagcag aatcaagacc atccagctgc agacccaggt ggccatcatc      480
aagctgcccc ccgaggccgg caacctgaag cacctgagag aggtgctggt gggcaagcag      540
cacgtgagag gcagcgtgcc catcctggcc agaaccagca gaagtacgc ctgcaacccc       600 accgccaaca tcagcatgct gtgcaagagc accctgttca gagtgatgga gttcacctac      660
cagttctggg agggcaaggt gcccagctgc ctggactacg cccccatcac cacctggcag      720
ggcaacacca tcaagaccat ggaggtgcac aaccaccccc tgtgcgagtg cgccagactg      780
gccatgagcg gcgccaagaa gaagcacaga atcacccacc agacctggat gcacaacttc      840
gagatcgtga ccgccagcag cctgggcctg gctacctgg tgatcatgtt cagcgcctgc      900
accctgtgca agatcaagag aagcggcatc gtgcccctgga agaagagcat cagcgagaag     960
gaccacttca ccgtgtacgt ggacaccgag atgctgaagg acgtgagcag atacaccaga     1020
caggagctgg aggtggcctg cgaggacttc agcaacatca tcgacagcag cgccgagagc     1080
cagatctaca agggcaccat caagggcggc accgagatcg ccgtgatcag cctgtgcgtg     1140
aaggaggagc agtacaccgg ctacctggag ggcaacttcc agagagagat cgccatgctg     1200
atcagactga ccacgacca gctggtgaag ctgctgggct actgcaagga gagcaccccc     1260
ttcagcagag ccctgatgtt cgagtacgcc agcaacggca gctgtggga ccacatgcac      1320 tacatcgacg gcagcctggt gagctacgcc aagaagctga agatcgtgct gggcatcgcc     1380
agagccctgc acttcgccca caccgaggg aagcccccct acagcgtgag cgagatgagc      1440
agcaccgccg gctacctgac cgaggactttc agcccagag ccggcgactt cgagtgctgg     1500
aagatcgtgc agatccacac cgagaagcag ctgaagcaga tctgcaacga gctggccatc     1560
tgcgtgctgc ccaacgccat ggagcacaga gacatggacc tgcagggcaa catctacagc     1620
ttcggcatcc tgctgctgga gatcgtgagc ggcagaccca gctactgcca ggacagaggc     1680
tgcctggtgg agtgggtgag agaagaaac ctgggcgccc ccgacgtgat ggccagcctg      1740
gtggagcccg agatgagaa gttcaagcag cacgagctgg aggccgtgag cgacgtggcc     1800
agccagtgcc tgcagctgga gaacaacgac aaggacaagg accacgtgag cagcagcatc     1860
aacctgctga gcgagtgcat cgacaccaga atctgcgtga gcatcagcgc cgagttcaga     1920
agcagctgca tcgcctgggc cgagctggtg atggccagcc ccaccaacga ggacgacgac     1980
gaccactgca ag                                                         1992

<210> SEQ ID NO 24
<211> LENGTH: 664
<212> TYPE: PRT
<213> ORGANISM: Artificial Sequence
<220> FEATURE:
<223> OTHER INFORMATION: Amino acid sequence RLK1, variant 11

<400> SEQUENCE: 24

Met Arg Leu Tyr Leu Ser Ser Thr Met Gln Leu Ser Leu Met Ser Leu
1               5                   10                  15

Val Leu Gly Phe Leu Phe Val Ser Cys Asp Ala Phe Ala Ser Lys Glu
            20                  25                  30

Val Glu Ala Val Arg Arg Phe Lys Glu Ala Ile Tyr Lys Asp Pro Leu
```

```
            35                  40                  45
Leu Val Met Ser Asn Trp Asn Val Pro Asn Leu Ser Pro Cys Asp Trp
 50                  55                  60

Asn Gly Ile Lys Cys Ser Pro Ser Lys Asp His Ile Ile Lys Ile Asn
 65                  70                  75                  80

Ile Ser Gly Thr Ser Met Arg Gly Phe Ile Val Pro Glu Ile Gly Gln
                 85                  90                  95

Ile Thr Tyr Leu Gln Glu Leu Ile Leu Arg Gly Asn Ile Leu Met Ala
            100                 105                 110

Thr Ile Pro Lys Glu Ile Gly Lys Leu Lys Lys Leu Arg Ile Leu Asp
            115                 120                 125

Leu Gly Asn Asn His Leu Thr Gly Pro Ile Pro Ala Glu Ile Gly Lys
130                 135                 140

Leu Ser Arg Ile Lys Thr Ile Gln Leu Gln Thr Gln Val Ala Ile Ile
145                 150                 155                 160

Lys Leu Pro Pro Glu Ala Gly Asn Leu Lys His Leu Arg Glu Val Leu
                165                 170                 175

Val Gly Lys Gln His Val Arg Gly Ser Val Pro Ile Leu Ala Arg Thr
            180                 185                 190

Ser Lys Lys Tyr Ala Cys Asn Pro Thr Ala Asn Ile Ser Met Leu Cys
            195                 200                 205

Lys Ser Thr Leu Phe Arg Val Met Glu Phe Thr Tyr Gln Phe Trp Glu
210                 215                 220

Gly Lys Val Pro Ser Cys Leu Asp Tyr Gly Pro Ile Thr Thr Trp Gln
225                 230                 235                 240

Gly Asn Thr Ile Lys Thr Met Glu Val His Asn His Pro Leu Cys Glu
                245                 250                 255

Cys Ala Arg Leu Ala Met Ser Gly Ala Lys Lys His Arg Ile Thr
            260                 265                 270

His Gln Thr Trp Met His Asn Phe Glu Ile Val Thr Ala Ser Ser Leu
            275                 280                 285

Gly Leu Gly Tyr Leu Val Ile Met Phe Ser Ala Cys Thr Leu Cys Lys
290                 295                 300

Ile Lys Arg Ser Gly Ile Val Pro Trp Lys Lys Ser Ile Ser Glu Lys
305                 310                 315                 320

Asp His Phe Thr Val Tyr Val Asp Thr Glu Met Leu Lys Asp Val Ser
                325                 330                 335

Arg Tyr Thr Arg Gln Glu Leu Glu Val Ala Cys Glu Asp Phe Ser Asn
            340                 345                 350

Ile Ile Asp Ser Ser Ala Glu Ser Gln Ile Tyr Lys Gly Thr Ile Lys
            355                 360                 365

Gly Gly Thr Glu Ile Ala Val Ile Ser Leu Cys Val Lys Glu Glu Gln
            370                 375                 380

Tyr Thr Gly Tyr Leu Glu Gly Asn Phe Gln Arg Glu Ile Ala Met Leu
385                 390                 395                 400

Ile Arg Leu Asn His Asp Gln Leu Val Lys Leu Leu Gly Tyr Cys Lys
                405                 410                 415

Glu Ser Thr Pro Phe Ser Arg Ala Leu Met Phe Glu Tyr Ala Ser Asn
            420                 425                 430

Gly Ser Leu Trp Asp His Met His Tyr Ile Asp Gly Ser Leu Val Ser
            435                 440                 445

Tyr Ala Lys Lys Leu Lys Ile Val Leu Gly Ile Ala Arg Ala Leu His
450                 455                 460
```

```
Phe Ala His Thr Glu Gly Lys Pro Pro Tyr Ser Val Ser Glu Met Ser
465                 470                 475                 480

Ser Thr Ala Gly Tyr Leu Thr Glu Asp Phe Ser Pro Arg Ala Gly Asp
            485                 490                 495

Phe Glu Cys Trp Lys Ile Val Gln Ile His Thr Glu Lys Gln Leu Lys
        500                 505                 510

Gln Ile Cys Asn Glu Leu Ala Ile Cys Val Leu Pro Asn Ala Met Glu
            515                 520                 525

His Arg Asp Met Asp Leu Gln Gly Asn Ile Tyr Ser Phe Gly Ile Leu
530                 535                 540

Leu Leu Glu Ile Val Ser Gly Arg Pro Ser Tyr Cys Gln Asp Arg Gly
545                 550                 555                 560

Cys Leu Val Glu Trp Val Arg Glu Lys Asn Leu Gly Ala Pro Asp Val
                565                 570                 575

Met Ala Ser Leu Val Glu Pro Glu Met Arg Lys Phe Lys Gln His Glu
            580                 585                 590

Leu Glu Ala Val Ser Asp Val Ala Ser Gln Cys Leu Gln Leu Glu Asn
            595                 600                 605

Asn Asp Lys Asp Lys Asp His Val Ser Ser Ile Asn Leu Leu Ser
610                 615                 620

Glu Cys Ile Asp Thr Arg Ile Cys Val Ser Ile Ser Ala Glu Phe Arg
625                 630                 635                 640

Ser Ser Cys Ile Ala Trp Ala Glu Leu Val Met Ala Ser Pro Thr Asn
                645                 650                 655

Glu Asp Asp Asp Asp His Cys Lys
            660

<210> SEQ ID NO 25
<211> LENGTH: 1992
<212> TYPE: DNA
<213> ORGANISM: Artificial Sequence
<220> FEATURE:
<221> NAME/KEY: source
<222> LOCATION: 1..1992
<223> OTHER INFORMATION: /organism="Artificial Sequence"
      /note="Nucleotide sequence RLK1, variant 12"
      /mol_type="unassigned DNA"

<400> SEQUENCE: 25
atgagactgt acctgagcag caccatgcag ctgagcctga tgagcctggt gctgggcttc      60
ctgttcgtga gctgcgacgc cttcgccagc aaggaggtgg aggccgtgag aagattcaag     120
gaggccatct acaaggaccc cctgctggtg atgagcaact ggaacgtgcc caacctgagc     180
ccctgcgact ggaacggcat caagtgcagc cccagcaagg accacatcat caagatcaac     240
atcagcggca ccagcatgag aggcttcatc gtgcccgaga tcggccagat cacctacctg     300
caggagctga tcctgagagg caacatcctg atgccaccca tccccaagga gatcggcaag     360
ctgaagaagc tgagaatcct ggacctgggc aacaaccacc tgaccggccc catccccgcc     420
gagatcggca agctgagcag aatcaagacc atcaacctgc agtgcaacct gggcatcatc     480
aagctgcccc ccgacatcgg ccagatcaag cacctgaagg acctgctgat gctgcacaac     540
agactgagag gcagcgtgcc catcgccgcc aagaccagca gaagtacat gagccagccc     600 agcgccaaca tcagcgccct gtgcaagtgc tgcctgttca gagtggccga gttctgctac     660
aacttcttcg agggcagagt gcccagcagc ctggactacc tgcccatgag cagctaccag     720
ggcaactgca tgaagaccat ggacgccaag cagagacccc tgagcgactg cgccagaatc     780
```

```
gccggcaccg tggccaagaa gaagcacaga gccagccacc agacctggct gagaaacttc    840
gagatcgtga gcggcagcag cgtgggcctg ctgttcatcg tggtgatgtg gagcgcctgc    900
agcctgtgca agatcaagag aagcctgatc gtgcccttca agaagcgc cagcgagaag      960
gagaagtgga gcctgtacgt ggacaccgag atgctgaagg acgtgagcag atacaccaga    1020
caggagctgg aggtggcctg cgaggacttc agcaacatca tcgacagcag cgccgagagc    1080
cagatctaca agggcaccat caagggcggc accgagatcg ccgtgatcag cctgtgcgtg    1140
aaggaggagc agtggaccat ctacctggag gccaacttca acagagaggt ggccgccctg    1200
gccagactga accacgagca ggccgcccac ctgctgggct actgcaagga gaccaccccc    1260
ttcacccaca tgctggtgtt cgagtacgcc agcaacggca ccctgtacga caagctgaga    1320
tacgccgacg gcaccggcgt gacctgggcc aagagaatgc acatggtgat catcgtggcc    1380
agaggcctga agtacctgca caccgagatg cacccccccct ggtgcgtgag cgagatctgc    1440
tgcagcgccg tgtacctgac cgaggagttc accccccaaga tcgccgagta cgagtgctgg    1500
aagatcatca acgtgagaag cgagaagaac ctgaagaacg gctgcaacga gggcgccatc    1560
tgcgtgctgc ccaacgccat ggagcacaga gacatggacc tgcagggcaa catctacagc    1620
ttcggcatcc tgctgctgga gatcgtgagc ggcagaccca gctactgcca ggacagaggc    1680
tgcctggtgg agtgggtgag agagaagaac ctgggcgccc ccgacgtgat ggccagcctg    1740
gtggagcccg agctgaagca cttcaagcag aaggagctgg aggccgtgac cgacatcgcc    1800
agcaactgcc tgaacgccga ccagaacgac cacgagaagg acaagatgag ctgcaccatc    1860
cagatgctgt gcgacaccct ggagacccac atcagcgtgt gcatcagcgc cgagttcaag    1920
agcagcagcg tggtgtgggc cgagggcgcc ggcgccagcc ccagccagga cgacgaggac    1980
gacagaagca ag                                                        1992
```

<210> SEQ ID NO 26
<211> LENGTH: 664
<212> TYPE: PRT
<213> ORGANISM: Artificial Sequence
<220> FEATURE:
<223> OTHER INFORMATION: Amino acid sequence RLK1, variant 12

<400> SEQUENCE: 26

```
Met Arg Leu Tyr Leu Ser Ser Thr Met Gln Leu Ser Leu Met Ser Leu
1               5                   10                  15

Val Leu Gly Phe Leu Phe Val Ser Cys Asp Ala Phe Ala Ser Lys Glu
            20                  25                  30

Val Glu Ala Val Arg Arg Phe Lys Glu Ala Ile Tyr Lys Asp Pro Leu
        35                  40                  45

Leu Val Met Ser Asn Trp Asn Val Pro Asn Leu Ser Pro Cys Asp Trp
    50                  55                  60

Asn Gly Ile Lys Cys Ser Pro Ser Lys Asp His Ile Ile Lys Ile Asn
65                  70                  75                  80

Ile Ser Gly Thr Ser Met Arg Gly Phe Ile Val Pro Glu Ile Gly Gln
                85                  90                  95

Ile Thr Tyr Leu Gln Glu Leu Ile Leu Arg Gly Asn Ile Leu Met Ala
            100                 105                 110

Thr Ile Pro Lys Glu Ile Gly Lys Leu Lys Lys Leu Arg Ile Leu Asp
        115                 120                 125

Leu Gly Asn Asn His Leu Thr Gly Pro Ile Pro Ala Glu Ile Gly Lys
    130                 135                 140
```

```
Leu Ser Arg Ile Lys Thr Ile Asn Leu Gln Cys Asn Leu Gly Ile Ile
145                 150                 155                 160

Lys Leu Pro Pro Asp Ile Gly Gln Ile Lys His Leu Lys Asp Leu Leu
                165                 170                 175

Met Leu His Asn Arg Leu Arg Gly Ser Val Pro Ile Ala Ala Lys Thr
            180                 185                 190

Ser Lys Lys Tyr Met Ser Gln Pro Ser Ala Asn Ile Ser Ala Leu Cys
        195                 200                 205

Lys Cys Cys Leu Phe Arg Val Ala Glu Phe Cys Tyr Asn Phe Phe Glu
210                 215                 220

Gly Arg Val Pro Ser Ser Leu Asp Tyr Leu Pro Met Ser Ser Tyr Gln
225                 230                 235                 240

Gly Asn Cys Met Lys Thr Met Asp Ala Lys Gln Arg Pro Leu Ser Asp
                245                 250                 255

Cys Ala Arg Ile Ala Gly Thr Val Ala Lys Lys His Arg Ala Ser
            260                 265                 270

His Gln Thr Trp Leu Arg Asn Phe Glu Ile Val Ser Gly Ser Ser Val
        275                 280                 285

Gly Leu Leu Phe Ile Val Val Met Trp Ser Ala Cys Ser Leu Cys Lys
290                 295                 300

Ile Lys Arg Ser Leu Ile Val Pro Phe Arg Arg Ser Ala Ser Glu Lys
305                 310                 315                 320

Glu Lys Trp Ser Leu Tyr Val Asp Thr Glu Met Leu Lys Asp Val Ser
                325                 330                 335

Arg Tyr Thr Arg Gln Glu Leu Glu Val Ala Cys Glu Asp Phe Ser Asn
            340                 345                 350

Ile Ile Asp Ser Ser Ala Glu Ser Gln Ile Tyr Lys Gly Thr Ile Lys
        355                 360                 365

Gly Gly Thr Glu Ile Ala Val Ile Ser Leu Cys Val Lys Glu Glu Gln
370                 375                 380

Trp Thr Ile Tyr Leu Glu Ala Asn Phe Asn Arg Glu Val Ala Ala Leu
385                 390                 395                 400

Ala Arg Leu Asn His Glu Gln Ala Ala His Leu Leu Gly Tyr Cys Lys
                405                 410                 415

Glu Thr Thr Pro Phe Thr His Met Leu Val Phe Glu Tyr Ala Ser Asn
            420                 425                 430

Gly Thr Leu Tyr Asp Lys Leu Arg Tyr Ala Asp Gly Thr Gly Val Thr
        435                 440                 445

Trp Ala Lys Arg Met His Met Val Ile Val Ala Arg Gly Leu Lys
450                 455                 460

Tyr Leu His Thr Glu Met His Pro Pro Trp Cys Val Ser Glu Ile Cys
465                 470                 475                 480

Cys Ser Ala Val Tyr Leu Thr Glu Glu Phe Thr Pro Lys Ile Ala Glu
                485                 490                 495

Tyr Glu Cys Trp Lys Ile Ile Asn Val Arg Ser Glu Lys Asn Leu Lys
            500                 505                 510

Asn Gly Cys Asn Glu Gly Ala Ile Cys Val Leu Pro Asn Ala Met Glu
        515                 520                 525

His Arg Asp Met Asp Leu Gln Gly Asn Ile Tyr Ser Phe Gly Ile Leu
    530                 535                 540

Leu Leu Glu Ile Val Ser Gly Arg Pro Ser Tyr Cys Gln Asp Arg Gly
545                 550                 555                 560
```

```
Cys Leu Val Glu Trp Val Arg Glu Lys Asn Leu Gly Ala Pro Asp Val
                565                 570                 575

Met Ala Ser Leu Val Glu Pro Glu Leu Lys His Phe Lys Gln Lys Glu
            580                 585                 590

Leu Glu Ala Val Thr Asp Ile Ala Ser Asn Cys Leu Asn Ala Asp Gln
        595                 600                 605

Asn Asp His Glu Lys Asp Lys Met Ser Cys Thr Ile Gln Met Leu Cys
    610                 615                 620

Asp Thr Leu Glu Thr His Ile Ser Val Cys Ile Ser Ala Glu Phe Lys
625                 630                 635                 640

Ser Ser Ser Val Val Trp Ala Glu Gly Ala Gly Ala Ser Pro Ser Gln
                645                 650                 655

Asp Asp Glu Asp Asp Arg Ser Lys
            660

<210> SEQ ID NO 27
<211> LENGTH: 1992
<212> TYPE: DNA
<213> ORGANISM: Artificial Sequence
<220> FEATURE:
<221> NAME/KEY: source
<222> LOCATION: 1..1992
<223> OTHER INFORMATION: /organism="Artificial Sequence"
      /note="Nucleotide sequence RLK1, variant 13"
      /mol_type="unassigned DNA"

<400> SEQUENCE: 27
atgagactgt acctgagcag caccatgcag ctgagcctga tgagcctggt gctgggcttc      60
ctgttcgtga gctgcgacgc cttcgccagc aaggaggtgg aggccgtgag aagattcaag     120
gaggccatct acaaggaccc cctgctggtg atgagcaact ggaacgtgcc caacctgagc     180
ccctgcgact ggaacggcat caagtgcagc cccagcaagg accacatcat caagatcaac     240
atcagcggca ccagcatgag aggcttcatc gtgcccgaga tcggccagat cacctacctg     300
caggagctga tcctgagagg caacatcctg atggccacca tccccaagga gatcggcaag     360
ctgaagaagc tgagaatcct ggacctgggc aacaaccacc tgaccggccc catccccgcc     420
gagatcggca agctgagcag aatcaagacc atcaacctgc agagcaacgg cctgatcggc     480
aagctgcccc ccgagatcgg ccagctgaag cacctgaagg agctgctgat cgccaagaac     540
agactgagag gctgcgtgcc catcggcgcc aagaccagag aagtacgc cac caaccccc     600 agcgccaaca tcagcgtgct gtgcaagagc acc ctgttca ggtggtgga cttcagctac     660 aacttcttcg agggcagagt gcccagcacc ctggactacc tgcccatcac ctgcttccag     720
ggcaactgca tgaagaccat ggacgtgaag cagcaccccc tgagcgagtg cgccagagtg     780
gccgtgaccc tggccaagaa gaagcacaga gccagcagac agagctggct gagaaacttc     840
gagatcgtga ccggctgcag cgtgggcctg ctgtggctgc tgatcatgtt cagcgcctgc     900
agcctgtgca agatcaagaa gagcctgatc gtgcccttca gaagagcat cagcgagcac     960 gagaagttca ccgtgtacgt ggacagcgag atgctgaagg acgtgagcag atacaccaga    1020
caggagctgg aggtggcctg cgaggacttc agcaacatca tcgacagcag cgccgagagc    1080
cagatctaca agggcaccat caagggcggc accgagatcg ccgtgatcag cctgtgcgtg    1140
aaggaggaga actggtgcgg ctggatcgag ctgaacttcc agagagaggt ggccgccctg    1200
gccagactga accacgacaa cgccggcaag ctgctgggct actgcaagga gagctgcccc    1260
ttcagcagaa tcctgctgtt cgactacatg agcaacggca ccatctacga gcacatccac    1320
```

```
tacgccgagc tgagcgccgt gagctgggcc aagagaatga agatcgtgat gggcatcctg    1380
cacggcctga agtacctgca cagcgagctg aagcccccct tcaccgtgtg cgagctgagc    1440
agcaccgccg gctacctgac cgaggacttc accccaagg  ccgtggactt cgagtgctgg    1500
aagatcatcc aggtgagaag cgagaagaac ctgagaaaca tctgccagga ggccgccatc    1560
tgcgtgctgc ccaacgccat ggagcacaga gacatggacc tgcagggcaa catctacagc    1620
ttcggcatcc tgctgctgga gatcgtgagc ggcagaccca gctactgcca ggacagaggc    1680
tgcctggtgg agtgggtgag agagaagaac ctgggcgccc ccgacgtgat ggccagcctg    1740
gtggaccccg agctgcacca cttcaagcag aaggagctgg aggccgtgtg cgagctggcc    1800
agccagtgcc tgaacctgga caacaacgag aaggagaagg acaagctgag ctgcagcatc    1860
caggccctgt gcgagaccct ggagagccac atcagcgtga gcatgagcgc cgagttcaag    1920
agctgcagcc tgatgtgggc cgagatcgcc gtggccagcc ccagcaacga ggacgacgac    1980
gaccacacca ag                                                       1992
```

<210> SEQ ID NO 28
<211> LENGTH: 664
<212> TYPE: PRT
<213> ORGANISM: Artificial Sequence
<220> FEATURE:
<223> OTHER INFORMATION: Amino acid sequence RLK1, variant 13

<400> SEQUENCE: 28

```
Met Arg Leu Tyr Leu Ser Ser Thr Met Gln Leu Ser Leu Met Ser Leu
1               5                   10                  15

Val Leu Gly Phe Leu Phe Val Ser Cys Asp Ala Phe Ala Ser Lys Glu
            20                  25                  30

Val Glu Ala Val Arg Arg Phe Lys Glu Ala Ile Tyr Lys Asp Pro Leu
        35                  40                  45

Leu Val Met Ser Asn Trp Asn Val Pro Asn Leu Ser Pro Cys Asp Trp
    50                  55                  60

Asn Gly Ile Lys Cys Ser Pro Ser Lys Asp His Ile Ile Lys Ile Asn
65                  70                  75                  80

Ile Ser Gly Thr Ser Met Arg Gly Phe Ile Val Pro Glu Ile Gly Gln
                85                  90                  95

Ile Thr Tyr Leu Gln Glu Leu Ile Leu Arg Gly Asn Ile Leu Met Ala
            100                 105                 110

Thr Ile Pro Lys Glu Ile Gly Lys Leu Lys Lys Leu Arg Ile Leu Asp
        115                 120                 125

Leu Gly Asn Asn His Leu Thr Gly Pro Ile Pro Ala Glu Ile Gly Lys
    130                 135                 140

Leu Ser Arg Ile Lys Thr Ile Asn Leu Gln Ser Asn Gly Leu Ile Gly
145                 150                 155                 160

Lys Leu Pro Pro Glu Ile Gly Gln Leu Lys His Leu Lys Glu Leu Leu
                165                 170                 175

Ile Ala Lys Asn Arg Leu Arg Gly Cys Val Pro Ile Gly Ala Lys Thr
            180                 185                 190

Ser Lys Lys Tyr Ala Thr Asn Pro Ser Ala Asn Ile Ser Val Leu Cys
        195                 200                 205

Lys Ser Thr Leu Phe Lys Val Val Asp Phe Ser Tyr Asn Phe Phe Glu
    210                 215                 220

Gly Arg Val Pro Ser Thr Leu Asp Tyr Leu Pro Ile Thr Cys Phe Gln
225                 230                 235                 240
```

```
Gly Asn Cys Met Lys Thr Met Asp Val Lys Gln His Pro Leu Ser Glu
                245                 250                 255

Cys Ala Arg Val Ala Val Thr Leu Ala Lys Lys His Arg Ala Ser
        260                 265                 270

Arg Gln Ser Trp Leu Arg Asn Phe Glu Ile Val Thr Gly Cys Ser Val
        275                 280                 285

Gly Leu Leu Trp Leu Leu Ile Met Phe Ser Ala Cys Ser Leu Cys Lys
        290                 295                 300

Ile Lys Lys Ser Leu Ile Val Pro Phe Lys Lys Ser Ile Ser Glu His
305                 310                 315                 320

Glu Lys Phe Thr Val Tyr Val Asp Ser Glu Met Leu Lys Asp Val Ser
                325                 330                 335

Arg Tyr Thr Arg Gln Glu Leu Glu Val Ala Cys Glu Asp Phe Ser Asn
            340                 345                 350

Ile Ile Asp Ser Ser Ala Glu Ser Gln Ile Tyr Lys Gly Thr Ile Lys
            355                 360                 365

Gly Gly Thr Glu Ile Ala Val Ile Ser Leu Cys Val Lys Glu Asn
        370                 375                 380

Trp Cys Gly Trp Ile Glu Leu Asn Phe Gln Arg Glu Val Ala Ala Leu
385                 390                 395                 400

Ala Arg Leu Asn His Asp Asn Ala Gly Lys Leu Leu Gly Tyr Cys Lys
                405                 410                 415

Glu Ser Cys Pro Phe Ser Arg Ile Leu Leu Phe Asp Tyr Met Ser Asn
            420                 425                 430

Gly Thr Ile Tyr Glu His Ile His Tyr Ala Glu Leu Ser Ala Val Ser
            435                 440                 445

Trp Ala Lys Arg Met Lys Ile Val Met Gly Ile Leu His Gly Leu Lys
        450                 455                 460

Tyr Leu His Ser Glu Leu Lys Pro Pro Phe Thr Val Cys Glu Leu Ser
465                 470                 475                 480

Ser Thr Ala Gly Tyr Leu Thr Glu Asp Phe Thr Pro Lys Ala Val Asp
                485                 490                 495

Phe Glu Cys Trp Lys Ile Ile Gln Val Arg Ser Glu Lys Asn Leu Arg
            500                 505                 510

Asn Ile Cys Gln Glu Ala Ala Ile Cys Val Leu Pro Asn Ala Met Glu
        515                 520                 525

His Arg Asp Met Asp Leu Gln Gly Asn Ile Tyr Ser Phe Gly Ile Leu
        530                 535                 540

Leu Leu Glu Ile Val Ser Gly Arg Pro Ser Tyr Cys Gln Asp Arg Gly
545                 550                 555                 560

Cys Leu Val Glu Trp Val Arg Glu Lys Asn Leu Gly Ala Pro Asp Val
                565                 570                 575

Met Ala Ser Leu Val Asp Pro Glu Leu His Phe Lys Gln Lys Glu
            580                 585                 590

Leu Glu Ala Val Cys Glu Leu Ala Ser Gln Cys Leu Asn Leu Asp Asn
            595                 600                 605

Asn Glu Lys Glu Lys Asp Lys Leu Ser Cys Ser Ile Gln Ala Leu Cys
        610                 615                 620

Glu Thr Leu Glu Ser His Ile Ser Val Ser Met Ser Ala Glu Phe Lys
625                 630                 635                 640

Ser Cys Ser Leu Met Trp Ala Glu Ile Ala Val Ala Ser Pro Ser Asn
                645                 650                 655

Glu Asp Asp Asp Asp His Thr Lys
```

```
                660
```

<210> SEQ ID NO 29
<211> LENGTH: 1992
<212> TYPE: DNA
<213> ORGANISM: Artificial Sequence
<220> FEATURE:
<221> NAME/KEY: source
<222> LOCATION: 1..1992
<223> OTHER INFORMATION: /organism="Artificial Sequence"
      /note="Nucleotide sequence RLK1, variant 14"
      /mol_type="unassigned DNA"

<400> SEQUENCE: 29

```
atgagactgt acctgagcag caccatgcag ctgagcctga tgagcctggt gctgggcttc      60
ctgttcgtga gctgcgacgc cttcgccagc aaggaggtgg aggccgtgag aagattcaag     120
gaggccatct acaaggaccc cctgctggtg atgagcaact ggaacgtgcc caacctgagc     180
ccctgcgact ggaacggcat caagtgcagc cccagcaagg accacatcat caagatcaac     240
atcagcggca ccagcatgag aggcttcatc gtgcccgaga tcggccagat cacctacctg     300
caggagctga tcctgagagg caacatcctg atggccacca tccccaagga gatcggcaag     360
ctgaagaagc tgagaatcct ggacctgggc aacaaccacc tgaccggccc catccccgcc     420
gagatcggca agctgagcag aatcaagacc atcaacctgc agagcaacgg cctgatcggc     480
aagctgcccc ccgagatcgg caacctgaag agactgaagg acctgctgat cggcagaaac     540
agactgagaa tcagcgtgcc catcgccgcc aagaccagca gaagtacgc cagcaacccc     600
agcgccaaca tcagcggcct gtgcaagagc agcggctgga aggtgctgga cttctgctac     660
aactggttcg agggcagagt gcccagctgc ctggactacc tgcccatcac cagcttccag     720
ggcaactgca tgaagagcat ggacgtgaag cagcaccccca tgagcgagtg cgcccacctg     780
gccgtgaccg tggccaagaa gaagcacaga gccagcagac agagctggct gagaaactac     840
gagatcgtga ccggcagcag cgtgggcctg ctgttcctgg tggtgatgtt cagcgcctgc     900
agcctgtgca agatcaagag aagcctgatc gtgccctgga agaagagcgc cagcgacaag     960
gacaagttca ccgtgtacgt ggagaccgag atgctgaagg acgtgagcag atacaccaga    1020
caggagctgg aggtggcctg cgaggacttc agcaacatca tcgacagcag cgccgagagc    1080
cagatctaca agggcaccat caagggcggc accgagatcg ccgtgatcag cctgtgcgtg    1140
aaggacgaga actggaccgg ctacctggag ctgaacttcc agagagagct ggccgccctg    1200
atgaagctga ccacgagaa cgccggcaag ctgctgggct actgcaagga gaccacccc    1260
ttcaccagaa tggtggtgtt cgactacggc agcaacgtga ccctgtacga gcacctgcac    1320
tacgtggacg gcagcatcgt gagcttcgtg aagaaggcca aggccgtgat cggcggcgcc    1380
aagggcctga agtacctgca caccgagctg cacccccct tcaccgtgag cgagctgagc    1440
agcaccgccg tgtacctgac cgaggacttc agccccaagc tggtggactg ggagagctgg    1500
aagatcatcc aggtgagaac cgagaagaac ctgaagaaca tctgcaacga gggcgccatc    1560
tgcgtgctgc ccaacgccat ggagcacaga gacatggacc tgcagggcaa catctacagc    1620
ttcggcatcc tgctgctgga gatcgtgagc ggcagaccca gctactgcca ggacagaggc    1680
tgcctggtgg agtgggtgag agagaagaac ctgggcgccc ccgacgtgat ggccagcctg    1740
gtggaccccg agctgaagaa gtggaagcag aaggacctgg aggccgtgtg cgaggtgatg    1800
agccagtgcc tgaacctgga ccagaacgag aaggacaagg acaagatcag ctgcagcatc    1860
caggccctgt gcgagaccct ggagtgcaga atcaccatga gcatcagcgc cgagttcaag    1920
```
agcagcagcc tgatctggct ggagctggcc ctgatgagcc ccagcaacga ggacgacgac    1980
gagagaagca ag    1992

<210> SEQ ID NO 30
<211> LENGTH: 664
<212> TYPE: PRT
<213> ORGANISM: Artificial Sequence
<220> FEATURE:
<223> OTHER INFORMATION: Amino acid sequence RLK1, variant 14

<400> SEQUENCE: 30

Met Arg Leu Tyr Leu Ser Ser Thr Met Gln Leu Ser Leu Met Ser Leu
1               5                   10                  15

Val Leu Gly Phe Leu Phe Val Ser Cys Asp Ala Phe Ala Ser Lys Glu
            20                  25                  30

Val Glu Ala Val Arg Arg Phe Lys Glu Ala Ile Tyr Lys Asp Pro Leu
        35                  40                  45

Leu Val Met Ser Asn Trp Asn Val Pro Asn Leu Ser Pro Cys Asp Trp
    50                  55                  60

Asn Gly Ile Lys Cys Ser Pro Ser Lys Asp His Ile Ile Lys Ile Asn
65                  70                  75                  80

Ile Ser Gly Thr Ser Met Arg Gly Phe Ile Val Pro Glu Ile Gly Gln
                85                  90                  95

Ile Thr Tyr Leu Gln Glu Leu Ile Leu Arg Gly Asn Ile Leu Met Ala
            100                 105                 110

Thr Ile Pro Lys Glu Ile Gly Lys Leu Lys Lys Leu Arg Ile Leu Asp
        115                 120                 125

Leu Gly Asn Asn His Leu Thr Gly Pro Ile Pro Ala Glu Ile Gly Lys
    130                 135                 140

Leu Ser Arg Ile Lys Thr Ile Asn Leu Gln Ser Asn Gly Leu Ile Gly
145                 150                 155                 160

Lys Leu Pro Pro Glu Ile Gly Asn Leu Lys Arg Leu Lys Asp Leu Leu
                165                 170                 175

Ile Gly Arg Asn Arg Leu Arg Ile Ser Val Pro Ile Ala Ala Lys Thr
            180                 185                 190

Ser Lys Lys Tyr Ala Ser Asn Pro Ser Ala Asn Ile Ser Gly Leu Cys
        195                 200                 205

Lys Ser Ser Gly Trp Lys Val Leu Asp Phe Cys Tyr Asn Trp Phe Glu
    210                 215                 220

Gly Arg Val Pro Ser Cys Leu Asp Tyr Leu Pro Ile Thr Ser Phe Gln
225                 230                 235                 240

Gly Asn Cys Met Lys Ser Met Asp Val Lys Gln His Pro Met Ser Glu
                245                 250                 255

Cys Ala His Leu Ala Val Thr Val Ala Lys Lys His Arg Ala Ser
            260                 265                 270

Arg Gln Ser Trp Leu Arg Asn Tyr Glu Ile Val Thr Gly Ser Ser Val
        275                 280                 285

Gly Leu Leu Phe Leu Val Val Met Phe Ser Ala Cys Ser Leu Cys Lys
    290                 295                 300

Ile Lys Arg Ser Leu Ile Val Pro Trp Lys Ser Ala Ser Asp Lys
305                 310                 315                 320

Asp Lys Phe Thr Val Tyr Val Glu Thr Glu Met Leu Lys Asp Val Ser
                325                 330                 335

Arg Tyr Thr Arg Gln Glu Leu Glu Val Ala Cys Glu Asp Phe Ser Asn

```
                    340             345             350
Ile Ile Asp Ser Ser Ala Glu Ser Gln Ile Tyr Lys Gly Thr Ile Lys
                355                 360                 365

Gly Gly Thr Glu Ile Ala Val Ile Ser Leu Cys Val Lys Asp Glu Asn
    370                 375                 380

Trp Thr Gly Tyr Leu Glu Leu Asn Phe Gln Arg Glu Leu Ala Ala Leu
385                 390                 395                 400

Met Lys Leu Asn His Glu Asn Ala Gly Lys Leu Leu Gly Tyr Cys Lys
                405                 410                 415

Glu Thr Thr Pro Phe Thr Arg Met Val Val Phe Asp Tyr Gly Ser Asn
                420                 425                 430

Val Thr Leu Tyr Glu His Leu His Tyr Val Asp Gly Ser Ile Val Ser
                435                 440                 445

Phe Val Lys Lys Ala Lys Ala Val Ile Gly Gly Ala Lys Gly Leu Lys
                450                 455                 460

Tyr Leu His Thr Glu Leu His Pro Pro Phe Thr Val Ser Glu Leu Ser
465                 470                 475                 480

Ser Thr Ala Val Tyr Leu Thr Glu Asp Phe Ser Pro Lys Leu Val Asp
                485                 490                 495

Trp Glu Ser Trp Lys Ile Ile Gln Val Arg Thr Glu Lys Asn Leu Lys
                500                 505                 510

Asn Ile Cys Asn Glu Gly Ala Ile Cys Val Leu Pro Asn Ala Met Glu
                515                 520                 525

His Arg Asp Met Asp Leu Gln Gly Asn Ile Tyr Ser Phe Gly Ile Leu
                530                 535                 540

Leu Leu Glu Ile Val Ser Gly Arg Pro Ser Tyr Cys Gln Asp Arg Gly
545                 550                 555                 560

Cys Leu Val Glu Trp Val Arg Glu Lys Asn Leu Gly Ala Pro Asp Val
                565                 570                 575

Met Ala Ser Leu Val Asp Pro Glu Leu Lys Lys Trp Lys Gln Lys Asp
                580                 585                 590

Leu Glu Ala Val Cys Glu Val Met Ser Gln Cys Leu Asn Leu Asp Gln
                595                 600                 605

Asn Glu Lys Asp Lys Asp Lys Ile Ser Cys Ser Ile Gln Ala Leu Cys
                610                 615                 620

Glu Thr Leu Glu Cys Arg Ile Thr Met Ser Ile Ser Ala Glu Phe Lys
625                 630                 635                 640

Ser Ser Ser Leu Ile Trp Leu Glu Leu Ala Leu Met Ser Pro Ser Asn
                645                 650                 655

Glu Asp Asp Asp Glu Arg Ser Lys
                660

<210> SEQ ID NO 31
<211> LENGTH: 1992
<212> TYPE: DNA
<213> ORGANISM: Artificial Sequence
<220> FEATURE:
<221> NAME/KEY: source
<222> LOCATION: 1..1992
<223> OTHER INFORMATION: /organism="Artificial Sequence"
      /note="Nucleotide sequence RLK1, variant 15"
      /mol_type="unassigned DNA"

<400> SEQUENCE: 31
atgagactgt acctgagcag caccatgcag ctgagcctga tgagcctggt gctgggcttc    60
ctgttcgtga gctgcgacgc cttcgccagc aaggaggtgg aggccgtgag aagattcaag   120
```

```
gaggccatct acaaggaccc cctgctggtg atgagcaact ggaacgtgcc caacctgagc    180
ccctgcgact ggaacggcat caagtgcagc cccagcaagg accacatcat caagatcaac    240
atcagcggca ccagcatgag aggcttcatc gtgcccgaga tcggccagat cacctacctg    300
caggagctga tcctgagagg caacatcctg atggccacca tccccaagga gatcggcaag    360
ctgaagaagc tgagaatcct ggacctgggc aacaaccacc tgaccggccc catccccgcc    420
gagatcggca gctgagcag aatcaagacc atcaacctgc agagccaggg cctgggcggc    480
aagctgcccc ccgagatcgg caacctgcac cacctgaagg agctgctgat cggcagaaac    540
agactgagag caagcgtgcc catcgccgcc aagaccagca gaagtacgc cagccagccc    600 tgcgccaaca tcagcggcct gtgcaagagc agcctgttca aggtggccga ctggagctac    660
aacttcttcg agggcagagt gcccagctgc ctggactacc tgcccatcac cagcttccag    720
ggcaactgca tgaagaccat ggacgtgaag cagagacccc tgagcgagac cgccagactg    780
gccatcaccg tggccaagaa gaagcacaag atcagcagac agacctggct gagaaacttc    840
gagatcgtga ccggcagcag cgtgggcctg ctgttcggcg tggtgatgtt cagcgcctgc    900
agcctgtgca agatcaagag aagcctgatc gtgccctggc acaagagcgc cagcgagaag    960
gagaagtaca ccgtgtacgt ggacagcgag atgctgaagg acgtgagcag atacaccaga   1020
caggagctgg aggtggcctg cgaggacttc agcaacatca tcgacagcag cgccgagagc   1080
cagatctaca agggcaccat caagggcggc accgagatcg ccgtgatcag cctgtgcgtg   1140
aaggaggaga ctggaccgg ctacctggag ctgaacttcc agagagaggt ggccgccctg   1200
gccagactga caaggagca ggccggcaag ctgctgggct ctgcaagga gagcacccc   1260 ttcaccagaa tggtggtgtt cgagtacgcc agcaacctga ccctgtacga ccacgcccac   1320
tacgccgacg gcagcctggt gagctgggcc agaagaatga agatcgtgat cggcctggcc   1380
agaggcctga gtacctgca caccgacctg cacccccct tcaccgtgtg cgagctgagc   1440
agcaccatcg tgtacgtgac cgaggacttc acccccaaga tcatggacta cgagtgctgg   1500
aagatcatcc aggtgagaag cgagaagaac ctgaagaaca tctgcaacga gggcgccatc   1560
tgcgtgctgc ccaacgccat ggagcacaga gacatggacc tgcagggcaa catctacagc   1620
ttcggcatcc tgctgctgga gatcgtgagc ggcagaccca gctactgcca ggacagaggc   1680
tgcctggtgg agtgggtgag agagaagaac ctggccgccc cgacgtgat ggccagcctg   1740 gtggaccccg agctgaagca cttcaagcag cacgagctgg aggccgtgtg cgaggtggcc   1800
tgccagtgca tgaacctgga ccagaacgag aaggagaagg acaagctgag ctgcagcatc   1860
caggccctgt gcgagaccct ggagagcaga atcaccgtga gcatcagcat ggagttcaag   1920
agcagcagcc tggcctgggc cgagctgccc ctggccagcc cagcaacga ggacgacgac   1980 gacagaagca ag                                                       1992
```

<210> SEQ ID NO 32
<211> LENGTH: 664
<212> TYPE: PRT
<213> ORGANISM: Artificial Sequence
<220> FEATURE:
<223> OTHER INFORMATION: Amino acid sequence RLK1, variant 15

<400> SEQUENCE: 32

```
Met Arg Leu Tyr Leu Ser Ser Thr Met Gln Leu Ser Leu Met Ser Leu
1               5                   10                  15

Val Leu Gly Phe Leu Phe Val Ser Cys Asp Ala Phe Ala Ser Lys Glu
```

-continued

Val Glu Ala Val Arg Arg Phe Lys Glu Ala Ile Tyr Lys Asp Pro Leu
              20                  25                  30
            35                  40                  45

Leu Val Met Ser Asn Trp Asn Val Pro Asn Leu Ser Pro Cys Asp Trp
            50                  55                  60

Asn Gly Ile Lys Cys Ser Pro Ser Lys Asp His Ile Ile Lys Ile Asn
65                  70                  75                  80

Ile Ser Gly Thr Ser Met Arg Gly Phe Ile Val Pro Glu Ile Gly Gln
                85                  90                  95

Ile Thr Tyr Leu Gln Glu Leu Ile Leu Arg Gly Asn Ile Leu Met Ala
            100                 105                 110

Thr Ile Pro Lys Glu Ile Gly Lys Leu Lys Lys Leu Arg Ile Leu Asp
            115                 120                 125

Leu Gly Asn Asn His Leu Thr Gly Pro Ile Pro Ala Glu Ile Gly Lys
            130                 135                 140

Leu Ser Arg Ile Lys Thr Ile Asn Leu Gln Ser Gln Gly Leu Gly Gly
145                 150                 155                 160

Lys Leu Pro Pro Glu Ile Gly Asn Leu His His Leu Lys Glu Leu Leu
                165                 170                 175

Ile Gly Arg Asn Arg Leu Arg Gly Ser Val Pro Ile Ala Ala Lys Thr
            180                 185                 190

Ser Lys Lys Tyr Ala Ser Gln Pro Cys Ala Asn Ile Ser Gly Leu Cys
            195                 200                 205

Lys Ser Ser Leu Phe Lys Val Ala Asp Trp Ser Tyr Asn Phe Phe Glu
            210                 215                 220

Gly Arg Val Pro Ser Cys Leu Asp Tyr Leu Pro Ile Thr Ser Phe Gln
225                 230                 235                 240

Gly Asn Cys Met Lys Thr Met Asp Val Lys Gln Arg Pro Leu Ser Glu
                245                 250                 255

Thr Ala Arg Leu Ala Ile Thr Val Ala Lys Lys His Lys Ile Ser
            260                 265                 270

Arg Gln Thr Trp Leu Arg Asn Phe Glu Ile Val Thr Gly Ser Ser Val
            275                 280                 285

Gly Leu Leu Phe Gly Val Val Met Phe Ser Ala Cys Ser Leu Cys Lys
            290                 295                 300

Ile Lys Arg Ser Leu Ile Val Pro Trp His Lys Ser Ala Ser Glu Lys
305                 310                 315                 320

Glu Lys Tyr Thr Val Tyr Val Asp Ser Glu Met Leu Lys Asp Val Ser
                325                 330                 335

Arg Tyr Thr Arg Gln Glu Leu Glu Val Ala Cys Glu Asp Phe Ser Asn
            340                 345                 350

Ile Ile Asp Ser Ser Ala Glu Ser Gln Ile Tyr Lys Gly Thr Ile Lys
            355                 360                 365

Gly Gly Thr Glu Ile Ala Val Ile Ser Leu Cys Val Lys Glu Glu Asn
            370                 375                 380

Trp Thr Gly Tyr Leu Glu Leu Asn Phe Gln Arg Glu Val Ala Ala Leu
385                 390                 395                 400

Ala Arg Leu Asn Lys Glu Gln Ala Gly Lys Leu Leu Gly Phe Cys Lys
                405                 410                 415

Glu Ser Thr Pro Phe Thr Arg Met Val Val Phe Glu Tyr Ala Ser Asn
            420                 425                 430

Leu Thr Leu Tyr Asp His Ala His Tyr Ala Asp Gly Ser Leu Val Ser
            435                 440                 445

```
Trp Ala Arg Arg Met Lys Ile Val Ile Gly Leu Ala Arg Gly Leu Lys
    450                 455                 460
Tyr Leu His Thr Asp Leu His Pro Pro Phe Thr Val Cys Glu Leu Ser
465                 470                 475                 480
Ser Thr Ile Val Tyr Val Thr Glu Asp Phe Thr Pro Lys Ile Met Asp
                485                 490                 495
Tyr Glu Cys Trp Lys Ile Ile Gln Val Arg Ser Glu Lys Asn Leu Lys
            500                 505                 510
Asn Ile Cys Asn Glu Gly Ala Ile Cys Val Leu Pro Asn Ala Met Glu
        515                 520                 525
His Arg Asp Met Asp Leu Gln Gly Asn Ile Tyr Ser Phe Gly Ile Leu
    530                 535                 540
Leu Leu Glu Ile Val Ser Gly Arg Pro Ser Tyr Cys Gln Asp Arg Gly
545                 550                 555                 560
Cys Leu Val Glu Trp Val Arg Glu Lys Asn Leu Gly Ala Pro Asp Val
                565                 570                 575
Met Ala Ser Leu Val Asp Pro Glu Leu Lys His Phe Lys Gln His Glu
            580                 585                 590
Leu Glu Ala Val Cys Glu Val Ala Cys Gln Cys Met Asn Leu Asp Gln
        595                 600                 605
Asn Glu Lys Glu Lys Asp Lys Leu Ser Cys Ser Ile Gln Ala Leu Cys
    610                 615                 620
Glu Thr Leu Glu Ser Arg Ile Thr Val Ser Ile Ser Met Glu Phe Lys
625                 630                 635                 640
Ser Ser Ser Leu Ala Trp Ala Glu Leu Ala Leu Ala Ser Pro Ser Asn
                645                 650                 655
Glu Asp Asp Asp Asp Arg Ser Lys
            660
```

<210> SEQ ID NO 33
<211> LENGTH: 1992
<212> TYPE: DNA
<213> ORGANISM: Artificial Sequence
<220> FEATURE:
<221> NAME/KEY: source
<222> LOCATION: 1..1992
<223> OTHER INFORMATION: /organism="Artificial Sequence"
    /note="Nucleotide sequence RLK1, variant 16"
    /mol_type="unassigned DNA"

<400> SEQUENCE: 33

| | |
|---|---|
| atgagactgt acctgagcag caccatgcag ctgagcctga tgagcctggt gctgggcttc | 60 |
| ctgttcgtga gctgcgacgc cttcgccagc aaggaggtgg aggccgtgag aagattcaag | 120 |
| gaggccatct acaaggaccc cctgctggtg atgagcaact ggaacgtgcc caacctgagc | 180 |
| ccctgcgact ggaacggcat caagtgcagc cccagcaagg accacatcat caagatcaac | 240 |
| atcagcggca ccagcatgag aggcttcatc gtgcccgaga tcggccagat cacctacctg | 300 |
| caggagctga tcctgagagg caacatcctg atggccacca tccccaagga gatcggcaag | 360 |
| ctgaagaagc tgagaatcct ggacctgggc aacaaccacc tgaccggccc catccccgcc | 420 |
| gagatcggca gctgagcag aatcaagacc atccagctgc agagcaacgg cctgatcggc | 480 |
| aagctgcccc ccgagatcgg caacctgaag cacggcaagg agctgctgat cggcagaaac | 540 |
| agactgagag gcagcgtgcc catcgccgcc aagaccagca gaagtacgc cagcaacccc | 600 |
| agcgccaaca tcagcggcct gtgcaagagc agcctgttca aggtggccga cttcagctac | 660 |

-continued

```
aacttcttcg agggcagagt gcccagctgc ctggactacc tgcccatcac cagcttccag    720
ggcaactgca tgaagaccat ggacgtgaag cagagacccc tgagcgactg cgccagactg    780
gccgtgaccg tggccaagaa gaagcacaga gcctgcagac agagctggct gagaaacttc    840
gagatcatca ccggcagcag cgtgggcctg ctgttcctga tggtgatgtt cagcgcctgc    900
tgcctgtgca aggccaagag aagcctgatc gtgccctgga agaagagcgc cagcgagaag    960
gagaagttca ccgtgtacgt ggacagcgag atgctgaagg acgtgagcag atacaccaga   1020
caggagctgg aggtggcctg cgaggacttc agcaacatca tcgacagcag cgccgagagc   1080
cagatctaca agggcaccat caagggcggc accgagatcg ccgtgatcag cctgtgcgtg   1140
aaggacgaga actggaccgg ctacctggag ctgaacttcc agagagaggt ggccgccctg   1200
gccagactga ccacgagaa cgccggcaag ggcctgggct actgcaagga gaccaccccc   1260
ttcaccagaa tgctggcctt cgactacgcc agcaacggca ccctgtacga ccacctgcac   1320
tacgccgacg cagcctggt gagctgggcc aagagaatga agatcgtgat cggcatcgcc   1380
agaggcctga agtacctgca caccgagctg caccccccct tcaccgtgag cgagctgacc   1440
agcaccgccg tgtggctgac cgaggacttc accccaagc tggtggactt cgagtgctgg   1500
aagatcatcc aggtgagaag cgagaagaac ctgaagaaca tctgcaacga gggcgccatc   1560
tgcgtgctgc ccaacgccat ggagcacaga gacatggacc tgcagggcaa catctacagc   1620
ttcggcatcc tgctgctgga gatcgtgagc ggcagaccca gctactgcca ggacagaggc   1680
tgcctggtgg agtgggtgag agagaagaac ctgggcgccc ccgacgtgat ggccagcctg   1740
gtggaccccg agctgaagca cttccaccag cacgagctgg aggccgtgtg cgaggtggcc   1800
agccagtgcc tgaacctgga ccagaacgag aaggacaagg acaagctgag ctgcagcatc   1860
caggccctgt gcgagaccct ggagagcaga atcaccgtga gcatcagcgc cgagttcaag   1920
agcagcagcc tggcctgggc cgagctggcc ctggcctgcc ccagcaacga ggacgacgac   1980
gacagaagca ag                                                      1992
```

<210> SEQ ID NO 34
<211> LENGTH: 664
<212> TYPE: PRT
<213> ORGANISM: Artificial Sequence
<220> FEATURE:
<223> OTHER INFORMATION: Amino acid sequence RLK1, variant 16

<400> SEQUENCE: 34

```
Met Arg Leu Tyr Leu Ser Ser Thr Met Gln Leu Ser Leu Met Ser Leu
1               5                   10                  15

Val Leu Gly Phe Leu Phe Val Ser Cys Asp Ala Phe Ala Ser Lys Glu
            20                  25                  30

Val Glu Ala Val Arg Arg Phe Lys Glu Ala Ile Tyr Lys Asp Pro Leu
        35                  40                  45

Leu Val Met Ser Asn Trp Asn Val Pro Asn Leu Ser Pro Cys Asp Trp
    50                  55                  60

Asn Gly Ile Lys Cys Ser Pro Ser Lys Asp His Ile Ile Lys Ile Asn
65                  70                  75                  80

Ile Ser Gly Thr Ser Met Arg Gly Phe Ile Val Pro Glu Ile Gly Gln
                85                  90                  95

Ile Thr Tyr Leu Gln Glu Leu Ile Leu Arg Gly Asn Ile Leu Met Ala
            100                 105                 110

Thr Ile Pro Lys Glu Ile Gly Lys Leu Lys Lys Leu Arg Ile Leu Asp
        115                 120                 125
```

```
Leu Gly Asn Asn His Leu Thr Gly Pro Ile Pro Ala Glu Ile Gly Lys
130                 135                 140

Leu Ser Arg Ile Lys Thr Ile Gln Leu Gln Ser Asn Gly Leu Ile Gly
145                 150                 155                 160

Lys Leu Pro Pro Glu Ile Gly Asn Leu Lys His Gly Lys Glu Leu Leu
                165                 170                 175

Ile Gly Arg Asn Arg Leu Arg Gly Ser Val Pro Ile Ala Ala Lys Thr
            180                 185                 190

Ser Lys Lys Tyr Ala Ser Asn Pro Ser Ala Asn Ile Ser Gly Leu Cys
        195                 200                 205

Lys Ser Ser Leu Phe Lys Val Ala Asp Phe Ser Tyr Asn Phe Phe Glu
210                 215                 220

Gly Arg Val Pro Ser Cys Leu Asp Tyr Leu Pro Ile Thr Ser Phe Gln
225                 230                 235                 240

Gly Asn Cys Met Lys Thr Met Asp Val Lys Gln Arg Pro Leu Ser Asp
                245                 250                 255

Cys Ala Arg Leu Ala Val Thr Val Ala Lys Lys His Arg Ala Cys
            260                 265                 270

Arg Gln Ser Trp Leu Arg Asn Phe Glu Ile Ile Thr Gly Ser Ser Val
        275                 280                 285

Gly Leu Leu Phe Leu Met Val Met Phe Ser Ala Cys Cys Leu Cys Lys
290                 295                 300

Ala Lys Arg Ser Leu Ile Val Pro Trp Lys Lys Ser Ala Ser Glu Lys
305                 310                 315                 320

Glu Lys Phe Thr Val Tyr Val Asp Ser Glu Met Leu Lys Asp Val Ser
                325                 330                 335

Arg Tyr Thr Arg Gln Glu Leu Glu Val Ala Cys Glu Asp Phe Ser Asn
            340                 345                 350

Ile Ile Asp Ser Ser Ala Glu Ser Gln Ile Tyr Lys Gly Thr Ile Lys
        355                 360                 365

Gly Gly Thr Glu Ile Ala Val Ile Ser Leu Cys Val Lys Asp Glu Asn
370                 375                 380

Trp Thr Gly Tyr Leu Glu Leu Asn Phe Gln Arg Glu Val Ala Ala Leu
385                 390                 395                 400

Ala Arg Leu Asn His Glu Asn Ala Gly Lys Gly Leu Gly Tyr Cys Lys
                405                 410                 415

Glu Thr Thr Pro Phe Thr Arg Met Leu Ala Phe Asp Tyr Ala Ser Asn
            420                 425                 430

Gly Thr Leu Tyr Asp His Leu His Tyr Ala Asp Gly Ser Leu Val Ser
        435                 440                 445

Trp Ala Lys Arg Met Lys Ile Val Ile Gly Ile Ala Arg Gly Leu Lys
450                 455                 460

Tyr Leu His Thr Glu Leu His Pro Pro Phe Thr Val Ser Glu Leu Thr
465                 470                 475                 480

Ser Thr Ala Val Trp Leu Thr Glu Asp Phe Thr Pro Lys Leu Val Asp
                485                 490                 495

Phe Glu Cys Trp Lys Ile Ile Gln Val Arg Ser Glu Lys Asn Leu Lys
            500                 505                 510

Asn Ile Cys Asn Glu Gly Ala Ile Cys Val Leu Pro Asn Ala Met Glu
        515                 520                 525

His Arg Asp Met Asp Leu Gln Gly Asn Ile Tyr Ser Phe Gly Ile Leu
530                 535                 540
```

```
Leu Leu Glu Ile Val Ser Gly Arg Pro Ser Tyr Cys Gln Asp Arg Gly
545                 550                 555                 560

Cys Leu Val Glu Trp Val Arg Glu Lys Asn Leu Gly Ala Pro Asp Val
                565                 570                 575

Met Ala Ser Leu Val Asp Pro Glu Leu Lys His Phe His Gln His Glu
                580                 585                 590

Leu Glu Ala Val Cys Glu Val Ala Ser Gln Cys Leu Asn Leu Asp Gln
            595                 600                 605

Asn Glu Lys Asp Lys Asp Lys Leu Ser Cys Ser Ile Gln Ala Leu Cys
            610                 615                 620

Glu Thr Leu Glu Ser Arg Ile Thr Val Ser Ile Ser Ala Glu Phe Lys
625                 630                 635                 640

Ser Ser Ser Leu Ala Trp Ala Glu Leu Ala Leu Ala Cys Pro Ser Asn
                645                 650                 655

Glu Asp Asp Asp Asp Arg Ser Lys
                660
```

FUNGAL RESISTANT PLANTS EXPRESSING RLK1

This application is a continuation application of U.S. application Ser. No. 16/451,984, filed Jun. 25, 2019 (now U.S. Pat. No. 11,142,774), which is a continuation application of U.S. application Ser. No. 14/419,510 (now U.S. Pat. No. 10,329,580), which is a National Stacie application of International Application No. PCT/IB2013/056112, filed Jul. 25, 2013, which claims the benefit of U.S. Provisional Patent Application No. 61/681,161, filed Aug. 9, 2012, the entire contents of which are hereby incorporated herein by reference. International Application No. PCT/IB2013/056112 also claims priority under 35 U.S.C. § 119 to European Patent Application No. 12179859, filed Aug. 9, 2012, the entire contents of which are hereby incorporated herein by reference.

REFERENCE TO SEQUENCE LISTING SUBMITTED VIA EFS-WEB

This application was filed electronically via EFS-Web and includes an electronically submitted sequence listing in .txt format. The .txt file contains a sequence listing entitled "Sequence_List.txt" created on Oct. 11, 2021, and is 119,558 bytes in size. The sequence listing contained in this .txt file is part of the specification and is hereby incorporated by reference herein in its entirety.

The present invention relates to a method of increasing resistance against fungal pathogens, in particular, pathogens of the order Pucciniales, for example soybean rust, in plants, plant parts, and/or plant cells. This is achieved by increasing the expression and/or activity of an RLK1 protein in a plant, plant part and/or plant cell in comparison to wild type plants, wild type plant parts and/or wild type plant cells.

SUMMARY OF THE INVENTION

Furthermore, the invention relates to transgenic plants, plant parts, and/or plant cells having an increased resistance against fungal pathogens, in particular, pathogens of the order Pucciniales, for example soybean rust, and to recombinant expression vectors comprising a sequence that is identical or homologous to a sequence encoding an RLK1 protein.

BACKGROUND OF THE INVENTION

The cultivation of agricultural crop plants serves mainly for the production of foodstuffs for humans and animals. Monocultures in particular, which are the rule nowadays, are highly susceptible to an epidemic-like spreading of diseases. The result is markedly reduced yields. To date, the pathogenic organisms have been controlled mainly by using pesticides. Nowadays, the possibility of directly modifying the genetic disposition of a plant or pathogen is also open to man.

Resistance generally describes the ability of a plant to prevent, or at least curtail the infestation and colonization by a harmful pathogen. Different mechanisms can be discerned in the naturally occurring resistance, with which the plants fend off colonization by phytopathogenic organisms. These specific interactions between the pathogen and the host determine the course of infection (Schopfer and Brennicke (1999) Pflanzenphysiologie, Springer Verlag, Berlin-Heidelberg, Germany).

With regard to the race specific resistance, also called host resistance, a differentiation is made between compatible and incompatible interactions. In the compatible interaction, an Interaction occurs between a virulent pathogen and a susceptible plant. The pathogen survives, and may build up reproduction structures, while the host mostly dies off. An incompatible interaction occurs on the other hand when the pathogen infects the plant but is inhibited in its growth before or after weak development of symptoms (mostly by the presence of R genes of the NBS-LRR family, see below). In the latter case, the plant is resistant to the respective pathogen (Schopfer and Brennicke, vide supra). However, this type of resistance is specific for a certain strain or pathogen.

In both compatible and incompatible interactions a defensive and specific reaction of the host to the pathogen occurs. In nature, however, this resistance is often overcome because of the rapid evolutionary development of new virulent races of the pathogens (Neu et al. (2003) American Cytopathol. Society, MPMI 16 No. 7: 626-633).

Most pathogens are plant-species specific. This means that a pathogen can induce a disease in a certain plant species, but not in other plant species (Heath (2002) Can. J. Plant Pathol. 24: 259-264). The resistance against a pathogen in certain plant species is called non-host resistance. The non-host resistance offers strong, broad, and permanent protection from phytopathogens. Genes providing non-host resistance provide the opportunity of a strong, broad and permanent protection against certain diseases in non-host plants. In particular, such a resistance works for different strains of the pathogen.

*Fungi* are distributed worldwide. Approximately 100 000 different fungal species are known to date. Thereof rusts are of great importance. They can have a complicated development cycle with up to five different spore stages (spermatium, aeciospore, uredospore, teleutospore and basidiospore).

During the infection of plants by pathogenic *fungi*, different phases are usually observed. The first phases of the interaction between phytopathogenic *fungi* and their potential host plants are decisive for the colonization of the plant by the fungus. During the first stage of the infection, the spores become attached to the surface of the plants, germinate, and the fungus penetrates the plant. *Fungi* may penetrate the plant via existing ports such as stomata, lenticels, hydatodes and wounds, or else they penetrate the plant epidermis directly as the result of the mechanical force and with the aid of cell-wall-digesting enzymes. Specific infection structures are developed for penetration of the plant.

Immediately after recognition of a potential pathogen the plant starts to elicit defense reactions. Mostly the presence of the pathogen is sensed via so called PAMP receptors, a class of trans-membrane receptor like kinases recognizing conserved pathogen associated molecules (e.g. flagellin or chitin). Receptor-like kinases (RLKs) are signaling proteins that feature an extracellular domain connected via a transmembrane domain to a cytoplasmic kinase. This architecture indicates that RLKs perceive external signals, transducing them into the cell. In plants, RLKs were first implicated in the regulation of development, in pathogen responses, and in recognition events. (Santiago A Morillo and Frans E Tax (2006) Functional analysis of receptor-like kinases in monocots and dicots. Current Opinion in Plant Biology 9:460-469).

Only very few of the RLKs are described to be involved in the recognition of conserved structures of microbes (microbe associated molecular patterns, PAMPs, for review see Thorsten Nurnberger and Birgit Kemmerling (2006) Receptor protein kinases—pattern recognition receptors in plant immunity. TRENDS in Plant Science 11(11)519ff).

Downstream of the PAMP receptors, the phytohormones salicylic acid (SA), jasmonate (JA) and ethylene (ET) play a critical role in the regulation of the different defense reactions. Depending on the ratio of the different phytohormones, different defense reactions are elicited by the host cell. Generally SA dependent defense is linked with resistance against biotrophic pathogens, whereas JA/ET dependent defense reactions are active against necrotrophic pathogens (and insects).

Another more specific resistance mechanism is based on the presence of so called resistance genes (R-genes). Most R genes belong to the nucleotide-binding site-leucine-rich repeat (NBS-LRR) gene family and function in monitoring the presence of pathogen effector proteins (virulence factors). After recognizing the pathogen derived proteins a strong defense reaction (mostly accompanied by a programmed cell death) is elicited.

The soybean rust *Phakopsora pachyrhizi* directly penetrates the plant epidermis. After crossing the epidermal cell, the fungus reaches the intercellular space of the mesophyll, where the fungus starts to spread through the leaves. To acquire nutrients the fungus penetrates mesophyll cells and develops haustoria inside the mesophyl cell. During the penetration process the plasmamembrane of the penetrated mesophyll cell stays intact. Therefore the soybean rust fungus establishes a biotrophic interaction with soybean.

The biotrophic phytopathogenic *fungi*, such as soybean rust and all other rust *fungi*, depend for their nutrition on the metabolism of living cells of the plants. This type of *fungi* belong to the group of biotrophic *fungi*, like other rust *fungi*, powdery mildew *fungi* or oomycete pathogens like the genus *Phytophthora* or *Peronospora*. The necrotrophic phytopathogenic *fungi* depend for their nutrition on dead cells of the plants, e.g. species from the genus *Fusarium, Rhizoctonia* or *Mycospaerella*. Soybean rust has occupied an intermediate position, since it penetrates the epidermis directly, whereupon the penetrated cell becomes necrotic. After the penetration, the fungus changes over to an obligatory-biotrophic lifestyle. The subgroup of the biotrophic fungal pathogens which follows essentially such an infection strategy is heminecrotrohic. In contrast to a heminecrotrophic pathogen, a hemibiotrophic pathogen lives for a short period of time in a biotrophic manner and subsequently starts killing the host cell and/or host organism, i.e., changes for the rest of its life-cycle to a necrotrophic life-style.

Soybean rust has become increasingly important in recent times. The disease may be caused by the biotrophic rusts *Phakopsora pachyrhizi* and *Phakopsora meibomiae*. They belong to the class Basidiomycota, order Uredinales, family Phakopsoraceae. Both rusts infect a wide spectrum of leguminosic host plants. *P. pachyrhizi*, also referred to as Asian rust, is the more aggressive pathogen on soy (*Glycine max*), and is therefore, at least currently, of great importance for agriculture. *P. pachyrhizi* can be found in nearly all tropical and subtropical soy growing regions of the world. *P. pachyrhizi* is capable of infecting 31 species from 17 families of the Leguminosae under natural conditions and is capable of growing on further 60 species under controlled conditions (Sinclair et al. (eds.), Proceedings of the rust workshop (1995), National SoyaResearch Laboratory, Publication No. 1 (1996); Rytter J. L. et al., Plant Dis. 87, 818 (1984)). *P. meibomiae* has been found in the Caribbean Basin and in Puerto Rico, and has not caused substantial damage as yet.

*P. pachyrhizi* can currently be controlled in the field only by means of fungicides. Soy plants with resistance to the entire spectrum of the isolates are not available. When searching for resistant soybean accessions, six dominant R-genes of the NBS-LRR family, named Rpp1-5 and Rpp? (Hyuuga), which mediate resistance of soy to *P. pachyrhizi*, were discovered by screening thousands of soybean varieties. As the R-genes are derived from a host (soybean), the resistance was lost rapidly, as *P. pachyrhizi* develops new virulent races. Therefore there is a strong need to discover R-genes that are derived from non-hosts plants (e.g. *Arabidopsis*) as they are thought to be more durable.

In recent years, fungal diseases, e.g. soybean rust, has gained in importance as pest in agricultural production. There was therefore a demand in the prior art for developing methods to control *fungi* and to provide fungal resistant plants.

Much research has been performed on the field of powdery and downy mildew infecting the epidermal layer of plants. However, the problem to cope with soybean rust which infects the mesophyll remains unsolved.

The object of the present invention is inter alia to provide a method of increasing resistance against fungal pathogens, preferably against fungal rust pathogens (i.e., fungal pathogens of the order Pucciniales), preferably pathogens of the family Phakopsoraceae, more preferably against fungal pathogens of the genus *Phakopsora*, most preferably against *Phakopsora pachyrhizi* and *Phakopsora meibomiae*, also known as soybean rust.

Surprisingly, we found that fungal pathogens, in particular of the Phakopsoorder Pucciniales, for example soybean rust, can be controlled by increasing the expression of a RLK1 protein.

The present invention therefore provides a method of increasing resistance against fungal pathogens, preferably against rust pathogens (i.e., fungal pathogens of the order Pucciniales), preferably against fungal pathogens of the family Phakopsoraceae, more preferably against fungal pathogens of the genus *Phakopsora*, most preferably against *Phakopsora pachyrhizi* and *Phakopsora meibomiae*, also known as soybean rust, in transgenic plants, transgenic plant parts, or transgenic plant cells by overexpressing one or more RLK1 nucleic acids.

A further object is to provide transgenic plants resistant against fungal pathogens, preferably rust pathogens (i.e., fungal pathogens of the order Pucciniales), preferably of the family Phakopsoraceae, more preferably against fungal pathogens of the genus *Phakopsora*, most preferably against *Phakopsora pachyrhizi* and *Phakopsora meibomiae*, also known as soybean rust, a method for producing such plants as well as a vector construct useful for the above methods.

Therefore, the present invention also refers to a recombinant vector construct and a transgenic plant, transgenic plant part, or transgenic plant cell comprising an exogenous RLK1 nucleic acid. Furthermore, a method for the production of a transgenic plant, transgenic plant part or transgenic plant cell using the nucleic acid of the present invention is claimed herein. In addition, the use of a nucleic acid or the recombinant vector of the present invention for the transformation of a plant, plant part, or plant cell is claimed herein.

The objects of the present invention, as outlined above, are achieved by the subject-matter of the main claims. Preferred embodiments of the invention are defined by the subject matter of the dependent claims.

BRIEF SUMMARY OF THE INVENTION

The object of the present invention is inter alia to provide a method of increasing resistance against fungal pathogens, preferably rust pathogens (i.e., fungal pathogens of the order Pucciniales), preferably against fungal pathogens of the family Phakopsoraceae, more preferably against fungal pathogens of the genus *Phakopsora*, most preferably against *Phakopsora pachyrhizi* and *Phakopsora meibomiae*, also known as soybean rust.

Surprisingly, we found that resistance against fungal pathogens, in particular of the order Pucciniales, for example soybean rust, can be enhanced by increasing the expression of a RLK1 protein.

The present invention therefore provides a method of increasing resistance against fungal pathogens, preferably rust pathogens (i.e., fungal pathogens of the order Pucciniales), preferably against fungal pathogens of the family Phakopsoraceae, more preferably against fungal pathogens of the genus *Phakopsora*, most preferably against *Phakopsora pachyrhizi* and *Phakopsora meibomiae*, also known as soybean rust, in transgenic plants, transgenic plant parts, or transgenic plant cells by overexpressing one or more RLK1 nucleic acids.

A further object is to provide transgenic plants resistant against fungal pathogens, preferably rust pathogens (i.e., fungal pathogens of the order Pucciniales), preferably of the family Phakopsoraceae, more preferably against fungal pathogens of the genus *Phakopsora*, most preferably against *Phakopsora pachyrhizi* and *Phakopsora meibomiae*, also known as soybean rust, a method for producing such plants as well as a vector construct useful for the above methods.

Therefore, the present invention also refers to a recombinant vector construct and a transgenic plant, transgenic plant part, or transgenic plant cell comprising an exogenous RLK1 nucleic acid. Furthermore, a method for the production of a transgenic plant, transgenic plant part or transgenic plant cell using the nucleic acid of the present invention is claimed herein. In addition, the use of a nucleic acid or the recombinant vector of the present invention for the transformation of a plant, plant part, or plant cell is claimed herein.

The objects of the present invention, as outlined above, are achieved by the subject-matter of the main claims. Preferred embodiments of the invention are defined by the subject matter of the dependent claims.

BRIEF DESCRIPTION OF THE SEVERAL VIEWS OF THE DRAWINGS

FIG. 3 shows the full-length cDNA sequence of the RLK1 gene from *Arabidopsis thaliana* having SEQ ID NO: 1.

FIG. 4 shows the sequence of a RLK1 protein (SEQ ID NO: 2).

FIG. 5 shows the sequence of the *Arabidopsis thaliana* genomic sequence (part of accession No NC_003076.8) around the region, which codes for RLK1, and having SEQ ID NO: 3.

FIG. 6 shows the alignment of the *Arabidopsis* genome sequence (part of accession No NC_003076.8, SEQ ID NO: 3) and the sequence of the cDNA of RLK1 (SEQ ID NO: 1). In FIG. 6 the genome sequence (SEQ ID NO: 3) is truncated at its 3' and 5' end. The truncated genome sequence is shown in SEQ ID NO: 8.

FIG. 7 shows the result of the scoring of 42 transgenic soy plants (derived from 5 independent events) expressing the RLK1 overexpression vector construct. $T_1$ soybean plants expressing RLK1 protein were inoculated with spores of *Phakopsora pachyrhizi*. The evaluation of the diseased leaf area on all leaves was performed 14 days after inoculation. The average of the percentage of the leaf area showing fungal colonies or strong yellowing/browning on all leaves was considered as diseased leaf area. At all 42 soybean $T_1$ plants expressing RLK1 (expression checked by RT-PCR) were evaluated in parallel to non-transgenic control plants. The average of the diseased leaf area is shown in FIG. 7. Overexpression of RLK1 significantly (*:$p<0.05$) reduces the diseased leaf area in comparison to non-transgenic control plants by 29.0%.

FIG. 8 contains a brief description of the sequences of the sequence listing.

DETAILED DESCRIPTION OF THE INVENTION

The present invention may be understood more readily by reference to the following detailed description of the preferred embodiments of the invention and the examples included herein.

Definitions

Unless otherwise noted, the terms used herein are to be understood according to conventional usage by those of ordinary skill in the relevant art. In addition to the definitions of terms provided herein, definitions of common terms in molecular biology may also be found in Rieger et al., 1991 Glossary of genetics: classical and molecular, 5th Ed., Berlin: Springer-Verlag; and in Current Protocols in Molecular Biology, F. M. Ausubel et al., Eds., Current Protocols, a joint venture between Greene Publishing Associates, Inc. and John Wiley & Sons, Inc., (1998 Supplement).

It is to be understood that as used in the specification and in the claims, “a” or “an” can mean one or more, depending upon the context in which it is used. Thus, for example, reference to “a cell” can mean that at least one cell can be utilized. It is to be understood that the terminology used herein is for the purpose of describing specific embodiments only and is not intended to be limiting.

Throughout this application, various publications are referenced. The disclosures of all of these publications and those references cited within those publications in their entireties are hereby incorporated by reference into this application in order to more fully describe the state of the art to which this invention pertains. Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al., 1989 Molecular Cloning, Second Edition, Cold Spring Harbor Laboratory, Plainview, N.Y.; Maniatis et al., 1982 Molecular Cloning, Cold Spring Harbor Laboratory, Plainview, N.Y.; Wu (Ed.) 1993 Meth. Enzymol. 218, Part I; Wu (Ed.) 1979 Meth Enzymol. 68; Wu et al., (Eds.) 1983 Meth. Enzymol. 100 and 101; Grossman and Moldave (Eds.) 1980 Meth. Enzymol. 65; Miller (Ed.) 1972 Experiments in Molecular Genetics, Cold Spring Harbor Laboratory, Cold Spring Harbor, N.Y.; Old and Primrose, 1981 Principles of Gene Manipulation, University of California Press, Berkeley; Schleif and Wensink, 1982 Practical Methods in Molecular Biology; Glover (Ed.) 1985 DNA Cloning Vol. I and II, IRL Press, Oxford, UK; Hames and Higgins (Eds.) 1985 Nucleic Acid Hybridization, IRL Press, Oxford, UK; and Setiow and Hollaender 1979 Genetic Engineering: Principles and Methods, Vols. 1-4, Plenum Press, New York. Abbreviations and nomenclature, where employed, are deemed standard in the field and commonly used in professional journals such as those cited herein.

Figure 1:
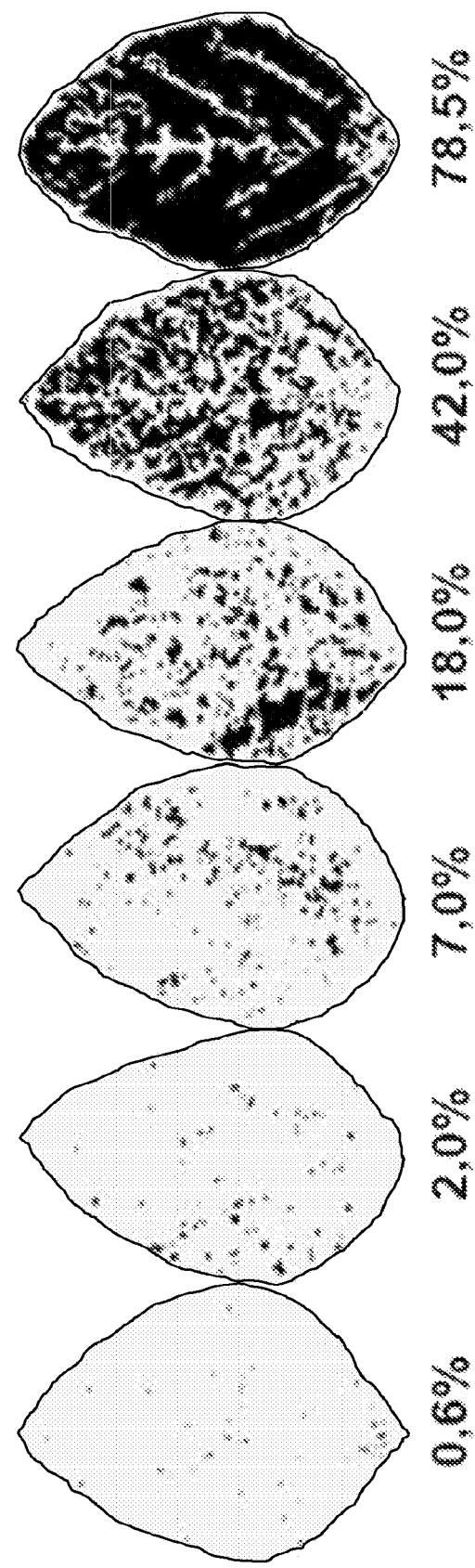
FIG. 1 shows the scoring system used to determine the level of diseased leaf area of wildtype and transgenic soy plants against the rust fungus *P. pachyrhizi* (as described in GODOY, C. V., KOGA, L. J. & CANTERI, M. G. Diagrammatic scale for assessment of soybean rust severity. Fitopatologia Brasileira 31:063-068. 2006).

"Homologues" of a protein encompass peptides, oligopeptides, polypeptides, proteins and/or enzymes having amino acid substitutions, deletions and/or insertions relative to the unmodified protein in question and having similar functional activity as the unmodified protein from which they are derived.

"Homologues" of a nucleic acid encompass nucleotides and/or polynucleotides having nucleic acid substitutions, deletions and/or insertions relative to the unmodified nucleic acid in question, wherein the protein coded by such nucleic acids has similar or higher functional activity as the unmodified protein coded by the unmodified nucleic acid from which they are derived. In particular, homologues of a nucleic acid may encompass substitutions on the basis of the degenerative amino acid code.

A "deletion" refers to removal of one or more amino acids from a protein or to the removal of one or more nucleic acids from DNA, ssRNA and/or dsRNA.

An "Insertion" refers to one or more amino acid residues or nucleic acid residues being introduced into a predetermined site in a protein or the nucleic acid.

A "substitution" refers to replacement of amino acids of the protein with other amino acids having similar properties (such as similar hydrophobicity, hydrophilicity, antigenicity, propensity to form or break α-helical structures or beta-sheet structures).

On the nucleic acid level a substitution refers to a replacement of one or more nucleotides with other nucleotides within a nucleic acid, wherein the protein coded by the modified nucleic acid has a similar function. In particular homologues of a nucleic acid encompass substitutions on the basis of the degenerative amino acid code.

Amino acid substitutions are typically of single residues, but may be clustered depending upon functional constraints placed upon the protein and may range from 1 to 10 amino acids; insertions or deletion will usually be of the order of about 1 to 10 amino acid residues.

The amino acid substitutions are preferably conservative amino acid substitutions. Conservative substitution tables are well known in the art (see for example Creighton (1984) Proteins. W.H. Freeman and Company (Eds) and Table 1 below, or Taylor W. R. (1986) The classification of amino acid conservation J Theor Biol., 119:205-18).

TABLE 1

Examples of conserved amino acid substitutions

| Residue | Conservative Substitutions | Residue | Conservative Substitutions |
|---|---|---|---|
| Ala | Ser | Leu | Ile; Val |
| Arg | Lys | Lys | Arg; Gln |
| Asn | Gln; His | Met | Leu; Ile |
| Asp | Glu | Phe | Met; Leu; Tyr |

TABLE 1-continued

Examples of conserved amino acid substitutions

| Residue | Conservative Substitutions | Residue | Conservative Substitutions |
|---|---|---|---|
| Gln | Asn | Ser | Thr; Gly |
| Cys | Ser | Thr | Ser; Val |
| Glu | Asp | Trp | Tyr |
| Gly | Pro | Tyr | Trp; Phe |
| His | Asn; Gln | Val | Ile; Leu |
| Ile | Leu, Val | | |

Amino acid substitutions, deletions and/or insertions may readily be made using peptide synthetic techniques well known in the art, such as solid phase peptide synthesis and the like, or by recombinant DNA manipulation.

Methods for the manipulation of DNA sequences to produce substitution, insertion or deletion variants of a protein are well known in the art. For example, techniques for making substitution mutations at predetermined sites in DNA are well known to those skilled in the art and include M13 mutagenesis, T7-Gene in vitro mutagenesis (USB, Cleveland, Ohio), QuickChange Site Directed mutagenesis (Stratagene, San Diego, Calif.), PCR-mediated site-directed mutagenesis or other site-directed mutagenesis protocols.

Orthologues and paralogues encompass evolutionary concepts used to describe the ancestral relationships of genes. Paralogues are genes within the same species that have originated through duplication of an ancestral gene; orthologues are genes from different organisms that have originated through speciation, and are also derived from a common ancestral gene.

The terms "encode" or "coding for" is used for the capability of a nucleic acid to contain the information for the amino acid sequence of a protein via the genetic code, i.e., the succession of codons each being a sequence of three nucleotides, which specify which amino acid will be added next during protein synthesis. The terms "encode" or "coding for" therefore Includes all possible reading frames of a nucleic acid. Furthermore, the terms "encode" or "coding for" also applies to a nucleic acid, which coding sequence is interrupted by noncoding nucleic acid sequences, which are removed prior translation, e.g., a nucleic acid sequence comprising introns.

The term "domain" refers to a set of amino acids conserved at specific positions along an alignment of sequences of evolutionarily related proteins. While amino acids at other positions can vary between homologues, amino acids that are highly conserved at specific positions indicate amino acids that are likely essential in the structure, stability or function of a protein.

Specialist databases exist for the identification of domains, for example, SMART (Schultz et al. (1998) Proc. Natl. Acad. Sci. USA 95, 5857-5864; Letunic et al. (2002) Nucleic Acids Res 30, 242-244), InterPro (Mulder et al., (2003) Nucl. Acids. Res. 31, 315-318), Prosite (Bucher and Bairoch (1994), A generalized profile syntax for biomolecular sequences motifs and its function in automatic sequence interpretation. (In) ISMB-94; Proceedings 2nd International Conference on Intelligent Systems for Molecular Biology. Altman R., Brutlag D., Karp P., Lathrop R., Searis D., Eds., pp 53-61, AAAI Press, Menlo Park; Hulo et al., Nucl. Acids. Res. 32:D134-D137, (2004)), or Pfam (Bateman et al., Nucleic Acids Research 30(1): 276-280 (2002)). A set of tools for in silico analysis of protein sequences is available on the ExPASy proteomics server (Swiss Institute of Bioinformatics (Gasteiger et al., ExPASy: the proteomics server for in-depth protein knowledge and analysis, Nucleic Acids Res. 31:3784-3788(2003)). Domains or motifs may also be identified using routine techniques, such as by sequence alignment.

Methods for the alignment of sequences for comparison are well known in the art, such methods include GAP, BESTFIT, BLAST, FASTA and TFASTA. GAP uses the algorithm of Needleman and Wunsch ((1970) J Mol Biol 48: 443-453) to find the global (i.e. spanning the complete sequences) alignment of two sequences that maximizes the number of matches and minimizes the number of gaps. The BLAST algorithm (Altschul et al. (1990) J Mol Biol 215: 403-10) calculates percent sequence identity or similarity or homology and performs a statistical analysis of the identity or similarity or homology between the two sequences. The software for performing BLAST analysis is publicly available through the National Centre for Biotechnology Information (NCBI). Homologues may readily be identified using, for example, the ClustalW multiple sequence alignment algorithm (version 1.83), with the default pairwise alignment parameters, and a scoring method in percentage. Global percentages of similarity/homology/identity may also be determined using one of the methods available in the MatGAT software package (Campanella et al., BMC Bioinformatics. 2003 Jul. 10; 4:29. MatGAT: an application that generates similarity/homology/identity matrices using protein or DNA sequences). Minor manual editing may be performed to optimise alignment between conserved motifs, as would be apparent to a person skilled in the art. Furthermore, instead of using full-length sequences for the identification of homologues, specific domains may also be used. The sequence identity values may be determined over the entire nucleic acid or amino acid sequence or over selected domains or conserved motif(s), using the programs mentioned above using the default parameters. For local alignments, the Smith-Waterman algorithm is particularly useful (Smith T F, Waterman M S (1981) J. Mol. Biol 147(1); 195-7).

As used herein the terms "fungal-resistance", "resistant to a fungus" and/or "fungal-resistant" mean reducing, preventing, or delaying an infection by *fungi*. The term "resistance" refers to fungal resistance. Resistance does not imply that the plant necessarily has 100% resistance to infection. In preferred embodiments, enhancing or increasing fungal resistance means that resistance in a resistant plant is greater than 10%, greater than 20%, greater than 30%, greater than 40%, greater than 50%, greater than 60%, greater than 70%, greater than 80%, greater than 90%, or greater than 95% in comparison to a wild type plant.

As used herein the terms "soybean rust-resistance", "resistant to a soybean rust", "soybean rust-resistant", "rust-resistance", "resistant to a rust", or "rust-resistant" mean reducing or preventing or delaying an infection of a plant, plant part, or plant cell by Phakopsoraceae, in particular *Phakopsora pachyrhizi* and *Phakopsora meibomiae*—also known as soybean rust or Asian Soybean Rust (ASR), as compared to a wild type plant, wild type plant part, or wild type plant cell. Resistance does not imply that the plant necessarily has 100% resistance to infection. In preferred embodiments, enhancing or increasing rust resistance means that rust resistance in a resistant plant is greater than 10%, greater than 20%, greater than 30%, greater than 40%, greater than 50%, greater than 60%, greater than 70%, greater than 80%, greater than 90%, or greater than 95% in comparison to a wild type plant that is not resistant to soybean rust. Preferably the wild type plant is a plant of a similar, more preferably identical, genotype as the plant having increased resistance to the soybean rust, but does not comprise an exogenous RLK1 nucleic acid, functional fragments thereof and/or an exogenous nucleic acid capable of hybridizing with an RLK1 nucleic acid.

The level of fungal resistance of a plant can be determined in various ways, e.g. by scoring/measuring the infected leaf area in relation to the overall leaf area. Another possibility to determine the level of resistance is to count the number of soybean rust colonies on the plant or to measure the amount of spores produced by these colonies. Another way to resolve the degree of fungal infestation is to specifically measure the amount of rust DNA by quantitative (q) PCR. Specific probes and primer sequences for most fungal pathogens are available in the literature (Frederick R D, Snyder C L, Peterson G L, et al. 2002 Polymerase chain reaction assays for the detection and discrimination of the rust pathogens *Phakopsora pachyrhizi* and *P. meibomiae*, Phytopathology 92(2) 217-227).

The term "hybridization" as used herein includes "any process by which a strand of nucleic acid molecule joins with a complementary strand through base pairing" (J. Coombs (1994) Dictionary of Biotechnology, Stockton Press, New York). Hybridization and the strength of hybridization (i.e., the strength of the association between the nucleic acid molecules) is impacted by such factors as the degree of complementarity between the nucleic acid molecules, stringency of the conditions involved, the Tm of the formed hybrid, and the G:C ratio within the nucleic acid molecules.

As used herein, the term "Tm" is used in reference to the "melting temperature." The melting temperature is the temperature at which a population of double-stranded nucleic acid molecules becomes half dissociated into single strands. The equation for calculating the Tm of nucleic acid molecules is well known in the art. As indicated by standard references, a simple estimate of the Tm value may be calculated by the equation: Tm=81.5+0.41(% G+C), when a nucleic acid molecule is in aqueous solution at 1 M NaCl (see e.g., Anderson and Young, Quantitative Filter Hybridization, in Nucleic Acid Hybridization (1985). Other references include more sophisticated computations, which take structural as well as sequence characteristics into account for the calculation of Tm. Stringent conditions, are known to those skilled in the art and can be found in Current Protocols in Molecular Biology, John Wiley & Sons, N.Y. (1989), 6.3.1-6.3.6.

In particular, the term "stringency conditions" refers to conditions, wherein 100 contiguous nucleotides or more, 150 contiguous nucleotides or more, 200 contiguous nucleotides or more or 250 contiguous nucleotides or more which are a fragment or identical to the complementary nucleic acid molecule (DNA, RNA, ssDNA or ssRNA) hybridizes under conditions equivalent to hybridization in 7% sodium dodecyl sulfate (SDS), 0.5 M NaPO4, 1 mM EDTA at 50° C. with washing in 2×SSC, 0.1% SDS at 50° C. or 65° C., preferably at 65° C., with a specific nucleic acid molecule (DNA; RNA, ssDNA or ssRNA). Preferably, the hybridizing conditions are equivalent to hybridization in 7% sodium dodecyl sulfate (SDS), 0.5 M Na—PO4, 1 mM EDTA at 50° C. with washing in 1×SSC, 0.1% SDS at 50° C. or 65° C., preferably 65° C., more preferably the hybridizing conditions are equivalent to hybridization in 7% sodium dodecyl sulfate (SDS), 0.5 M NaPO4, 1 mM EDTA at 50° C. with washing in 0.1×SSC, 0.1% SDS at 50° C. or 65° C., preferably 65° C. Preferably, the complementary nucleotides hybridize with a fragment or the whole RLK1 nucleic acids.

Alternatively, preferred hybridization conditions encompass hybridisation at 65° C. in 1×SSC or at 42° C. in 1×SSC and 50% formamide, followed by washing at 65° C. in 0.3×SSC or hybridisation at 50° C. in 4×SSC or at 40° C. in 6×SSC and 50% formamide, followed by washing at 50° C. in 2×SSC. Further preferred hybridization conditions are 0.1% SDS, 0.1 SSD and 65° C.

"Identity" or "homology" or "similarity" between two nucleic acids sequences or amino acid sequences refers in each case over the entire length of the RLK1 nucleic acid sequences or RLK1 amino acid sequences. The terms "identity", "homology" and "similarity" are used herein interchangeably.

Preferably, "percentage of sequence identity" is calculated by comparing two optimally aligned sequences over a particular region, determining the number of positions at which the identical base or amino acid occurs in both sequences in order to yield the number of matched positions, dividing the number of such positions by the total number of positions in the region being compared and multiplying the result by 100.

For example the identity may be calculated by means of the Vector NTI Suite 7.1 program of the company Informax (USA) employing the Clustal Method (Higgins D G, Sharp P M. Fast and sensitive multiple sequence alignments on a microcomputer. Comput Appl. Biosci. 1989 Apr.; 5(2):151-1) with the following settings:

Multiple alignment parameter:

| | |
|---|---|
| Gap opening penalty | 10 |
| Gap extension penalty | 10 |
| Gap separation penalty range | 8 |
| Gap separation penalty | off |
| % identity for alignment delay | 40 |
| Residue specific gaps | off |
| Hydrophilic residue gap | off |
| Transition weighing | 0 |

Pairwise alignment parameter:

| | |
|---|---|
| FAST algorithm | on |
| K-tuple size | 1 |
| Gap penalty | 3 |
| Window size | 5 |
| Number of best diagonals | 5 |

Alternatively the identity may be determined according to Chenna, Ramu, Sugawara, Hideaki, Koike, Tadashi, Lopez, Rodrigo, Gibson, Toby J, Higgins, Desmond G, Thompson, Julie D. Multiple sequence alignment with the Clustal series of programs. (2003) Nucleic Acids Res 31 (13):3497-500, the web page: http://www.ebi.ac.uk/Tools/clustalw/index-.html# and the following settings

| | |
|---|---|
| DNA Gap Open Penalty | 15.0 |
| DNA Gap Extension Penalty | 6.66 |
| DNA Matrix | Identity |
| Protein Gap Open Penalty | 10.0 |
| Protein Gap Extension Penalty | 0.2 |
| Protein matrix | Gonnet |
| Protein/DNA ENDGAP | −1 |
| Protein/DNA GAPDIST | 4 |

All the nucleic acid sequences mentioned herein (single-stranded and double-stranded DNA and RNA sequences, for example cDNA and mRNA) can be produced in a known way by chemical synthesis from the nucleotide building blocks, e.g. by fragment condensation of Individual overlapping, complementary nucleic acid building blocks of the double helix. Chemical synthesis of oligonucleotides can, for example, be performed in a known way, by the phosphoamidite method (Voet, Voet, 2nd edition, Wiley Press, New York, pages 896-897). The accumulation of synthetic oligonucleotides and filling of gaps by means of the Klenow fragment of DNA polymerase and ligation reactions as well as general cloning techniques are described in Sambrook et al. (1989), see below.

Sequence identity between the nucleic acid or protein useful according to the present invention and the RLK1 nucleic acids or RLK1 proteins may be optimized by sequence comparison and alignment algorithms known in the art (see Gribskov and Devereux, Sequence Analysis Primer, Stockton Press, 1991, and references cited therein) and calculating the percent difference between the nucleotide or protein sequences by, for example, the Smith-Waterman algorithm as implemented in the BESTFIT software program using default parameters (e.g., University of Wisconsin Genetic Computing Group).

The term "plant" is intended to encompass plants at any stage of maturity or development, as well as any tissues or organs (plant parts) taken or derived from any such plant unless otherwise clearly indicated by context. Plant parts include, but are not limited to, plant cells, stems, roots, flowers, ovules, stamens, seeds, leaves, embryos, meristematic regions, callus tissue, anther cultures, gametophytes, sporophytes, pollen, microspores, protoplasts, hairy root cultures, and/or the like. The present invention also includes seeds produced by the plants of the present invention. Preferably, the seeds comprise the exogenous RLK1 nucleic acids. In one embodiment, the seeds can develop into plants with increased resistance to fungal infection as compared to a wild-type variety of the plant seed. As used herein, a "plant cell" Includes, but is not limited to, a protoplast, gamete producing cell, and a cell that regenerates into a whole plant. Tissue culture of various tissues of plants and regeneration of plants therefrom is well known in the art and is widely published.

Reference herein to an "endogenous" nucleic acid and/or protein refers to the nucleic acid and/or protein in question as found in a plant in its natural form (i.e., without there being any human intervention).

The term "exogenous" nucleic acid refers to a nucleic acid that has been introduced in a plant by means of genetechnology. An "exogenous" nucleic acid can either not occur in a plant in its natural form, be different from the nucleic acid in question as found in a plant in its natural form, or can be identical to a nucleic acid found in a plant in its natural form, but Integrated not within their natural genetic environment. The corresponding meaning of "exogenous" is applied in the context of protein expression. For example, a transgenic plant containing a transgene, i.e., an exogenous nucleic acid, may, when compared to the expression of the endogenous gene, encounter a substantial increase of the expression of the respective gene or protein in total. A transgenic plant according to the present invention includes an exogenous RLK1 nucleic acid integrated at any genetic loci and optionally the plant may also include the endogenous gene within the natural genetic background.

For the purposes of the invention, "recombinant" means with regard to, for example, a nucleic acid sequence, a nucleic acid molecule, an expression cassette or a vector construct comprising any one or more RLK1 nucleic acids, all those constructions brought about by man by genetechnological methods in which either (a) the sequences of the RLK1 nucleic acids or a part thereof, or
(b) genetic control sequence(s) which is operably linked with the RLK1 nucleic acid sequence according to the invention, for example a promoter, or
(c) a) and b)

are not located in their natural genetic environment or have been modified by man by genetechnological methods. The modification may take the form of, for example, a substitution, addition, deletion, inversion or insertion of one or more nucleotide residues. The natural genetic environment is understood as meaning the natural genomic or chromosomal locus in the original plant or the presence in a genomic library or the combination with the natural promoter.

A recombinant nucleic acid, expression cassette or vector construct preferably comprises a natural gene and a natural promoter, a natural gene and a non-natural promoter, a non-natural gene and a natural promoter, or a non-natural gene and a non-natural promoter.

In the case of a genomic library, the natural genetic environment of the nucleic acid sequence is preferably retained, at least in part. The environment flanks the nucleic acid sequence at least on one side and has a sequence length of at least 50 bp, preferably at least 500 bp, especially preferably at least 1000 bp, most preferably at least 5000 bp.

A naturally occurring expression cassette—for example the naturally occurring combination of the natural promoter of the nucleic acid sequences with the corresponding nucleic acid sequence encoding a protein useful in the methods of the present invention, as defined above—becomes a recombinant expression cassette when this expression cassette is modified by man by non-natural, synthetic ("artificial") methods such as, for example, mutagenic treatment. Suitable methods are described, for example, in U.S. Pat. No. 5,565,350, WO 00/15815 or US200405323. Furthermore, a naturally occurring expression cassette—for example the naturally occurring combination of the natural promoter of the nucleic acid sequences with the corresponding nucleic acid sequence encoding a protein useful in the methods of the present invention, as defined above—becomes a recombinant expression cassette when this expression cassette is not integrated in the natural genetic environment but in a different genetic environment.

The term "isolated nucleic acid" or "isolated protein" refers to a nucleic acid or protein that is not located in its natural environment, in particular its natural cellular environment. Thus, an isolated nucleic acid or isolated protein is essentially separated from other components of its natural environment. However, the skilled person in the art is aware that preparations of an isolated nucleic acid or an isolated protein can display a certain degree of impurity depending on the isolation procedure used. Methods for purifying nucleic acids and proteins are well known in the art. The isolated gene may be isolated from an organism or may be manmade, for example by chemical synthesis. In this regard, a recombinant nucleic acid may also be in an isolated form.

As used herein, the term "transgenic" refers to an organism, e.g., a plant, plant cell, callus, plant tissue, or plant part that exogenously contains the nucleic acid, recombinant construct, vector or expression cassette described herein or a part thereof which is preferably introduced by non-essentially biological processes, preferably by Agrobacteria transformation. The recombinant construct or a part thereof is stably integrated into a chromosome, so that it is passed on to successive generations by clonal propagation, vegetative propagation or sexual propagation. Preferred successive generations are transgenic too. Essentially biological processes may be crossing of plants and/or natural recombination.

A transgenic plant, plants cell or tissue for the purposes of the invention is thus understood as meaning that an exogenous RLK1 nucleic acid, recombinant construct, vector or expression cassette including one or more RLK1 nucleic acids is integrated into the genome by means of genetechnology.

Preferably, constructs or vectors or expression cassettes are not present in the genome of the original plant or are present in the genome of the transgenic plant not at their natural locus of the genome of the original plant.

A "wild type" plant, "wild type" plant part, or "wild type" plant cell means that said plant, plant part, or plant cell does not express exogenous RLK1 nucleic acid or exogenous RLK1 protein.

Natural locus means the location on a specific chromosome, preferably the location between certain genes, more preferably the same sequence background as in the original plant which is transformed.

Preferably, the transgenic plant, plant cell or tissue thereof expresses the RLK1 nucleic acids, RLK1 constructs or RLK1 expression cassettes described herein.

The term "expression" or "gene expression" means the transcription of a specific gene or specific genes or specific genetic vector construct. The term "expression" or "gene expression" in particular means the transcription of a gene or genes or genetic vector construct into structural RNA (rRNA, tRNA), or mRNA with or without subsequent translation of the latter into a protein. The process includes transcription of DNA and processing of the resulting RNA product. The term "expression" or "gene expression" can also include the translation of the mRNA and therewith the synthesis of the encoded protein, i.e., protein expression.

The term "increased expression" or "enhanced expression" or "overexpression" or "increase of content" as used herein means any form of expression that is additional to the original wild-type expression level. For the purposes of this invention, the original wild-type expression level might also be zero (absence of expression).

Methods for increasing expression of genes or gene products are well documented in the art and include, for example, overexpression driven by appropriate promoters, the use of transcription enhancers or translation enhancers. Isolated nucleic acids which serve as promoter or enhancer elements may be introduced in an appropriate position (typically upstream) of a non-heterologous form of a polynucleotide so as to upregulate expression of a nucleic acid encoding the protein of interest. For example, endogenous promoters may be altered in vivo by mutation, deletion, and/or substitution (see, Kmiec, U.S. Pat. No. 5,565,350; Zarling et al., WO9322443), or isolated promoters may be introduced into a plant cell in the proper orientation and distance from a gene of the present invention so as to control the expression of the gene.

If protein expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added may be derived from, for example, the nopaline synthase or octopine synthase genes, or alternatively from another plant gene, or less preferably from any other eukaryotic gene.

An intron sequence may also be added to the 5' untranslated region (UTR) and/or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg (1988) Mol. Cell biol. 8: 4395-4405; Callis et al. (1987) Genes Dev 1:1183-1200). Such intron enhancement of gene expression is typically greatest when placed near the 5' end of the transcription unit. Use of the maize introns Adh1-S intron 1, 2, and 6, the Bronze-1 intron are known in the art. For general information see: The Maize Handbook, Chapter 116, Freeling and Walbot, Eds., Springer, N.Y. (1994).

The term "functional fragment" refers to any nucleic acid or protein which comprises merely a part of the full length nucleic acid or full length protein, respectively, but still provides the same function, e.g., fungal resistance, when expressed or repressed in a plant, respectively. Preferably, the fragment comprises at least 50%, at least 60%, at least 70%, at least 80%, at least 90% at least 95%, at least 98%, at least 99% of the original sequence. Preferably, the functional fragment comprises contiguous nucleic acids or amino acids as in the original nucleic acid or original protein, respectively. In one embodiment the fragment of any of the RLK1 nucleic acids has an identity as defined above over a length of at least 20%, at least 30%, at least 50%, at least 75%, at least 90% of the nucleotides of the respective RLK1 nucleic acid.

The term "splice variant" as used herein encompasses variants of a nucleic acid sequence in which selected introns and/or exons or parts thereof have been excised, replaced, displaced or added, or in which introns have been shortened or lengthened. Thus, a splice variant can have one or more or even all introns removed or added or partially removed or partially added. According to this definition, a cDNA is considered as a splice variant of the respective intron-containing genomic sequence and vice versa. Such splice variants may be found in nature or may be manmade. Methods for predicting and isolating such splice variants are well known in the art (see for example Foissac and Schiex (2005) BMC Bioinformatics 6:25).

In cases where overexpression of nucleic acid is desired, the term "similar functional activity" or "similar function" means that any homologue and/or fragment provide fungal resistance when expressed in a plant. Preferably similar functional activity means at least 50%, at least 60%, at least 70%, at least 80%, at least 90%, at least 95%, at least 98%, at least 99% or 100% or higher fungal resistance compared with functional activity provided by the exogenous expression of the RLK1 nucleotide sequence as defined by SEQ ID NO: 1 or the RLK1 protein sequence as defined by SEQ ID NO: 2.

The term "Increased activity" or "enhanced activity" as used herein means any protein having increased activity and which provides an increased fungal resistance compared with the wildtype plant merely expressing the respective endogenous RLK1 nucleic acid. As far as overexpression is concerned, for the purposes of this invention, the original wild-type expression level might also be zero (absence of expression).

With respect to a vector construct and/or the recombinant nucleic acid molecules, the term "operatively linked" is intended to mean that the nucleic acid to be expressed is linked to the regulatory sequence, including promoters, terminators, enhancers and/or other expression control elements (e.g., polyadenylation signals), in a manner which allows for expression of the nucleic acid (e.g., in a host plant cell when the vector is introduced into the host plant cell). Such regulatory sequences are described, for example, in Goeddel, Gene Expression Technology: Methods in Enzymology 185, Academic Press, San Diego, Calif. (1990) and Gruber and Crosby, in: Methods in Plant Molecular Biology and Biotechnology, Eds. Glick and Thompson, Chapter 7, 89-108, CRC Press: Boca Raton, Fla., including the references therein. Regulatory sequences include those that direct constitutive expression of a nucleotide sequence in many types of host cells and those that direct expression of the nucleotide sequence only in certain host cells or under certain conditions. It will be appreciated by those skilled in the art that the design of the vector can depend on such factors as the choice of the host cell to be transformed, the level of expression of nucleic acid desired, and the like.

The term "introduction" or "transformation" as referred to herein encompass the transfer of an exogenous polynucleotide into a host cell, irrespective of the method used for transfer. Plant tissue capable of subsequent clonal propagation, whether by organogenesis or embryogenesis, may be transformed with a vector construct of the present invention and a whole plant regenerated there from. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. The host genome includes the nucleic acid contained in the nucleus as well as the nucleic acid contained in the plastids, e.g., chloroplasts, and/or mitochondria. The resulting transformed plant cell may then be used to regenerate a transformed plant in a manner known to persons skilled in the art.

The term "terminator" encompasses a control sequence which is a DNA sequence at the end of a transcriptional unit which signals 3' processing and polyadenylation of a primary transcript and termination of transcription. The terminator can be derived from the natural gene, from a variety of other plant genes, or from T-DNA. The terminator to be added may be derived from, for example, the nopaline synthase or octopine synthase genes, or alternatively from another plant gene, or less preferably from any other eukaryotic gene.

DETAILED DESCRIPTION

RLK1 Nucleic Acids

The RLK1 nucleic acid to be overexpressed in order to achieve increased resistance to fungal pathogens, e.g., of the family Phakopsoraceae, for example soybean rust, is preferably a nucleic acid coding for an RLK1 protein, and is preferably as defined by SEQ ID NO: 9, 1, 3, 11-18, 19, 21, 23, 25, 27, 29, 31, or 33, or a fragment, homolog, derivative, orthologue or paralogue thereof, or a splice variant thereof. Preferably, the nucleic acid coding for an RLK1 protein of the present invention has at least 60% identity, preferably at least 70% sequence identity, at least 80%, at least 90%, at least 95%, at least 98%, at least 99% sequence identity, or even 100% sequence identity with SEQ ID NO: 9, 1, 3, 11-18, 19, 21, 23, 25, 27, 29, 31, or 33, or is a functional fragment thereof, or a splice variant thereof. Most preferred is at least 90% identity, at least 95% identity, more preferred is at least 98% or at least 99% identity with SEQ ID NO: 9, 1, 3, 11-18, 19, 21, 23, 25, 27, 29, 31, or 33.

Preferably, the RLK1 nucleic acid to be overexpressed in order to achieve increased resistance to fungal pathogens, e.g., of the family Phakopsoraceae, for example soybean rust, is preferably a nucleic acid coding for a RLK1 protein, and is preferably as defined by SEQ ID NO: 3, or a fragment, homolog, derivative, orthologue or paralogue thereof, or a splice variant thereof. Preferably, the nucleic add coding for a RLK1 protein of the present Invention has at least 60% Identity, preferably at least 70% sequence identity, at least 80%, at least 90%, at least 95%, at least 98%, at least 99% sequence identity, or even 100% sequence identity with SEQ ID NO: 3 or is a functional fragment thereof, or a splice variant thereof. Most preferred is at least 90% identity, at least 95% identity, more preferred is at least 98% or at least 99% identity with SEQ ID NO: 3.

More preferably, the RLK1 nucleic add to be overexpressed in order to achieve increased resistance to fungal pathogens, e.g., of the family Phakopsoraceae, for example soybean rust, is preferably a nucleic acid coding for a RLK1 protein, and is preferably as defined by SEQ ID NO: 1, or a fragment, homolog, derivative, orthologue or paralogue thereof, or a splice variant thereof. Preferably, the nucleic add coding for a RLK1 protein of the present invention has at least 60% identity, preferably at least 70% sequence identity, at least 80%, at least 90%, at least 95%, at least 98%, at least 99% sequence identity, or even 100% sequence identity with SEQ ID NO: 1 or is a functional fragment thereof, or a splice variant thereof. Most preferred is at least 95% identity, more preferred is at least 98% or at least 99% identity with SEQ ID NO: 1.

More preferably, the RLK1 nucleic acid to be overexpressed in order to achieve increased resistance to fungal pathogens, e.g., of the family Phakopsoraceae, for example soybean rust, is preferably a nucleic add coding for a RLK1 protein, and is preferably as defined by SEQ ID NO: 9, or a fragment, homolog, derivative, orthologue or paralogue thereof, or a splice variant thereof. Preferably, the nucleic add coding for a RLK1 protein of the present invention has at least 60% identity, preferably at least 70% sequence identity, at least 80%, at least 90%, at least 95%, at least 98%, at least 99% sequence identity, or even 100% sequence identity with SEQ ID NO: 9 or is a functional fragment thereof, or a splice variant thereof. Most preferred is at least 95% identity, more preferred is at least 98% or at least 99% identity with SEQ ID NO: 9.

SEQ ID NO: 9 corresponds to SEQ ID NO: 1, wherein in SEQ ID NO: 9 a couple of nucleotides have been exchanged.

More preferably, the RLK1 nucleic acid to be overexpressed in order to achieve increased resistance to fungal pathogens, e.g., of the family Phakopsoraceae, for example soybean rust, is preferably a nucleic add coding for a RLK1 protein, and is preferably as defined by SEQ ID NO: 8, or a fragment, homolog, derivative, orthologue or paralogue thereof, or a splice variant thereof. Preferably, the nucleic add coding for a RLK1 protein of the present invention has at least 60% Identity, preferably at least 70% sequence identity, at least 80%, at least 90%, at least 95%, at least 98%, at least 99% sequence identity, or even 100% sequence identity with SEQ ID NO: 8 or is a functional fragment thereof, or a splice variant thereof. Most preferred is at least 95% identity, more preferred is at least 98% or at least 99% identity with SEQ ID NO: 8.

Preferably the RLK1 nucleic acid is an isolated nucleic acid molecule consisting of or comprising a nucleic acid selected from the group consisting of:

(i) a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 9, 1, 3, 8, 11-18, 19, 21, 23, 25, 27, 29, 31, or 33, or a functional fragment, derivative, orthologue, or paralogue thereof, or a splice variant thereof;

(ii) a nucleic acid encoding a RLK1 protein having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 10, 2, 20, 22, 24, 26, 28, 30, 32, or 34, or a functional fragment, derivative, orthologue, or paralogue thereof; preferably the RLK1 protein has essentially the same biological activity as a RLK1 protein encoded by SEQ ID NO: 9, 1, 3, 8, 11-18, 19, 21, 23, 25, 27, 29, 31, or 33; preferably the RLK1 protein confers enhanced fungal resistance relative to control plants; preferably the RLK1 protein has receptor like kinase activity;

(iii) a nucleic acid molecule which hybridizes with a complementary sequence of any of the nucleic acid molecules of (i) or (ii) under high stringency hybridization conditions; preferably encoding a RLK1 protein; preferably wherein the nucleic acid molecule codes for a polypeptide which has essentially identical properties to the polypeptide described in SEQ ID NO: 10, 2, 20, 22, 24, 26, 28, 30, 32, or 34; preferably the encoded protein confers enhanced fungal resistance relative to control plants; and (iv) a nucleic acid encoding the same RLK1 protein as the RLK1 nucleic acids of (i) to (ii) above, but differing from the RLK1 nucleic acids of (i) to (ii) above due to the degeneracy of the genetic code.

Preferably, the nucleic acid coding for a RLK1 protein of the present invention has at least 60% identity, preferably at least 70% sequence identity, at least 80%, at least 90%, at least 95%, at least 98%, at least 99% sequence identity, or even 100% sequence identity with SEQ ID NO: 1. Most preferred is at least 95% identity, more preferred is at least 98% or at least 99% identity with SEQ ID NO: 1.

Preferably, the nucleic acid coding for a RLK1 protein of the present invention has at least 60% identity, preferably at least 70% sequence identity, at least 80%, at least 90%, at least 95%, at least 98%, at least 99% sequence identity, or even 100% sequence identity with SEQ ID NO: 9. Most preferred is at least 95% identity, more preferred is at least 98% or at least 99% identity with SEQ ID NO: 9.

Preferably the RLK1 nucleic acid is an isolated nucleic acid molecule consisting of or comprising a nucleic acid selected from the group consisting of:

(i) a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 1, or a functional fragment, derivative, orthologue, or paralogue thereof, or a splice variant thereof;

(ii) a nucleic acid encoding a RLK1 protein having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 2, or a functional fragment, derivative, orthologue, or paralogue thereof; preferably the RLK1 protein has essentially the same biological activity as a RLK1 protein encoded by SEQ ID NO: 1, preferably the RLK1 protein confers enhanced fungal resistance relative to control plants;

(iii) a nucleic acid molecule which hybridizes with a complementary sequence of any of the nucleic acid molecules of (i) or (ii) under high stringency hybridization conditions; preferably encoding a RLK1 protein; preferably wherein the nucleic acid molecule codes for a polypeptide which has essentially identical properties to the polypeptide described in SEQ ID NO: 10 or 2; preferably the encoded protein confers enhanced fungal resistance relative to control plants; and (iv) a nucleic acid encoding the same RLK1 protein as the RLK1 nucleic acids of (i) to (ii) above, but differing from the RLK1 nucleic acids of (i) to (ii) above due to the degeneracy of the genetic code.

Preferably the RLK1 nucleic acid is an isolated nucleic acid molecule comprising a nucleic acid selected from the group consisting of:

(i) a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 9, or a functional fragment, derivative, orthologue, or paralogue thereof, or a splice variant thereof;

(ii) a nucleic acid encoding a RLK1 protein having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 10, or a functional fragment, derivative, orthologue, or paralogue thereof; preferably the RLK1 protein has essentially the same biological activity as a RLK1 protein encoded by SEQ ID NO: 9 or 1, preferably the RLK1 protein confers enhanced fungal resistance relative to control plants;

(iii) a nucleic acid molecule which hybridizes with a complementary sequence of any of the nucleic acid molecules of (i) or (ii) under high stringency hybridization conditions; preferably encoding a RLK1 protein; preferably wherein the nucleic acid molecule codes for a polypeptide which has essentially identical properties to the polypeptide described in SEQ ID NO: 10 or 2; preferably the encoded protein confers enhanced fungal resistance relative to control plants; and (iv) a nucleic acid encoding the same RLK1 protein as the RLK1 nucleic acids of (i) to (ii) above, but differing from the RLK1 nucleic acids of (i) to (ii) above due to the degeneracy of the genetic code.

Percentages of identity of a nucleic acid are indicated with reference to the entire nucleotide region given in a sequence specifically disclosed herein.

Preferably the portion of the RLK1 nucleic acid is about 1500-1600, about 1600-1700, about 1700-1800, about 1800-1900, about 1900-1995, about 1900-2000, about 2000-2200, about 2200-2400, about 2400-2600, about 2600-2800, about 2800-3000, about 3000-3200, about 3200-3400, about 3400-3600, about 3600-3800, about 3800-4000, about 4000-4200, about 4200-4400, or about 4400-4622 nucleotides, preferably consecutive nucleotides, preferably counted from the 5' or 3' end of the nucleic acid, in length, of the nucleic acid sequences given in SEQ ID NO: 1, 3, 8, 9, 11-18, 19, 21, 23, 25, 27, 29, 31, or 33.

Preferably, the RLK1 nucleic acid comprises at least about 1500, at least about 1600, at least about 1700, at least about 1800, at least about 1900, at least about 2000, at least about 2200, at least about 2400, at least about 2600, at least about 2800, at least about 3000, at least about 3200, at least about 3400, at least about 3600, at least about 3800, at least about 4000, at least about 4200, at least about 4400, or at least about 4600 nucleotides, preferably continuous nucleotides, preferably counted from the 5' or 3' end of the nucleic acid or up to the full length of the nucleic acid sequence set out in SEQ ID NO: 1, 3, 8, 9, 11-18, 19, 21, 23, 25, 27, 29, 31, or 33.

Preferably, the RLK1 nucleic acid comprises at least about 1000, at least about 1200, at least about 1400, at least about 1600, at least about 1800, at least about 1900 nucleotides, preferably continuous nucleotides, preferably counted from the 5' or 3' end of the nucleic acid or up to the full length of the nucleic acid sequence set out in SEQ ID NO: 1, 11-18, 19, 21, 23, 25, 27, 29, 31, or 33.

Preferably the portion of the RLK1 nucleic acid is about 1000-1100, about 1100-1200, about 1200-1300, about 1300-1400, about 1400-1500, about 1500-1600, about 1600-1700, about 1700-1800, about 1800-1995 nucleotides, preferably consecutive nucleotides, preferably counted from the 5' or 3' end of the nucleic acid, in length, of the nucleic acid sequences given in SEQ ID NO: 1, 11-18, 19, 21, 23, 25, 27, 29, 31, or 33.

Preferably, the RLK1 nucleic acid comprises at least about 1000, at least about 1200, at least about 1400, at least about 1600, at least about 1800, at least about 1900 nucleotides, preferably continuous nucleotides, preferably counted from the 5' or 3' end of the nucleic acid or up to the full length of the nucleic acid sequence set out in SEQ ID NO: 9.

Preferably the portion of the RLK1 nucleic acid is about 1000-1100, about 1100-1200, about 1200-1300, about 1300-1400, about 1400-1500, about 1500-1600, about 1600-1700, about 1700-1800, about 1800-1995 nucleotides, preferably consecutive nucleotides, preferably counted from the 5' or 3' end of the nucleic acid, in length, of the nucleic acid sequences given in SEQ ID NO: 9.

Preferably, the RLK1 nucleic acid is a RLK1 nucleic acid splice variant. Preferred splice variants are splice variants of a nucleic acid represented by SEQ ID NO: 3. Preferred RLK1 nucleic acids being a splice variant of SEQ ID NO: 3 are shown in FIG. 6.

Preferably, the RLK1 nucleic acid is an isolated nucleic acid molecule comprising a splice variant of SEQ ID NO: 3, wherein the splice variant is selected from the group consisting of:

(i) a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 9 or 1, or a functional fragment, derivative, orthologue, or paralogue thereof;

(ii) a nucleic acid encoding a RLK1 protein having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 10 or 2, or a functional fragment, derivative, orthologue, or paralogue thereof; preferably the RLK1 protein has essentially the same biological activity as a RLK1 protein encoded by SEQ ID NO: 9, 1 or 3; preferably the RLK1 protein confers enhanced fungal resistance relative to control plants;

(iii) a nucleic acid molecule which hybridizes with a complementary sequence of any of the nucleic acid molecules of (i) or (ii) under high stringency hybridization conditions; preferably encoding a RLK1 protein; preferably wherein the nucleic acid molecule codes for a polypeptide which has essentially identical properties to the polypeptide described in SEQ ID NO: 10 or 2; preferably the encoded protein confers enhanced fungal resistance relative to control plants; and (iv) a nucleic acid encoding the same RLK1 protein as the RLK1 nucleic acids of (i) to (ii) above, but differing from the RLK1 nucleic acids of (i) to (ii) above due to the degeneracy of the genetic code.

Preferred splice variants of SEQ ID NO: 3 consist of or comprise the nucleotide sequence shown in SEQ ID NO: 1.

Preferred splice variants of SEQ ID NO: 3 consist of or comprise the nucleotide sequence shown in SEQ ID NO: 9.

Preferably the RLK1 nucleic acid is an isolated nucleic acid molecule comprising a nucleic acid selected from the group consisting of:

(i) a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 3, or a splice variant thereof;

(ii) a nucleic acid molecule which hybridizes with a complementary sequence of any of the nucleic acid molecules of (i) under high stringency hybridization conditions; preferably encoding a RLK1 protein; preferably wherein the nucleic acid molecule codes for a polypeptide which has essentially identical properties to the polypeptide described in SEQ ID NO: 10 or 2; preferably the encoded protein confers enhanced fungal resistance relative to control plants;

(iii) a nucleic acid encoding the same RLK1 protein as the RLK1 nucleic acids of (i) to (ii) above, but differing from the RLK1 nucleic acids of (i) to (ii) above due to the degeneracy of the genetic code;

wherein the splice variant is selected from the group consisting of:

(i) a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 1, or a functional fragment, derivative, orthologue, or paralogue thereof;

(ii) a nucleic acid encoding a RLK1 protein having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 2, or a functional fragment, derivative, orthologue, or paralogue thereof; preferably the RLK1 protein has essentially the same biological activity as a RLK1 protein encoded by SEQ ID NO: 1 or 3; preferably the RLK1 protein confers enhanced fungal resistance relative to control plants;

(iii) a nucleic acid molecule which hybridizes with a complementary sequence of any of the nucleic acid molecules of (i) or (ii) under high stringency hybridization conditions; preferably encoding a RLK1 protein; preferably wherein the nucleic acid molecule codes for a polypeptide which has essentially identical properties to the polypeptide described in SEQ ID NO: 10 or 2; preferably the encoded protein confers enhanced fungal resistance relative to control plants; and (iv) a nucleic acid encoding the same RLK1 protein as the RLK1 nucleic acids of (i) to (ii) above, but differing from the RLK1 nucleic acids of (i) to (ii) above due to the degeneracy of the genetic code.

More preferably the RLK1 nucleic acid is an isolated nucleic acid molecule comprising a nucleic acid selected from the group consisting of:
a nucleic acid having in increasing order of preference least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 3, or a splice variant thereof; wherein the splice variant thereof has in increasing order of preference at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 1.

More preferably the RLK1 nucleic acid is an isolated nucleic acid molecule comprising a nucleic acid selected from the group consisting of:
a nucleic acid having in increasing order of preference least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 3, or a splice variant thereof; wherein the splice variant thereof has in increasing order of preference at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 9.

The RLK1 nucleic acids described herein are useful in the constructs, methods, plants, harvestable parts and products of the invention.

RLK1 Proteins

The RLK1 protein is preferably defined by SEQ ID NO: 10, 2, 20, 22, 24, 26, 28, 30, 32, or 34, or a fragment, homolog, derivative, orthologue or paralogue thereof. Preferably, the RLK1 protein of the present invention is encoded by a nucleic acid, which has at least 60% Identity, preferably at least 70% sequence identity, at least 80%, at least 90%, at least 95%, at least 98%, at least 99% sequence identity, or even 100% sequence identity with SEQ ID NO: 10, 2, 20, 22, 24, 26, 28, 30, 32, or 34 or a functional fragment thereof. More preferably, the RLK1 protein of the present invention has at least 60%, preferably at least 70% sequence identity, at least 80%, at least 90%, at least 95%, at least 98%, at least 99% sequence identity, or even 100% sequence identity with SEQ ID NO: 10, 2, 20, 22, 24, 26, 28, 30, 32, or 34, or is a functional fragment thereof, an orthologue or a paralogue thereof. Most preferred is at least 90% identity, least 95% identity, more preferred is at least 98% or at least 99% identity with SEQ ID NO: 10, 2, 20, 22, 24, 26, 28, 30, 32, or 34.

Preferably, the RLK1 protein is a protein consisting of or comprising an amino acid sequence selected from the group consisting of:

(i) an amino acid sequence having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 10, 2, 20, 22, 24, 26, 28, 30, 32, or 34, or a functional fragment, derivative, orthologue, or paralogue thereof; preferably the RLK1 protein has essentially the same biological activity as a RLK1 protein encoded by SEQ ID NO: 9, 1, 3, 8, 11-18, 19, 21, 23, 25, 27, 29, 31, or 33; preferably the RLK1 protein confers enhanced fungal resistance relative to control plants; preferably the RLK1 protein has receptor like kinase activity; or (ii) an amino acid sequence encoded by a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 9, 1, 3, 8, 11-18, 19, 21, 23, 25, 27, 29, 31, or 33, or a functional fragment, derivative, orthologue, or paralogue thereof, or a splice variant thereof; preferably the RLK1 protein confers enhanced fungal resistance relative to control plants; preferably the RLK2 protein has receptor like kinase activity.

Preferably, the RLK1 protein is a protein comprising an amino acid sequence selected from the group consisting of:

(i) an amino acid sequence having in increasing order of preference at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 10 or 2, or a functional fragment, derivative, orthologue, or paralogue thereof; preferably the RLK1 protein has essentially the same biological activity as a RLK1 protein encoded by SEQ ID NO: 9, 1, or 3; preferably the RLK1 protein confers enhanced fungal resistance relative to control plants; or (ii) an amino acid sequence encoded by a nucleic acid having in increasing order of preference at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 1, or a functional fragment, derivative, orthologue, or paralogue thereof, or a splice variant thereof; preferably the RLK1 protein confers enhanced fungal resistance relative to control plants.

Preferably, the RLK1 protein is a protein comprising an amino acid sequence selected from the group consisting of:
(i) an amino acid sequence having in increasing order of preference at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 10, or a functional fragment, derivative, orthologue, or paralogue thereof; preferably the RLK1 protein has essentially the same biological activity as a RLK1 protein encoded by SEQ ID NO: 9, 1, or 3; preferably the RLK1 protein confers enhanced fungal resistance relative to control plants; or
(ii) an amino acid sequence encoded by a nucleic acid having in increasing order of preference at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 9, or a functional fragment, derivative, orthologue, or paralogue thereof, or a splice variant thereof; preferably the RLK1 protein confers enhanced fungal resistance relative to control plants.

SEQ ID NO: 10 corresponds to SEQ ID NO: 2, wherein in SEQ ID NO: 10 a couple of amino acid residues have been exchanged.

A preferred derivative of a RLK1 protein is a RLK1 protein consisting of or comprising an amino acid sequence selected from the group consisting of:
an amino acid sequence having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence represented by SEQ ID NO: 10, 2, 20, 22, 24, 26, 28, 30, 32, or 34,
wherein the non-identical amino acid residues are conservative amino acid substitutions, preferably as shown in Table 1, of the corresponding amino acid residue of SEQ ID NO: 10 or 2; preferably the RLK1 protein has essentially the same biological activity as SEQ ID NO: 10 or 2 or as a RLK1 protein encoded by SEQ ID NO: 9, 1, 3, 8, 11-18, 19, 21, 23, 25, 27, 29, 31, or 33; preferably the RLK1 protein confers enhanced fungal resistance relative to control plants.

Preferably, the RLK1 protein consists of or comprises an amino acid sequence represented by SEQ ID NO: 2 with one or more conservative amino acid substitutions, preferably as shown in Table 1, of the corresponding amino acid residues of SEQ ID NO: 2. Preferably 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 1-10, 10-20, 20-30, 40-50, 50-60, 60-70, 70-80, 80-90, 90-100, 100-110, 110-120, or 120-130 amino acid residues of SEQ ID NO: 2 are conservative amino acid substitutions, preferably as shown in Table 1, of the corresponding amino acid residue of SEQ ID NO: 2.

Preferably, the RLK1 protein consists of or comprises an amino acid sequence represented by SEQ ID NO: 10 with one or more conservative amino acid substitutions, preferably as shown in Table 1, of the corresponding amino acid residues of SEQ ID NO: 10. Preferably 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 1-10, 10-20, 20-30, 40-50, 50-60, 60-70, 70-80, 80-90, 90-100, 100-110, 110-120, or 120-130 amino acid residues of SEQ ID NO: 10 are conservative amino acid substitutions, preferably as shown in Table 1, of the corresponding amino acid residue of SEQ ID NO: 10.

More preferably, the RLK1 protein consists of or comprises an amino acid sequence having at least 80%, at least 85%, at least 90%, at least 95%, at least 98% or at least 99% sequence Identity with an amino acid sequence as represented by SEQ ID NO: 10, 2, 20, 22, 24, 26, 28, 30, 32, or 34, wherein at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 of the non-identical amino acid residues, or wherein 1-10, 10-20, 20-30, 40-50, 50-60, 60-70, 70-80, 80-90 or 90-100 or even all of the non-identical amino acid residues are conservative amino acid substitutions, preferably as shown in Table 1, of the corresponding amino acid residue of SEQ ID NO: 10, 2, 20, 22, 24, 26, 28, 30, 32, or 34.

Percentages of identity of a polypeptide or protein are indicated with reference to the entire amino acid sequence specifically disclosed herein.

Preferably, the RLK1 protein comprises at least about 450, at least about 500, at least about 520, at least about 540, at least about 560, at least about 580, at least about 590, at least about 600, at least about 610, at least about 620, at least about 630, at least about 640, at least about 650, or at least about 660 amino acid residues, preferably continuous amino acid residues, preferably counted from the N-terminus or the C-terminus of the amino acid sequence, or up to the full length of the amino acid sequence set out in SEQ ID NO: 10, 2, 20, 22, 24, 26, 28, 30, 32, or 34.

Preferably, the RLK1 polypeptide comprises about 300-400, about 400-500, about 500-520, about 520-540, about 540-560, about 560-580, about 580-590, about 590-600, about 600-610, about 610-620, about 620-630, about 630-640, about 640-650, or about 650-664 amino acids, preferably consecutive amino acids, preferably counted from the N-terminus or C-terminus of the amino acid sequence, or up to the full length of any of the amino acid sequences encoded by the nucleic acid sequences set out in SEQ ID NO: 10, 2, 20, 22, 24, 26, 28, 30, 32, or 34.

Preferably, the RLK1 protein comprises at least about 450, at least about 500, at least about 520, at least about 540, at least about 560, at least about 580, at least about 590, at least about 600, at least about 610, at least about 620, at least about 630, at least about 640, at least about 650, or at least about 660 amino acid residues, preferably continuous amino acid residues, preferably counted from the N-terminus or the C-terminus of the amino acid sequence, or up to the full length of the amino acid sequence set out in SEQ ID NO: 2.

Preferably, the RLK1 polypeptide comprises about 300-400, about 400-500, about 500-520, about 520-540, about 540-560, about 560-580, about 580-590, about 590-600, about 600-610, about 610-620, about 620-630, about 630-640, about 640-650, or about 650-664 amino acids, preferably consecutive amino acids, preferably counted from the N-terminus or C-terminus of the amino acid sequence, or up to the full length of any of the amino acid sequences encoded by the nucleic acid sequences set out in SEQ ID NO: 2.

Preferably, the RLK1 protein comprises at least about 450, at least about 500, at least about 520, at least about 540, at least about 560, at least about 580, at least about 590, at least about 600, at least about 610, at least about 620, at least about 630, at least about 640, at least about 650, or at least about 660 amino acid residues, preferably continuous amino acid residues, preferably counted from the N-terminus or the C-terminus of the amino acid sequence, or up to the full length of the amino acid sequence set out in SEQ ID NO: 10.

Preferably, the RLK1 polypeptide comprises about 300-400, about 400-500, about 500-520, about 520-540, about 540-560, about 560-580, about 580-590, about 590-600, about 600-610, about 610-620, about 620-630, about 630-640, about 640-650, or about 650-664 amino acids, preferably consecutive amino acids, preferably counted from the N-terminus or C-terminus of the amino acid sequence, or up to the full length of any of the amino acid sequences encoded by the nucleic acid sequences set out in SEQ ID NO: 10.

The RLK1 proteins described herein are useful in the constructs, methods, plants, harvestable parts and products of the invention.

Methods for Increasing Fungal Resistance; Methods for Modulating Gene Expression One embodiment of the invention is a method for increasing fungal resistance, preferably resistance to Phakopsoraceae, for example soy bean rust, in a plant, plant part, or plant cell by increasing the expression of an RLK1 protein or a functional fragment, orthologue, paralogue or homologue thereof in comparison to wild-type plants, wild-type plant parts or wild-type plant cells.

The present invention also provides a method for increasing resistance to fungal pathogens, in particular a heminecrotrophic pathogen, in particular to rust pathogens (i.e., fungal pathogens of the order Pucciniales), preferably fungal pathogens of the family Phakopsoraceae, preferably against fungal pathogens of the genus *Phakopsora*, most preferably against *Phakopsora pachyrhizi* and *Phakopsora meibomiae*, also known as soy bean rust in plants or plant cells, wherein in comparison to wild type plants, wild type plant parts, or wild type plant cells an RLK1 protein is overexpressed.

The present invention further provides a method for increasing resistance to fungal pathogens of the genus *Phakopsora*, most preferably against *Phakopsora pachyrhizi* and *Phakopsora meibomiae*, also known as soy bean rust in plants or plant cells by overexpression of an RLK1 protein.

In preferred embodiments, the protein amount and/or function of the RLK1 protein in the plant is increased by at least 10%, at least 20%, at least 30%, at least 40%, at least 50%, at least 60%, at least 70%, at least 80%, at least 90%, or at least 95% or more in comparison to a wild type plant that is not transformed with the RLK1 nucleic acid.

In one embodiment of the invention, the RLK1 protein is encoded by
(i) an exogenous nucleic acid having at least 60%, preferably at least 70%, for example at least 75%, more preferably at least 80%, for example at least 85%, even more preferably at least 90%, for example at least 95% or at least 96% or at least 97% or at least 98% most preferably 99% identity with SEQ ID NO: 9, 1, 3, 8, 11-18, 19, 21, 23, 25, 27, 29, 31, or 33, a functional fragment thereof, or an orthologue or a paralogue thereof, or a splice variant thereof; or by
(ii) an exogenous nucleic acid encoding a protein having at least 60% identity, preferably at least 70%, for example at least 75%, more preferably at least 80%, for example at least 85%, even more preferably at least 90%, for example at least 95% or at least 96% or at least 97% or at least 98% most preferably 99% homology with SEQ ID NO: 10, 2, 20, 22, 24, 26, 28, 30, 32, or 34, a functional fragment thereof, an orthologue or a paralogue thereof, preferably the encoded protein confers enhanced fungal resistance relative to control plants;
(iii) an exogenous nucleic acid capable of hybridizing under stringent conditions with a complementary sequence of any of the nucleic acids according to (i) or (ii), preferably encoding a RLK1 protein; preferably wherein the nucleic acid molecule codes for a polypeptide which has essentially identical properties to the polypeptide described in SEQ ID NO: 10 or 2; preferably the encoded protein confers enhanced fungal resistance relative to control plants; or by
(iv) an exogenous nucleic acid encoding the same RLK1 protein as any of the nucleic acids of (i) to (iii) above, but differing from the nucleic acids of (i) to (iii) above due to the degeneracy of the genetic code.

A method for increasing fungal resistance, preferably resistance to Phakopsoraceae, for example soy bean rust, in a plant, plant part, or plant cell, by increasing the expression of an RLK1 protein or a functional fragment, orthologue, paralogue or homologue thereof, or a splice variant thereof, wherein the RLK1 protein is encoded by
(i) an exogenous nucleic acid having at least 60% identity, preferably at least 70% sequence identity, at least 80%, at least 90%, at least 95%, at least 98%, at least 99% sequence identity, or even 100% sequence identity with SEQ ID NO: 9, 1, 3, 8, 11-18, 19, 21, 23, 25, 27, 29, 31, or 33, a functional fragment thereof, an orthologue or a paralogue thereof, or a splice variant thereof;
(ii) an exogenous nucleic acid encoding a protein having at least 60%, preferably at least 70% sequence identity, at least 80%, at least 90%, at least 95%, at least 98%, at least 99% sequence identity, or even 100% sequence identity with SEQ ID NO: 10, 2, 20, 22, 24, 26, 28, 30, 32, or 34, a functional fragment thereof, an orthologue or a paralogue thereof; preferably the encoded protein confers enhanced fungal resistance relative to control plants;
(iii) an exogenous nucleic acid capable of hybridizing under stringent conditions with a complementary sequence of any of the nucleic acids according to (i) or (ii); preferably encoding a RLK1 protein; preferably wherein the nucleic acid molecule codes for a polypeptide which has essentially identical properties to the polypeptide described in SEQ ID NO: 10 or 2; preferably the encoded protein confers enhanced fungal resistance relative to control plants; and/or by
(iv) an exogenous nucleic acid encoding the same RLK1 protein as any of the nucleic acids of (i) to (iii) above, but differing from the nucleic acids of (i) to (iii) above due to the degeneracy of the genetic code is a further embodiment of the invention.

A method for increasing fungal resistance, preferably resistance to Phakopsoraceae, for example soy bean rust, in a plant, plant part, or plant cell, by increasing the expression of a RLK1 protein or a functional fragment, orthologue, paralogue or homologue thereof, or a splice variant thereof, wherein the RLK1 protein is encoded by
(i) an exogenous nucleic acid having at least 60% identity, preferably at least 70% sequence identity, at least 80%, at least 90%, at least 95%, at least 98%, at least 99% sequence identity, or even 100% sequence identity with SEQ ID NO: 1 or a functional fragment thereof, an orthologue or a paralogue thereof, or a splice variant thereof;
(ii) an exogenous nucleic acid encoding a protein having at least 60%, preferably at least 70% sequence identity, at least 80%, at least 90%, at least 95%, at least 98%, at least 99% sequence identity, or even 100% sequence identity with SEQ ID NO: 2, a functional fragment thereof, an orthologue or a paralogue thereof; preferably the encoded protein confers enhanced fungal resistance relative to control plants;
(iii) an exogenous nucleic acid capable of hybridizing under stringent conditions with a complementary sequence of any of the nucleic acids according to (i) or (ii); preferably encoding a RLK1 protein; preferably wherein the nucleic acid molecule codes for a polypeptide which has essentially identical properties to the polypeptide described in SEQ ID NO: 10 or 2; preferably the encoded protein confers enhanced fungal resistance relative to control plants; and/or by
(iv) an exogenous nucleic acid encoding the same RLK1 protein as any of the nucleic acids of (i) to (iii) above, but differing from the nucleic acids of (i) to (iii) above due to the degeneracy of the genetic code
is a further embodiment of the invention.

A method for increasing fungal resistance, preferably resistance to Phakopsoraceae, for example soy bean rust, in a plant, plant part, or plant cell, by increasing the expression of a RLK1 protein or a functional fragment, orthologue, paralogue or homologue thereof, or a splice variant thereof, wherein the RLK1 protein is encoded by
(i) an exogenous nucleic acid having at least 60% identity, preferably at least 70% sequence identity, at least 80%, at least 90%, at least 95%, at least 98%, at least 99% sequence identity, or even 100% sequence identity with SEQ ID NO: 9 or a functional fragment thereof, an orthologue or a paralogue thereof, or a splice variant thereof;
(ii) an exogenous nucleic acid encoding a protein having at least 60%, preferably at least 70% sequence identity, at least 80%, at least 90%, at least 95%, at least 98%, at least 99% sequence identity, or even 100% sequence identity with SEQ ID NO: 10, a functional fragment thereof, an orthologue or a paralogue thereof; preferably the encoded protein confers enhanced fungal resistance relative to control plants;
(iii) an exogenous nucleic acid capable of hybridizing under stringent conditions with a complementary sequence of any of the nucleic acids according to (i) or (ii); preferably encoding a RLK1 protein; preferably wherein the nucleic acid molecule codes for a polypeptide which has essentially identical properties to the polypeptide described in SEQ ID NO: 10 or 2; preferably the encoded protein confers enhanced fungal resistance relative to control plants; and/or by
(iv) an exogenous nucleic acid encoding the same RLK1 protein as any of the nucleic acids of (i) to (iii) above, but differing from the nucleic acids of (i) to (iii) above due to the degeneracy of the genetic code
is a further embodiment of the invention.

In a further method of the invention, the method comprises the steps of
(a) stably transforming a plant cell with a recombinant expression cassette comprising
(i) a nucleic acid having at least 60% identity, preferably at least 70% sequence identity, at least 80%, at least 90%, at least 95%, at least 98%, at least 99% sequence identity, or even 100% sequence identity with SEQ ID NO: 9, 1, 3, 8, 11-18, 19, 21, 23, 25, 27, 29, 31, or 33, or a functional fragment thereof, or an orthologue or a paralogue thereof, or a splice variant thereof;
(ii) a nucleic acid coding for a protein having at least 60% Identity, preferably at least 70% sequence identity, at least 80%, at least 90%, at least 95%, at least 98%, at least 99% sequence identity, or even 100% sequence identity with SEQ ID NO: 10, 2, 20, 22, 24, 26, 28, 30, 32, or 34, a functional fragment thereof, an orthologue or a paralogue thereof; preferably the encoded protein confers enhanced fungal resistance relative to control plants;
(iii) a nucleic acid capable of hybridizing under stringent conditions with a complementary sequence of any of the nucleic acids according to (i) or (ii); preferably encoding a RLK1 protein; preferably wherein the nucleic acid molecule codes for a polypeptide which has essentially identical properties to the polypeptide described in SEQ ID NO: 10 or 2; preferably the encoded protein confers enhanced fungal resistance relative to control plants; and/or
(iv) a nucleic acid encoding the same RLK1 polypeptide as any of the nucleic acids of (i) to (iii) above, but differing from the nucleic acids of (i) to (iii) above due to the degeneracy of the genetic code, in functional linkage with a promoter;
(b) regenerating the plant from the plant cell; and
(c) expressing said nucleic acid, optionally wherein the nucleic acid which codes for an RLK1 protein is expressed in an amount and for a period sufficient to generate or to increase soybean rust resistance in said plant.

Preferably, the method comprises the steps of
(a) stably transforming a plant cell with a recombinant expression cassette comprising
(i) a nucleic acid having at least 60% identity, preferably at least 70% sequence identity, at least 80%, at least 90%, at least 95%, at least 98%, at least 99% sequence identity, or even 100% sequence identity with SEQ ID NO: 1, or a functional fragment thereof, or an orthologue or a paralogue thereof, or a splice variant thereof;
(ii) a nucleic acid coding for a protein having at least 60% identity, preferably at least 70% sequence identity, at least 80%, at least 90%, at least 95%, at least 98%, at least 99% sequence identity, or even 100% sequence identity with SEQ ID NO: 2, a functional fragment thereof, an orthologue or a paralogue thereof; preferably the encoded protein confers enhanced fungal resistance relative to control plants;
(iii) a nucleic acid capable of hybridizing under stringent conditions with a complementary sequence of any of the nucleic acids according to (i) or (ii); preferably encoding a RLK1 protein; preferably wherein the nucleic acid molecule codes for a polypeptide which has essentially identical properties to the polypeptide described in SEQ ID NO: 10 or 2; preferably the encoded protein confers enhanced fungal resistance relative to control plants; and/or (iv) a nucleic acid encoding the same RLK1 polypeptide as any of the nucleic acids of (i) to (iii) above, but differing from the nucleic acids of (i) to (iii) above due to the degeneracy of the genetic code, in functional linkage with a promoter;

(b) regenerating the plant from the plant cell; and (c) expressing said nucleic acid, optionally wherein the nucleic acid which codes for a RLK1 protein is expressed in an amount and for a period sufficient to generate or to Increase soybean rust resistance in said plant.

Preferably, the method comprises the steps of (a) stably transforming a plant cell with a recombinant expression cassette comprising (i) a nucleic acid having at least 60% identity, preferably at least 70% sequence identity, at least 80%, at least 90%, at least 95%, at least 98%, at least 99% sequence identity, or even 100% sequence identity with SEQ ID NO: 9, or a functional fragment thereof, or an orthologue or a paralogue thereof, or a splice variant thereof;

(ii) a nucleic acid coding for a protein having at least 60% identity, preferably at least 70% sequence identity, at least 80%, at least 90%, at least 95%, at least 98%, at least 99% sequence identity, or even 100% sequence identity with SEQ ID NO: 10, a functional fragment thereof, an orthologue or a paralogue thereof; preferably the encoded protein confers enhanced fungal resistance relative to control plants;

(iii) a nucleic acid capable of hybridizing under stringent conditions with a complementary sequence of any of the nucleic acids according to (i) or (ii); preferably encoding a RLK1 protein; preferably wherein the nucleic acid molecule codes for a polypeptide which has essentially identical properties to the polypeptide described in SEQ ID NO: 10 or 2; preferably the encoded protein confers enhanced fungal resistance relative to control plants; and/or (iv) a nucleic acid encoding the same RLK1 polypeptide as any of the nucleic acids of (i) to (iii) above, but differing from the nucleic acids of (i) to (iii) above due to the degeneracy of the genetic code, in functional linkage with a promoter;

(b) regenerating the plant from the plant cell; and (c) expressing said nucleic acid, optionally wherein the nucleic acid which codes for a RLK1 protein is expressed in an amount and for a period sufficient to generate or to increase soybean rust resistance in said plant Preferably, the method for increasing fungal resistance, preferably resistance to Phakopsoraceae, for example soy bean rust, in a plant, plant part, or plant cell further comprises the step of selecting a transgenic plant expressing (i) an exogenous nucleic acid having at least 60% identity, preferably at least 70% sequence identity, at least 80%, at least 90%, at least 95%, at least 98%, at least 99% sequence identity, or even 100% sequence identity with SEQ ID NO: 9, 1, 3, 8, 11-18, 19, 21, 23, 25, 27, 29, 31, or 33, or a functional fragment thereof, or an orthologue or a paralogue thereof, or a splice variant thereof;

(ii) an exogenous nucleic acid coding for a protein having at least 60% identity, preferably at least 70% sequence identity, at least 80%, at least 90%, at least 95%, at least 98%, at least 99% sequence identity, or even 100% sequence identity with SEQ ID NO: 10, 2, 20, 22, 24, 26, 28, 30, 32, or 34, a functional fragment thereof, an orthologue or a paralogue thereof; preferably the encoded protein confers enhanced fungal resistance relative to control plants;

(iii) an exogenous nucleic acid capable of hybridizing under stringent conditions with a complementary sequence of any of the nucleic acids according to (i) or (ii); preferably encoding a RLK1 protein; preferably wherein the nucleic acid molecule codes for a polypeptide which has essentially identical properties to the polypeptide described in SEQ ID NO: 10 or 2; preferably the encoded protein confers enhanced fungal resistance relative to control plants; and/or (iv) an exogenous nucleic acid encoding the same RLK1 polypeptide as any of the nucleic acids of (i) to (iii) above, but differing from the nucleic acids of (i) to (iii) above due to the degeneracy of the genetic code.

A preferred embodiment is a method for increasing resistance to soy bean rust in a soy bean plant, soy bean plant part, or soy bean plant cell, by increasing the expression of an RLK1 protein, wherein the RLK1 protein is encoded by (i) an exogenous nucleic acid having at least 80%, at least 90%, at least 95%, at least 98%, at least 99% sequence identity, or even 100% sequence identity with SEQ ID NO: 9, 1, 3, 8, 11-18, 19, 21, 23, 25, 27, 29, 31, or 33;

(ii) an exogenous nucleic acid encoding a protein having at least 80%, at least 90%, at least 95%, at least 98%, at least 99% sequence identity, or even 100% sequence identity with SEQ ID NO: 10, 2, 20, 22, 24, 26, 28, 30, 32, or 34; preferably the encoded protein confers enhanced fungal resistance relative to control plants;

(iii) an exogenous nucleic acid capable of hybridizing under stringent conditions with a complementary sequence of any of the nucleic acids according to (i) or (ii); preferably encoding a RLK1 protein; preferably wherein the nucleic acid molecule codes for a polypeptide which has essentially identical properties to the polypeptide described in SEQ ID NO: 10 or 2; preferably the encoded protein confers enhanced fungal resistance relative to control plants; and/or by (iv) an exogenous nucleic acid encoding the same RLK1 protein as any of the nucleic acids of (i) to (iii) above, but differing from the nucleic acids of (i) to (iii) above due to the degeneracy of the genetic code, wherein increasing the expression of the RLK1 protein is achieved by transforming the soy bean plant, plant part or plant cell with a nucleic acid comprising the nucleic acid set out under item (i) or (ii) or (iii) or (iv).

Also a preferred embodiment is a method for increasing resistance to soy bean rust in a soy bean plant, soy bean plant part, or soy bean plant cell, by increasing the expression of an RLK1 protein, wherein the RLK1 protein is encoded by (i) an exogenous nucleic acid having at least 80%, at least 90%, at least 95%, at least 98%, at least 99% sequence identity, or even 100% sequence identity with SEQ ID NO: 9, 1, 3, 8, 11-18, 19, 21, 23, 25, 27, 29, 31, or 33;

(ii) an exogenous nucleic acid encoding a protein having at least 80%, at least 90%, at least 95%, at least 98%, at least 99% sequence identity, or even 100% sequence Identity with SEQ ID NO: 10, 2, 20, 22, 24, 26, 28, 30, 32, or 34; preferably the encoded protein confers enhanced fungal resistance relative to control plants; or (iii) an exogenous nucleic acid encoding the same RLK1 protein as any of the nucleic acids of (i) to (ii) above, but differing from the nucleic acids of (i) to (ii) above due to the degeneracy of the genetic code, wherein increasing the expression of the RLK1 protein is achieved by transforming the soy bean plant, plant part or plant cell with a nucleic acid comprising the nucleic acid set out under item (i) or (ii) or (iii).

The fungal pathogens or fungus-like pathogens (such as, for example, Chromista) can belong to the group comprising Plasmodiophoramycota, Oomycota, Ascomycota, Chytridiomycetes, Zygomycetes, Basidiomycota or Deuteromycetes (*Fungi imperfecti*). Pathogens which may be mentioned by way of example, but not by limitation, are those detailed in Tables 2 and 3, and the diseases which are associated with them.

TABLE 2

Diseases caused by biotrophic and/or heminecrotrophic phytopathogenic fungi

| Disease | Pathogen |
| --- | --- |
| Leaf rust | *Puccinia recondita* |
| Yellow rust | *P. striiformis* |

TABLE 2-continued

Diseases caused by biotrophic and/or heminecrotrophic phytopathogenic fungi

| Disease | Pathogen |
| --- | --- |
| Powdery mildew | *Erysiphe graminis*/*Blumeria graminis* |
| Rust (common corn) | *Puccinia sorghi* |
| Rust (Southern corn) | *Puccinia polysora* |
| Tobacco leaf spot | *Cercospora nicotianae* |
| Rust (soybean) | *Phakopsora pachyrhizi*, *P. meibomiae* |
| Rust (tropical corn) | *Physopella pallescens*, *P. zeae* = *Angiopsora zeae* |

TABLE 3

Diseases caused by necrotrophic and/or hemibiotrophic fungi and Oomycetes

| Disease | Pathogen |
| --- | --- |
| Plume blotch | *Septoria* (*Stagonospora*) *nodorum* |
| Leaf blotch | *Septoria tritici* |
| Ear fusarioses | *Fusarium* spp. |
| Late blight | *Phytophthora infestans* |
| Anthrocnose leaf blight | *Colletotrichum graminicola* (teleomorph: |
| Anthracnose stalk rot | *Glomerella graminicola* Politis); *Glomerella tucumanensis* (anamorph: *Glomerella falcatum* Went) |
| *Curvularia* leaf spot | *Curvularia clavata*, *C. eragrostidis*, = *C. maculans* (teleomorph: *Cochliobolus eragrostidis*), *Curvularia inaequalis*, *C. intermedia* (teleomorph: *Cochliobolus intermedius*), *Curvularia lunata* (teleomorph: *Cochliobolus lunatus*), *Curvularia pallescens* (teleomorph: *Cochliobolus pallescens*) *Curvularia senegalensis*, *C. tuberculata* (teleomorph: *Cochliobolus tuberculatus*) |
| *Didymella* leaf spot | *Didymella exitalis* |
| *Diplodia* leaf spot or streak | *Stenocarpella macrospora* = *Diplodialeaf macrospora* |
| Brown stripe downy mildew | *Sclerophthora rayssiae* var. *zeae* |
| Crazy top downy mildew | *Sclerophthora macrospora* = *Sclerospora macrospora* |
| Green ear downy mildew (*graminicola* downy mildew) | *Sclerospora graminicola* |
| Leaf spots, minor | *Alternaria alternata*, *Ascochyta maydis*, *A. tritici*, *A. zeicola*, *Bipolaris victoriae* = *Helminthosporium victoriae* (teleomorph: *Cochliobolus victoriae*), *C. sativus* (anamorph: *Bipolaris sorokiniana* = *H. sorokinianum* = *H. sativum*), *Epicoccum nigrum*, *Exserohilum prolatum* = *Drechslera prolata* (teleomorph: *Setosphaeria prolata*) *Graphium penicillioides*, *Leptosphaeria maydis*, *Leptothyrium zeae*, *Ophiosphaerella herpotricha*, (anamorph: *Scolecosporiella* sp.), *Paraphaeosphaeria michotii*, *Phoma* sp., *Septoria zeae*, *S. zeicola*, *S. zeina* |
| Northern corn leaf blight (white blast, crown stalk rot, stripe) | *Setosphaeria turcica* (anamorph: *Exserohilum turcicum* = *Helminthosporium turcicum*) |
| Northern corn leaf spot *Helminthosporium* ear rot (race 1) | *Cochliobolus carbonum* (anamorph: *Bipolaris zeicola* = *Helminthosporium carbonum*) |
| *Phaeosphaeria* leaf spot | *Phaeosphaeria maydis* = *Sphaerulina maydis* |
| *Rostratum* leaf spot (*Helminthosporium* leaf disease, ear and stalk rot) | *Setosphaeria rostrata*, (anamorph: *xserohilum rostratum* = *Helminthosporium rostratum*) |
| Java downy mildew | *Peronosclerospora maydis* = *Sclerospora maydis* |
| Philippine downy mildew | *Peronosclerospora philippinensis* = *Sclerospora philippinensis* |
| *Sorghum* downy mildew | *Peronosclerospora sorghi* = *Sclerospora sorghi* |

TABLE 3-continued

Diseases caused by necrotrophic and/or hemibiotrophic fungi and Oomycetes

| Disease | Pathogen |
| --- | --- |
| *Spontaneum* downy mildew | *Peronosclerospora spontanea = Sclerospora spontanea* |
| Sugarcane downy mildew | *Peronosclerospora sacchari = Sclerospora sacchari* |
| *Sclerotium* ear rot (southern blight) | *Sclerotium rolfsii* Sacc. (teleomorph: *Athelia rolfsii*) |
| Seed rot-seedling blight | *Bipolaris sorokiniana, B. zeicola = Helminthosporium carbonum, Diplodia maydis, Exserohilum pedicillatum, Exserohilum turcicum = Helminthosporium turcicum, Fusarium avenaceum, F. culmorum, F. moniliforme, Gibberella zeae* (anamorph: *F. graminearum*), *Macrophomina phaseolina, Penicillium,* spp. *Phomopsis* sp., *Pythium* spp., *Rhizoctonia solani, R. zeae, Sclerotium rolfsii, Spicaria* sp. |
| *Selenophoma* leaf spot | *Selenophoma* sp. |
| Yellow leaf blight | *Ascochyta ischaemi, Phyllosticta maydis* (teleomorph: *Mycosphaerella zeae-maydis*) |
| Zonate leaf spot | *Gloeocercospora sorghi* |

The following are especially preferred:

Plasmodiophoromycota such as *Plasmodiophora brassicae* (clubroot of crucifers), *Spongospora subterranea, Polymyxa graminis,*

Oomycota such as *Bremia lactucae* (downy mildew of lettuce), *Peronospora* (downy mildew) in snapdragon (*P. antirrhini*), onion (*P. destructor*), spinach (*P. effusa*), soybean (*P. manchurica*), tobacco ("blue mold"; *P. tabacina*) alfalfa and clover (*P. trifolium*), *Pseudoperonospora humuli* (downy mildew of hops), *Plasmopara* (downy mildew in grapevines) (*P. viticola*) and sunflower (*P. halstedii*), *Sclerophthora macrospora* (downy mildew in cereals and grasses), *Pythium* (for example damping-off of Beta beet caused by *P. debaryanum*), *Phytophthora infestans* (late blight in potato and in tomato and the like), *Albugo* spec.

Ascomycota such as *Microdochium nivale* (snow mold of rye and wheat), *Fusarium, Fusarium graminearum, Fusarium culmorum* (partial ear sterility mainly in wheat), *Fusarium oxysporum* (*Fusarium* wilt of tomato), *Blumeria graminis* (powdery mildew of barley (f.sp. *hordei*) and wheat (f.sp. *tritici*)), *Erysiphe pisi* (powdery mildew of pea), *Nectria galligena* (*Nectria* canker of fruit trees), *Uncinula necator* (powdery mildew of grapevine), *Pseudopeziza tracheiphila* (red fire disease of grapevine), *Claviceps purpurea* (ergot on, for example, rye and grasses), *Gaeumannomyces graminis* (take-all on wheat, rye and other grasses), *Magnaporthe grisea, Pyrenophora graminea* (leaf stripe of barley), *Pyrenophora teres* (net blotch of barley), *Pyrenophora tritici*-repentis (leaf blight of wheat), *Venturia inaequalis* (apple scab), *Sclerotinia sclerotium* (stalk break, stem rot), *Pseudopeziza medicaginis* (leaf spot of alfalfa, white and red clover).

Basidiomycetes such as *Typhula incamata* (*typhula* blight on barley, rye, wheat), *Ustilago maydis* (blister smut on maize), *Ustilago nuda* (loose smut on barley), *Ustilago tritici* (loose smut on wheat, spelt), *Ustilago avenae* (loose smut on oats), *Rhizoctonia solani* (rhizoctonia root rot of potato), *Sphacelotheca* spp. (head smut of sorghum), *Melampsora lini* (rust of flax), *Puccinia graminis* (stem rust of wheat, barley, rye, oats), *Puccinia recondita* (leaf rust on wheat), *Puccinia dispersa* (brown rust on rye), *Puccinia hordei* (leaf rust of barley), *Puccinia coronata* (crown rust of oats), *Puccinia striiformis* (yellow rust of wheat, barley, rye and a large number of grasses), *Uromyces appendiculatus* (brown rust of bean), *Sclerotium rolfsii* (root and stem rots of many plants).

Deuteromycetes (*Fungi imperfecti*) such as *Septoria* (*Stagonospora*) *nodorum* (glume blotch) of wheat (*Septoria tritici*), *Pseudocercosporella herpotrichoides* (eyespot of wheat, barley, rye), *Rynchosporium secalis* (leaf spot on rye and barley), *Alternaria solani* (early blight of potato, tomato), *Phoma betae* (blackleg on Beta beet), *Cercospora beticola* (leaf spot on Beta beet), *Alternaria brassicae* (black spot on oilseed rape, cabbage and other crucifers), *Verticillium dahliae* (verticillium wilt), *Colletotrichum, Colletotrichum lindemuthianum* (bean anthracnose), *Phoma lingam* (blackleg of cabbage and oilseed rape), *Botrytis cinerea* (grey mold of grapevine, strawberry, tomato, hops and the like).

Especially preferred are biotrophic pathogens, e.g., *Phakopsora pachyrhizi* and/or those pathogens which have essentially a similar infection mechanism as *Phakopsora pachyrhizi*, as described herein. Particularly preferred are pathogens from the subclass Pucciniomycetes, preferably from the order Pucciniales, preferably the group Uredinales (rusts), among which in particular the Melompsoraceae. Preferred are Phakopsoraceae, more preferably *Phakopsora*. Especially preferred are *Phakopsora pachyrhizi* and/or *Phakopsora meibomiae*.

Also preferred rust *fungi* are selected from the group of *Puccinia, Gymnosporangium, Juniperus, Cronartium, Hemileia,* and *Uromyces*; preferably *Puccinia sorghi, Gymnosporangium juniperi-virginianae, Juniperus virginiana, Cronartium ribicola, Hemileia vastatrix, Puccinia graminis, Puccinia coronata, Uromyces phaseoli, Puccinia hemerocallidis, Puccinia persistens* subsp. *Triticina, Puccinia striiformis, Puccinia graminis* causes, and/or *Uromyces appendeculatus.*

RLK1 Expression Constructs and Vector Constructs

A recombinant vector construct comprising:
(a) (i) a nucleic acid having at least 60% identity, preferably at least 70% sequence Identity, at least 80%, at least 90%, at least 95%, at least 98%, at least 99% sequence identity, or even 100% sequence identity with SEQ ID NO: 9, 1, 3, 8, 11-18, 19, 21, 23, 25, 27, 29, 31, or 33, or a functional fragment thereof, or an orthologue or a paralogue thereof, or a splice variant thereof;

(ii) a nucleic acid coding for a protein having at least 60% identity, preferably at least 70% sequence identity, at least 80%, at least 90%, at least 95%, at least 98%, at least 99% sequence identity, or even 100% sequence identity with SEQ ID NO: 10, 2, 20, 22, 24, 26, 28, 30, 32, or 34, a functional fragment thereof, an orthologue or a paralogue thereof; preferably the encoded protein confers enhanced fungal resistance relative to control plants;

(iii) a nucleic acid capable of hybridizing under stringent conditions with a complementary sequence of any of the nucleic acids according to (i) or (ii); preferably encoding a RLK1 protein; preferably wherein the nucleic acid molecule codes for a polypeptide which has essentially identical properties to the polypeptide described in SEQ ID NO: 10 or 2; preferably the encoded protein confers enhanced fungal resistance relative to control plants; and/or (iv) a nucleic acid encoding the same RLK1 protein as any of the nucleic acids of (i) to (iii) above, but differing from the nucleic acids of (i) to (iii) above due to the degeneracy of the genetic code, operably linked with (b) a promoter and (c) a transcription termination sequence is a further embodiment of the invention.

Furthermore, a recombinant vector construct is provided comprising:

(a) (i) a nucleic acid having at least 80%, at least 90%, at least 95%, at least 98%, at least 99% sequence identity, or even 100% sequence identity with SEQ ID NO: 9, 1, 3, 8, 11-18, 19, 21, 23, 25, 27, 29, 31, or 33;

(ii) a nucleic acid coding for a protein having at least 80%, at least 90%, at least 95%, at least 98%, at least 99% sequence identity, or even 100% sequence identity with SEQ ID NO: 10, 2, 20, 22, 24, 26, 28, 30, 32, or 34; preferably the encoded protein confers enhanced fungal resistance relative to control plants;

(iii) a nucleic acid capable of hybridizing under stringent conditions with a complementary sequence of any of the nucleic acids according to (i) or (ii); preferably encoding a RLK1 protein; preferably wherein the nucleic acid molecule codes for a polypeptide which has essentially identical properties to the polypeptide described in SEQ ID NO: 10 or 2; preferably the encoded protein confers enhanced fungal resistance relative to control plants; and/or (iv) a nucleic acid encoding the same RLK1 protein as any of the nucleic acids of (i) to (iii) above, but differing from the nucleic acids of (i) to (iii) above due to the degeneracy of the genetic code, operably linked with (b) a promoter and (c) a transcription termination sequence is a further embodiment of the invention.

Furthermore, a recombinant vector construct is provided comprising:

(a) (i) a nucleic acid having at least 80%, at least 90%, at least 95%, at least 98%, at least 99% sequence identity, or even 100% sequence identity with SEQ ID NO: 1;

(ii) a nucleic acid coding for a protein having at least 80%, at least 90%, at least 95%, at least 98%, at least 99% sequence identity, or even 100% sequence identity with SEQ ID NO: 2; preferably the encoded protein confers enhanced fungal resistance relative to control plants;

(iii) a nucleic acid capable of hybridizing under stringent conditions with a complementary sequence of any of the nucleic acids according to (i) or (ii); preferably encoding a RLK1 protein; preferably wherein the nucleic acid molecule codes for a polypeptide which has essentially identical properties to the polypeptide described in SEQ ID NO: 10 or 2; preferably the encoded protein confers enhanced fungal resistance relative to control plants; and/or (iv) a nucleic acid encoding the same RLK1 protein as any of the nucleic acids of (i) to (iii) above, but differing from the nucleic acids of (i) to (iii) above due to the degeneracy of the genetic code, operably linked with (b) a promoter and (c) a transcription termination sequence is a further embodiment of the invention.

Furthermore, a recombinant vector construct is provided comprising:

(a) (i) a nucleic acid having at least 80%, at least 90%, at least 95%, at least 98%, at least 99% sequence identity, or even 100% sequence identity with SEQ ID NO: 9;

(ii) a nucleic acid coding for a protein having at least 80%, at least 90%, at least 95%, at least 98%, at least 99% sequence identity, or even 100% sequence identity with SEQ ID NO: 10; preferably the encoded protein confers enhanced fungal resistance relative to control plants;

(iii) a nucleic acid capable of hybridizing under stringent conditions with a complementary sequence of any of the nucleic acids according to (i) or (ii); preferably encoding a RLK1 protein; preferably wherein the nucleic acid molecule codes for a polypeptide which has essentially identical properties to the polypeptide described in SEQ ID NO: 10 or 2; preferably the encoded protein confers enhanced fungal resistance relative to control plants; and/or (iv) a nucleic acid encoding the same RLK1 protein as any of the nucleic acids of (i) to (iii) above, but differing from the nucleic acids of (i) to (iii) above due to the degeneracy of the genetic code, operably linked with (b) a promoter and (c) a transcription termination sequence is a further embodiment of the invention.

Promoters according to the present invention may be constitutive, inducible, in particular pathogen-inducible, developmental stage-preferred, cell type-preferred, tissue-preferred or organ-preferred. Constitutive promoters are active under most conditions. Non-limiting examples of constitutive promoters include the CaMV 19S and 35S promoters (Odell et al., 1985, Nature 313:810-812), the sX CaMV 35S promoter (Kay et al., 1987, Science 236:1299-1302), the Sep1 promoter, the rice actin promoter (McElroy et al., 1990, Plant Cell 2:163-171), the *Arabidopsis* actin promoter, the ubiquitin promoter (Christensen et al., 1989, Plant Molec. Biol. 18:675-689); pEmu (Last et al., 1991, Theor. Appl. Genet. 81:581-588), the figwort mosaic virus 35S promoter, the Smas promoter (Velten et al., 1984, EMBO J. 3:2723-2730), the GRP1-8 promoter, the cinnamyl alcohol dehydrogenase promoter (U.S. Pat. No. 5,683,439), promoters from the T-DNA of *Agrobacterium*, such as mannopine synthase, nopaline synthase, and octopine synthase, the small subunit of ribulose biphosphate carboxylase (ssuRUBISCO) promoter, and/or the like.

Preferably, the expression vector of the invention comprises a constitutive promoter, mesophyll-specific promoter, epidermis-specific promoter, root-specific promoter, a pathogen inducible promoter, or a fungal-inducible promoter.

A promoter is inducible, if its activity, measured on the amount of RNA produced under control of the promoter, is at least 30%, at least 40%, at least 50% preferably at least 60%, at least 70%, at least 80%, at least 90% more preferred at least 100%, at least 200%, at least 300% higher in its induced state, than in its un-induced state. A promoter is cell-, tissue- or organ-specific, if its activity, measured on the amount of RNA produced under control of the promoter, is at least 30%, at least 40%, at least 50% preferably at least 60%, at least 70%, at least 80%, at least 90% more preferred at least 100%, at least 200%, at least 300% higher in a particular cell-type, tissue or organ, then in other cell-types or tissues of the same plant, preferably the other cell-types or tissues are cell types or tissues of the same plant organ, e.g. a root. In the case of organ specific promoters, the promoter activity has to be compared to the promoter activity in other plant organs, e.g. leaves, stems, flowers or seeds. Preferably, the promoter is a constitutive promoter, mesophyll-specific promoter, or epidermis-specific promoter.

Especially preferred is a promoter from parsley, preferably, the parsley ubiquitine promoter. A preferred terminator is the terminator of the cathepsin D inhibitor gene from *Solanum* tuberosum.

In preferred embodiments, the increase in the protein amount and/or activity of the RLK1 protein takes place in a constitutive or tissue-specific manner. In especially preferred embodiments, an essentially pathogen-induced increase in the protein amount and/or protein activity takes place, for example by recombinant expression of the RLK1 nucleic acid under the control of a fungal-inducable promoter. In particular, the expression of the RLK1 nucleic acid takes place on fungal infected sites, where, however, preferably the expression of the RLK1 nucleic acid remains essentially unchanged in tissues not infected by fungus.

Developmental stage-preferred promoters are preferentially expressed at certain stages of development. Tissue and organ preferred promoters include those that are preferentially expressed in certain tissues or organs, such as leaves, roots, seeds, or xylem. Examples of tissue preferred and organ preferred promoters include, but are not limited to fruit-preferred, ovule-preferred, male tissue-preferred, seed-preferred, integument-preferred, tuber-preferred, stalk-preferred, pericarp-preferred, leaf-preferred, stigma-preferred, pollen-preferred, anther-preferred, a petal-preferred, sepal-preferred, pedicel-preferred, silique-preferred, stem-preferred, root-preferred promoters and/or the like. Seed preferred promoters are preferentially expressed during seed development and/or germination. For example, seed preferred promoters can be embryo-preferred, endosperm preferred and seed coat-preferred. See Thompson et al., 1989, BioEssays 10:108. Examples of seed preferred promoters include, but are not limited to cellulose synthase (celA), Cim1, gamma-zein, globulin-1, maize 19 kD zein (cZ19B1) and/or the like.

Other suitable tissue-preferred or organ-preferred promoters include, but are not limited to, the napin-gene promoter from rapeseed (U.S. Pat. No. 5,608,152), the USP-promoter from *Vicia faba* (Baeumlein et al., 1991, Mol Gen Genet. 225(3):459-67), the oleosinpromoter from *Arabidopsis* (PCT Application No. WO 98/45461), the phaseolin-promoter from *Phaseolus vulgaris* (U.S. Pat. No. 5,504,200), the Bce4-promoter from *Brassica* (PCT Application No. WO 91/13980), or the legumin B4 promoter (LeB4; Baeumlein et al., 1992, Plant Journal, 2(2):233-9), as well as promoters conferring seed specific expression in monocot plants like maize, barley, wheat, rye, rice, etc. Suitable promoters to note are the Ipt2 or Ipt1-gene promoter from barley (PCT Application No. WO 95/15389 and PCT Application No. WO 95/23230) or those described in PCT Application No. WO 99/16890 (promoters from the barley hordein-gene, rice glutelin gene, rice oryzin gene, rice prolamin gene, wheat gliadin gene, wheat glutelin gene, oat glutelin gene, Sorghum kasirin-gene, and/or rye secalin gene).

Promoters useful according to the invention include, but are not limited to, are the major chlorophyll a/b binding protein promoter, histone promoters, the Ap3 promoter, the β-conglycin promoter, the napin promoter, the soybean lectin promoter, the maize 15 kD zein promoter, the 22 kD zein promoter, the 27 kD zein promoter, the g-zein promoter, the waxy, shrunken 1, shrunken 2, bronze promoters, the Zm13 promoter (U.S. Pat. No. 5,086,169), the maize polygalacturonase promoters (PG) (U.S. Pat. Nos. 5,412,085 and 5,545,546), the SGB6 promoter (U.S. Pat. No. 5,470,359), as well as synthetic or other natural promoters.

Epidermis-specific promoters may be selected from the group consisting of:

WIR5 (=GstA1); acc. X56012; Dudler & Schweizer,
GLP4, acc. AJ310534; Wel Y., Zhang Z., Andersen C. H., Schmelzer E., Gregersen P. L.,
Collinge D. B., Smedegaard-Petersen V. and Thordal-Christensen H., Plant Molecular Biology 36, 101 (1998),
GLP2a, acc. AJ237942, Schweizer P., Christoffel A. and Dudler R., Plant J. 20, 541 (1999);
Prx7, acc. AJ003141, Kristensen B. K., Ammitzböll H., Rasmussen S. K. and Nielsen K. A., Molecular Plant Pathology, 2(6), 311 (2001);
GerA, acc. AF250933; Wu S., Druka A., Horvath H., Kleinhofs A., Kannangara G. and von Wettstein D., Plant Phys Biochem 38, 685 (2000);
OsROC1, acc. AP004656
RTBV, acc. AAV62708, AAV62707; Klöti A., Henrich C., Bieri S., He X., Chen G., Burkhardt P. K., Wünn J., Lucca P., Hohn T., Potrykus I. and Fütterer J., PMB 40, 249 (1999);
Chitinase ChtC2-Promoter from potato (Ancillo et al., Planta. 217(4), 566, (2003)); AtProT3 Promoter (Grallath et al., Plant Physiology. 137(1), 117 (2005)); SHN-Promoters from *Arabidopsis* (AP2/EREBP transcription factors involved in cutin and wax production) (Aarón et al., Plant Cell. 16(9), 2463 (2004)); and/or GSTA1 from wheat (Dudler et al., WP2005306368 and Altpeter et al., Plant Molecular Biology. 57(2), 271 (2005)).

Mesophyll-specific promoters may be selected from the group consisting of:
PPCZm1 (=PEPC); Kausch A. P., Owen T. P., Zachwieja S. J., Flynn A. R. and Sheen J., Plant Mol. Biol. 45, 1 (2001);
OsrbcS, Kyozuka et al., PlaNT Phys 102, 991 (1993); Kyozuka J., McElroy D., Hayakawa T., Xie Y., Wu R. and Shimamoto K., Plant Phys. 102, 991 (1993); OsPPDK, acc. AC099041;
TaGF-2.8, acc. M63223; Schweizer P., Christoffel A. and Dudler R., Plant J. 20, 541 (1999);
TaFBPase, acc. X53957;
TaWIS1, acc. AF467542; US 200220115849;
HvBIS1, acc. AF467539; US 200220115849;
ZmMIS1, acc. AF467514; US 200220115849;
HvPR1a, acc. X74939; Bryngelsson et al., Mol. Plant Microbe Interacti. 7 (2), 267 (1994);
HvPR1b, acc. X74940; Bryngelsson et al., Mol. Plant Microbe Interact. 7(2), 267 (1994);
HvB1,3gluc; acc. AF479647;
HvPrx8, acc. AJ276227; Kristensen et al., Molecular Plant Pathology, 2(6), 311 (2001); and/or HvPAL, acc. X97313; Wel Y., Zhang Z., Andersen C. H., Schmelzer E., Gregersen P. L., Collinge D. B., Smedegaard-Petersen V. and Thordal-Christensen H. Plant Molecular Biology 36, 101 (1998).

Constitutive promoters may be selected from the group consisting of

PcUbi promoter from parsley (WO 03/102198)

CaMV 35S promoter: Cauliflower Mosaic Virus 35S promoter (Benfey et al. 1989 EMBO J. 8(8): 2195-2202), STPT promoter: *Arabidopsis thaliana* Short Triose phosphate translocator promoter (Accession NM_123979)

Act1 promoter: *Oryza sativa* actin 1 gene promoter (McElroy et al. 1990 PLANT CELL 2(2) 163-171 a) and/or EF1A2 promoter: *Glycine max* translation elongation factor EF1 alpha (US 20090133159).

One type of vector construct is a "plasmid," which refers to a circular double stranded DNA loop into which additional DNA segments can be ligated. Another type of vector is a viral vector, wherein additional DNA segments can be ligated into the viral genome. Certain vector constructs are capable of autonomous replication in a host plant cell into which they are introduced. Other vector constructs are integrated into the genome of a host plant cell upon introduction into the host cell, and thereby are replicated along with the host genome. In particular the vector construct is capable of directing the expression of gene to which the vectors is operatively linked. However, the invention is intended to include such other forms of expression vector constructs, such as viral vectors (e.g., potato virus X, tobacco rattle virus, and/or Gemini virus), which serve equivalent functions.

In preferred embodiments, the increase in the protein quantity or function of the RLK1 protein takes place in a constitutive or tissue-specific manner. In especially preferred embodiments, an essentially pathogen-induced increase in the protein quantity or protein function takes place, for example by exogenous expression of the RLK1 nucleic acid under the control of a fungal-inducible promoter. In particular, the expression of the RLK1 nucleic acid takes place on fungal infected sites, where, however, preferably the expression of the RLK1 nucleic acid sequence remains essentially unchanged in tissues not infected by fungus. In preferred embodiments, the protein amount of an RLK1 protein in the plant is increased by at least 10%, at least 20%, at least 30%, at least 40%, at least 50%, at least 60%, at least 70%, at least 80%, at least 90%, or at least 95% or more in comparison to a wild type plant that is not transformed with the RLK1 nucleic acid.

A preferred embodiment is the use of an expression construct or a vector as described herein for the transformation of a plant, plant part, or plant cell to provide a pathogen resistant plant, plant part, or plant cell. Thus, a preferred embodiment is the use of an expression construct or a vector as described herein for increasing pathogen resistance in a plant, plant part, or plant cell compared to a control plant, plant part, or plant cell.

Transgenic Organisms; Transgenic Plants, Plant Parts, and Plant Cells

A preferred embodiment is a transgenic plant, transgenic plant part, or transgenic plant cell overexpressing an exogenous RLK1 protein. Preferably, the RLK1 protein overexpressed in the plant, plant part or plant cell is encoded by (i) an exogenous nucleic acid having at least 60% identity with SEQ ID NO: 9, 1, 3, 8, 11-18, 19, 21, 23, 25, 27, 29, 31, or 33, or a functional fragment, thereof, an orthologue or a paralogue thereof, or a splice variant thereof; or by (ii) an exogenous nucleic acid encoding a protein having at least 60% identity with SEQ ID NO: 10, 2, 20, 22, 24, 26, 28, 30, 32, or 34, a functional fragment thereof, an orthologue or a paralogue thereof; preferably the encoded protein confers enhanced fungal resistance relative to control plants;

(iii) an exogenous nucleic acid capable of hybridizing under stringent conditions with a complementary sequence of any of the nucleic acids according to (i) or (ii); preferably encoding a RLK1 protein; preferably wherein the nucleic acid molecule codes for a polypeptide which has essentially identical properties to the polypeptide described in SEQ ID NO: 10 or 2; preferably the encoded protein confers enhanced fungal resistance relative to control plants; and/or by (iv) an exogenous nucleic acid encoding the same RLK1 protein as any of the nucleic acids of (i) to (iii) above, but differing from the nucleic acids of (i) to (iii) above due to the degeneracy of the genetic code.

Most preferably, the exogenous nucleic acid has at least 80%, at least 90%, at least 95%, at least 98%, at least 99% sequence identity, or even 100% sequence identity with SEQ ID NO: 1; or comprises an exogenous nucleic acid encoding a protein having at least 80%, at least 90%, at least 95%, at least 98%, at least 99% sequence identity, or even 100% sequence identity with SEQ ID NO: 2.

Most preferably, the exogenous nucleic acid has at least 80%, at least 90%, at least 95%, at least 98%, at least 99% sequence identity, or even 100% sequence identity with SEQ ID NO: 9; or comprises an exogenous nucleic acid encoding a protein having at least 80%, at least 90%, at least 95%, at least 98%, at least 99% sequence identity, or even 100% sequence identity with SEQ ID NO: 10.

A preferred embodiment is a transgenic plant, transgenic plant part, or transgenic plant cell overexpressing an exogenous RLK1 protein. Preferably, the RLK1 protein overexpressed in the plant, plant part or plant cell is encoded by (i) an exogenous nucleic acid having at least 60% identity with SEQ ID NO: 1 or a functional fragment, thereof, an orthologue or a paralogue thereof, or a splice variant thereof; or by (ii) an exogenous nucleic acid encoding a protein having at least 60% identity with SEQ ID NO: 2, a functional fragment thereof, an orthologue or a paralogue thereof; preferably the encoded protein confers enhanced fungal resistance relative to control plants;

(iii) an exogenous nucleic acid capable of hybridizing under stringent conditions with a complementary sequence of any of the nucleic acids according to (i) or (ii); preferably encoding a RLK1 protein; preferably wherein the nucleic acid molecule codes for a polypeptide which has essentially identical properties to the polypeptide described in SEQ ID NO: 10 or 2; preferably the encoded protein confers enhanced fungal resistance relative to control plants; and/or by (iv) an exogenous nucleic acid encoding the same RLK1 protein as any of the nucleic acids of (i) to (iii) above, but differing from the nucleic acids of (i) to (iii) above due to the degeneracy of the genetic code.

A preferred embodiment is a transgenic plant, transgenic plant part, or transgenic plant cell overexpressing an exogenous RLK1 protein. Preferably, the RLK1 protein overexpressed in the plant, plant part or plant cell is encoded by (i) an exogenous nucleic acid having at least 60% identity with SEQ ID NO: 9 or a functional fragment, thereof, an orthologue or a paralogue thereof, or a splice variant thereof; or by
(ii) an exogenous nucleic acid encoding a protein having at least 60% identity with SEQ ID NO: 10, a functional fragment thereof, an orthologue or a paralogue thereof; preferably the encoded protein confers enhanced fungal resistance relative to control plants;
(iii) an exogenous nucleic acid capable of hybridizing under stringent conditions with a complementary sequence of any of the nucleic acids according to (i) or (ii); preferably encoding a RLK1 protein; preferably wherein the nucleic acid molecule codes for a polypeptide which has essentially identical properties to the polypeptide described in SEQ ID NO: 10 or 2; preferably the encoded protein confers enhanced fungal resistance relative to control plants; and/or by
(iv) an exogenous nucleic acid encoding the same RLK1 protein as any of the nucleic acids of (i) to (iii) above, but differing from the nucleic acids of (i) to (iii) above due to the degeneracy of the genetic code.

Most preferably, the exogenous nucleic acid has at least 80%, at least 90%, at least 95%, at least 98%, at least 99% sequence identity, or even 100% sequence identity with SEQ ID NO: 9 or 1; or comprises an exogenous nucleic acid encoding a protein having at least 95%, at least 98%, at least 99% sequence identity, or even 100% sequence identity with SEQ ID NO: 10 or 2.

More preferably, the transgenic plant, transgenic plant part, or transgenic plant cell according to the present invention has been obtained by transformation with a recombinant vector described herein.

Suitable methods for transforming or transfecting host cells including plant cells are well known in the art of plant biotechnology. Any method may be used to transform the recombinant expression vector into plant cells to yield the transgenic plants of the invention. General methods for transforming dicotyledonous plants are disclosed, for example, in U.S. Pat. Nos. 4,940,838; 5,464,763, and the like. Methods for transforming specific dicotyledonous plants, for example, cotton, are set forth in U.S. Pat. Nos. 5,004,863; 5,159,135; and 5,846,797. Soy transformation methods are set forth in U.S. Pat. Nos. 4,992,375; 5,416,011; 5,569,834; 5,824,877; 6,384,301 and in EP 0301749B1 may be used. Transformation methods may include direct and indirect methods of transformation. Suitable direct methods include polyethylene glycol induced DNA uptake, liposome-mediated transformation (U.S. Pat. No. 4,536,475), biolistic methods using the gene gun (Fromm M E et al., Bio/Technology. 8(9):833-9, 1990; Gordon-Kamm et al. Plant Cell 2:603, 1990), electroporation, incubation of dry embryos in DNA-comprising solution, and microinjection. In the case of these direct transformation methods, the plasmids used need not meet any particular requirements. Simple plasmids, such as those of the pUC series, pBR322, M13mp series, pACYC184 and the like can be used. If intact plants are to be regenerated from the transformed cells, an additional selectable marker gene is preferably located on the plasmid. The direct transformation techniques are equally suitable for dicotyledonous and monocotyledonous plants.

Transformation can also be carried out by bacterial infection by means of *Agrobacterium* (for example EP 0 116 718), viral infection by means of viral vectors (EP 0 067 553; U.S. Pat. No. 4,407,956; WO 95/34668; WO 93/03161) or by means of pollen (EP 0 270 356; WO 85/01856; U.S. Pat. No. 4,684,611). *Agrobacterium* based transformation techniques (especially for dicotyledonous plants) are well known in the art. The *Agrobacterium* strain (e.g., *Agrobacterium tumefaciens* or *Agrobacterium rhizogenes*) comprises a plasmid (Ti or Ri plasmid) and a T-DNA element which is transferred to the plant following infection with *Agrobacterium*. The T-DNA (transferred DNA) is integrated into the genome of the plant cell. The T-DNA may be localized on the Ri- or Ti-plasmid or is separately comprised in a so-called binary vector. Methods for the *Agrobacterium*-mediated transformation are described, for example, in Horsch R B et al. (1985) Science 225:1229. The *Agrobacterium*-mediated transformation is best suited to dicotyledonous plants but has also been adapted to monocotyledonous plants. The transformation of plants by Agrobacteria is described in, for example, White F F, Vectors for Gene Transfer in Higher Plants, Transgenic Plants, Vol. 1, Engineering and Utilization, edited by S. D. Kung and R. Wu, Academic Press, 1993, pp. 15-38; Jenes B et al. Techniques for Gene Transfer, Transgenic Plants, Vol. 1, Engineering and Utilization, edited by S. D. Kung and R. Wu, Academic Press, 1993, pp. 128-143; Potrykus (1991) Annu Rev Plant Physiol Plant Molec Biol 42:205-225. Transformation may result in transient or stable transformation and expression. Although a nucleotide sequence of the present invention can be inserted into any plant and plant cell falling within these broad classes, it is particularly useful in crop plant cells.

The genetically modified plant cells can be regenerated via all methods with which the skilled worker is familiar. Suitable methods can be found in the abovementioned publications by S. D. Kung and R. Wu, Potrykus or Höfgen and Willmitzer.

After transformation, plant cells or cell groupings may be selected for the presence of one or more markers which are encoded by plant-expressible genes co-transferred with the gene of interest, following which the transformed material is regenerated into a whole plant. To select transformed plants, the plant material obtained in the transformation is, as a rule, subjected to selective conditions so that transformed plants can be distinguished from untransformed plants. For example, the seeds obtained in the above-described manner can be planted and, after an initial growing period, subjected to a suitable selection by spraying. A further possibility consists in growing the seeds, if appropriate after sterilization, on agar plates using a suitable selection agent so that only the transformed seeds can grow into plants. Alternatively, the transformed plants are screened for the presence of a selectable marker such as the ones described above. The transformed plants may also be directly selected by screening for the presence of the RLK1 nucleic acid.

Following DNA transfer and regeneration, putatively transformed plants may also be evaluated, for instance using Southern analysis, for the presence of the gene of interest, copy number and/or genomic organisation. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed and homozygous second-generation (or T2) transformants selected, and the T2 plants may then further be propagated through classical breeding techniques. The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

Preferably, the transgenic plant of the present invention or the plant obtained by the method of the present invention has increased resistance against fungal pathogens, preferably against rust pathogens (i.e., fungal pathogens of the order Pucciniales), preferably against fungal pathogens of the family Phakopsoraceae, more preferably against fungal pathogens of the genus *Phakopsora*, most preferably against *Phakopsora pachyrhizi* and *Phakopsora meibomiae*, also known as soybean rust. Preferably, resistance against *Phakopsora pachyrhizi* and/or *Phakopsora meibomiae* is increased.

Preferably, the plant, plant part, or plant cell is a plant or derived from a plant selected from the group consisting of beans, soya, pea, clover, kudzu, lucerne, lentils, lupins, vetches, groundnut, rice, wheat, barley, *arabidopsis*, lentil, banana, canola, cotton, potato, corn, sugar cane, alfalfa, and sugar beet.

In one embodiment of the present invention the plant is selected from the group consisting of beans, soya, pea, clover, kudzu, lucerne, lentils, lupins, vetches, and/or groundnut. Preferably, the plant is a legume, comprising plants of the genus *Phaseolus* (comprising French bean, dwarf bean, climbing bean (*Phaseolus vulgaris*), Lima bean (*Phaseolus lunatus* L.), Tepary bean (*Phaseolus acutifolius* A. Gray), runner bean (*Phaseolus coccineus*)); the genus *Glycine* (comprising *Glycine soja*, soybeans (*Glycine max* (L.) Merill)); pea (*Pisum*) (comprising shelling peas (*Pisum sativum* L. convar. *sativum*), also called smooth or round-seeded peas; marrowfat pea (*Pisum sativum* L. convar. medullare Alef. emend. C.O. Lehm), sugar pea (*Pisum sativum* L. convar. axiphium Alef emend. C.O. Lehm), also called snow pea, edible-podded pea or mangetout, (*Pisum granda* sneida L. convar. sneidulo p. shneiderium)); peanut (*Arachis hypogaea*), clover (*Trifolium* spec.), medick (*Medicago*), kudzu vine (*Pueraria lobata*), common lucerne, alfalfa (*M. sativa* L.), chickpea (*Cicer*), lentils (*Lens*) (*Lens culinaris* Medik.), lupins (*Lupinus*); vetches (*Vicia*), field bean, broad bean (*Vicia faba*), vetchling (*Lathyrus*) (comprising chickling pea (*Lathyrus sativus*), heath pea (*Lathyrus tuberosus*)); genus *Vigna* (comprising moth bean (*Vigna aconitifolia* (Jacq.) Maréchal), adzuki bean (*Vigna angularis* (Willd.) Ohwi & H. Ohashi), urd bean (*Vigna mungo* (L.) Hepper), mung bean (*Vigna radiata* (L.) R. Wilczek), bambara groundnut (*Vigna subterrane* (L.) Verdc.), rice bean (*Vigna umbellata* (Thunb.) Ohwi & H. Ohashi), *Vigna vexillata* (L.) A. Rich., *Vigna ungulculata* (L.) Walp., in the three subspecies asparagus bean, cowpea, catjang bean)); pigeonpea (*Cajanus cajan* (L.) Millsp.), the genus *Macrotyloma* (comprising geocarpa groundnut (*Macrotyloma geocarpum* (Harms) Maréchal & Baudet), horse bean (*Macrotyloma uniflorum* (Lam.) Verdc.); goa bean (*Psophocarpus tetragonolobus* (L.) DC.), African yam bean (*Sphenostylis stenocarpa* (Hochst. ex A. Rich.) Harms), Egyptian black bean, *dolichos* bean, lablab bean (*Lablab purpureus* (L.) Sweet), yam bean (*Pachyrhizus*), guar bean (*Cyamopsis tetragonolobus* (L.) Taub.); and/or the genus *Canavalia* (comprising jack bean (*Canavalia ensiformis* (L.) DC.), sword bean (*Canavalia gladiata* (Jacq.) DC.).

Further preferred is a plant selected from the group consisting of beans, soya, pea, clover, kudzu, lucerne, lentils, lupins, vetches, and groundnut. Most preferably, the plant, plant part, or plant cell is or is derived from soy.

Preferably, the transgenic plant of the present invention or the plant obtained by the method of the present invention is a soybean plant and has increased resistance against fungal pathogens of the order Pucciniales (rust), preferably, of the family Phacopsoraceae, more preferably against fungal pathogens of the genus *Phacopsora*, most preferably against *Phakopsora pachyrhizi* and *Phakopsora meibomiae*, also known as soybean rust. Preferably, resistance against *Phakopsora pachyrhizi* and/or *Phakopsora meibomiae* is increased.

Methods for the Production of Transgenic Plants

One embodiment according to the present invention provides a method for producing a transgenic plant, a transgenic plant part, or a transgenic plant cell resistant to a fungal pathogen, preferably of the family Phacosporaceae, for example soybean rust, wherein the recombinant nucleic acid used to generate a transgenic plant comprises a promoter that is functional in the plant cell, operably linked to an RLK1 nucleic acid, which is preferably SEQ ID NO: 1 or 3, and a terminator regulatory sequence.

In one embodiment, the present invention refers to a method for the production of a transgenic plant, transgenic plant part, or transgenic plant cell having increased fungal resistance, comprising (a) introducing a recombinant vector construct according to the present invention into a plant, a plant part or a plant cell and (b) generating a transgenic plant from the plant, plant part or plant cell.

Preferably, the method for the production of the transgenic plant, transgenic plant part, or transgenic plant cell further comprises the step (c) expressing the RLK1 protein, preferably encoded by
   (i) an exogenous nucleic acid having at least 60% identity with SEQ ID NO: 9, 1, 3, 8, 11-18, 19, 21, 23, 25, 27, 29, 31, or 33, a functional fragment thereof, an orthologue or a paralogue thereof, or a splice variant thereof;
   (ii) an exogenous nucleic acid encoding a protein having at least 60% identity with SEQ ID NO: 10, 2, 20, 22, 24, 26, 28, 30, 32, or 34, or a functional fragment thereof, an orthologue or a paralogue thereof; preferably the encoded protein confers enhanced fungal resistance relative to control plants;
   (iii) an exogenous nucleic acid capable of hybridizing under stringent conditions with a complementary sequence of any of the nucleic acids according to (i) or (ii); preferably encoding a RLK1 protein; preferably wherein the nucleic acid molecule codes for a polypeptide which has essentially identical properties to the polypeptide described in SEQ ID NO: 10 or 2; preferably the encoded protein confers enhanced fungal resistance relative to control plants; and/or by
   (iv) an exogenous nucleic acid encoding the same RLK1 protein as any of the nucleic acids of (i) to (iii) above, but differing from the nucleic acids of (i) to (iii) above due to the degeneracy of the genetic code.

Preferably, said introducing and expressing does not comprise an essentially biological process.

More preferably, the method for the production of the transgenic plant, transgenic plant part, or transgenic plant cell further comprises the step (c) expressing the RLK1 protein, preferably encoded by
   (i) an exogenous nucleic acid having at least 60% identity with SEQ ID NO: 1, a functional fragment thereof, an orthologue or a paralogue thereof, or a splice variant thereof;

(ii) an exogenous nucleic acid encoding a protein having at least 60% identity with SEQ ID NO: 2, or a functional fragment thereof, an orthologue or a paralogue thereof; preferably the encoded protein confers enhanced fungal resistance relative to control plants;
(iii) an exogenous nucleic acid capable of hybridizing under stringent conditions with a complementary sequence of any of the nucleic acids according to (i) or (ii); preferably encoding a RLK1 protein; preferably wherein the nucleic acid molecule codes for a polypeptide which has essentially identical properties to the polypeptide described in SEQ ID NO: 10 or 2; preferably the encoded protein confers enhanced fungal resistance relative to control plants; and/or by
(iv) an exogenous nucleic acid encoding the same RLK1 protein as any of the nucleic acids of (i) to (iii) above, but differing from the nucleic acids of (i) to (iii) above due to the degeneracy of the genetic code.

More preferably, the method for the production of the transgenic plant, transgenic plant part, or transgenic plant cell further comprises the step
(c) expressing the RLK1 protein, preferably encoded by
  (i) an exogenous nucleic acid having at least 60% Identity with SEQ ID NO: 9, a functional fragment thereof, an orthologue or a paralogue thereof, or a splice variant thereof;
  (ii) an exogenous nucleic acid encoding a protein having at least 60% identity with SEQ ID NO: 10, or a functional fragment thereof, an orthologue or a paralogue thereof; preferably the encoded protein confers enhanced fungal resistance relative to control plants;
  (iii) an exogenous nucleic acid capable of hybridizing under stringent conditions with a complementary sequence of any of the nucleic acids according to (i) or (ii); preferably encoding a RLK1 protein; preferably wherein the nucleic acid molecule codes for a polypeptide which has essentially identical properties to the polypeptide described in SEQ ID NO: 10 or 2; preferably the encoded protein confers enhanced fungal resistance relative to control plants; and/or by
  (iv) an exogenous nucleic acid encoding the same RLK1 protein as any of the nucleic acids of (i) to (iii) above, but differing from the nucleic acids of (i) to (iii) above due to the degeneracy of the genetic code.

Preferably, the method for the production of the transgenic plant, transgenic plant part, or transgenic plant cell further comprises the step of selecting a transgenic plant expressing
(i) an exogenous nucleic acid having at least 60% identity, preferably at least 70% sequence identity, at least 80%, at least 90%, at least 95%, at least 98%, at least 99% sequence identity, or even 100% sequence identity with SEQ ID NO: 9, 1, 3, 8, 11-18, 19, 21, 23, 25, 27, 29, 31, or 33, or a functional fragment thereof, or an orthologue or a paralogue thereof, or a splice variant thereof;
(ii) an exogenous nucleic acid coding for a protein having at least 60% Identity, preferably at least 70% sequence identity, at least 80%, at least 90%, at least 95%, at least 98%, at least 99% sequence identity, or even 100% sequence identity with SEQ ID NO: 10, 2, 20, 22, 24, 26, 28, 30, 32, or 34, a functional fragment thereof, an orthologue or a paralogue thereof; preferably the encoded protein confers enhanced fungal resistance relative to control plants;
(iii) an exogenous nucleic acid capable of hybridizing under stringent conditions with a complementary sequence of any of the nucleic acids according to (i) or (ii); preferably encoding a RLK1 protein; preferably wherein the nucleic acid molecule codes for a polypeptide which has essentially identical properties to the polypeptide described in SEQ ID NO: 10 or 2; preferably the encoded protein confers enhanced fungal resistance relative to control plants; and/or
(iv) an exogenous nucleic acid encoding the same RLK1 polypeptide as any of the nucleic acids of (i) to (iii) above, but differing from the nucleic acids of (i) to (iii) above due to the degeneracy of the genetic code.

Preferably, the method for the production of the transgenic plant, transgenic plant part, or transgenic plant cell additionally comprises the step of harvesting the seeds of the transgenic plant and planting the seeds and growing the seeds to plants, wherein the grown plant(s) comprises
(i) the exogenous nucleic acid having at least 60% identity with SEQ ID NO: 9, 1, 3, 8, 11-18, 19, 21, 23, 25, 27, 29, 31, or 33, a functional fragment thereof, an orthologue or a paralogue thereof, or a splice variant thereof;
(ii) the exogenous nucleic acid encoding a protein having at least 60% identity with SEQ ID NO: 10, 2, 20, 22, 24, 26, 28, 30, 32, or 34, or a functional fragment thereof, an orthologue or a paralogue thereof; preferably the encoded protein confers enhanced fungal resistance relative to control plants;
(iii) the exogenous nucleic acid capable of hybridizing under stringent conditions with a complementary sequence of any of the nucleic acids according to (i) or (ii); preferably encoding a RLK1 protein; preferably wherein the nucleic acid molecule codes for a polypeptide which has essentially identical properties to the polypeptide described in SEQ ID NO: 10 or 2; preferably the encoded protein confers enhanced fungal resistance relative to control plants; and/or
(iv) the exogenous nucleic acid encoding the same RLK1 protein as any of the nucleic acids of (i) to (iii) above, but differing from the nucleic acids of (i) to (iii) above due to the degeneracy of the genetic code;
preferably, the step of harvesting the seeds of the transgenic plant and planting the seeds and growing the seeds to plants, wherein the grown plant(s) comprises
(i) the exogenous nucleic acid having at least 60% identity with SEQ ID NO: 9, 1, 3, 8, 11-18, 19, 21, 23, 25, 27, 29, 31, or 33, a functional fragment thereof, an orthologue or a paralogue thereof, or a splice variant thereof;
(ii) the exogenous nucleic acid encoding a protein having at least 60% Identity with SEQ ID NO: 10, 2, 20, 22, 24, 26, 28, 30, 32, or 34, or a functional fragment thereof, an orthologue or a paralogue thereof; preferably the encoded protein confers enhanced fungal resistance relative to control plants;
(iii) the exogenous nucleic acid capable of hybridizing under stringent conditions with a complementary sequence of any of the nucleic acids according to (i) or (ii); preferably encoding a RLK1 protein; preferably wherein the nucleic acid molecule codes for a polypeptide which has essentially identical properties to the polypeptide described in SEQ ID NO: 10 or 2; preferably the encoded protein confers enhanced fungal resistance relative to control plants; and/or
(iv) the exogenous nucleic acid encoding the same RLK1 protein as any of the nucleic acids of (i) to (iii) above, but differing from the nucleic acids of (i) to (iii) above due to the degeneracy of the genetic code;
is repeated more than one time, preferably, 1, 2, 3, 4, 5, 6, 8, 9, 10, 15, 20, 25, 30, 35, 40, 45, or 50 times.

The transgenic plants may be selected by known methods as described above (e.g., by screening for the presence of one or more markers which are encoded by plant-expressible genes co-transferred with the RLK1 gene or by directly screening for the RLK1 nucleic acid).

Furthermore, the use of the exogenous RLK1 nucleic acid or the recombinant vector construct comprising the RLK1 nucleic acid for the transformation of a plant, plant part, or plant cell to provide a fungal resistant plant, plant part, or plant cell is provided.

Harvestable Parts and Products

Harvestable parts of the transgenic plant according to the present invention are part of the invention. Preferably, the harvestable parts comprise the RLK1 nucleic acid or RLK1 protein. The harvestable parts may be seeds, roots, leaves and/or flowers comprising the RLK1 nucleic acid or RLK1 protein or parts thereof. Preferred parts of soy plants are soy beans comprising the RLK1 nucleic acid or RLK1 protein.

Products derived from a transgenic plant according to the present invention, parts thereof or harvestable parts thereof are part of the invention. A preferred product is meal or oil, preferably, soybean meal or soybean oil. Preferably, the soybean meal and/or oil comprises the RLK1 nucleic acid or RLK1 protein.

Preferably the harvestable parts of the transgenic plant according to the present invention or the products derived from a transgenic plant comprise an exogenous nucleic acid molecule consisting of or comprising a nucleic acid selected from the group consisting of:

(i) a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 9, 1, 3, 8, 11-18, 19, 21, 23, 25, 27, 29, 31, or 33, or a functional fragment, derivative, orthologue, or paralogue thereof, or a splice variant thereof;

(ii) a nucleic acid encoding a RLK1 protein having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 10, 2, 20, 22, 24, 26, 28, 30, 32, or 34, or a functional fragment, derivative, orthologue, or paralogue thereof; preferably the RLK1 protein has essentially the same biological activity as a RLK1 protein encoded by SEQ ID NO: 9, 1, 3, or 8; preferably the RLK1 protein confers enhanced fungal resistance relative to control plants; preferably the RLK1 protein has receptor like kinase activity;

(iii) a nucleic acid molecule which hybridizes with a complementary sequence of any of the nucleic acid molecules of (i) or (ii) under high stringency hybridization conditions; preferably encoding a RLK1 protein; preferably wherein the nucleic acid molecule codes for a polypeptide which has essentially identical properties to the polypeptide described in SEQ ID NO: 10 or 2; preferably the encoded protein confers enhanced fungal resistance relative to control plants; and (iv) a nucleic acid encoding the same RLK1 protein as the RLK1 nucleic acids of (i) to (ii) above, but differing from the RLK1 nucleic acids of (i) to (ii) above due to the degeneracy of the genetic code;

or wherein the harvestable part of the transgenic plant or the product derived from the transgenic plant comprises a RLK1 protein encoded by any one of the RLK1 nucleic acids of (i) to (iv).

Methods for Manufacturing a Product

In one embodiment the method for the production of a product comprises a) growing the plants of the invention or obtainable by the methods of invention and b) producing said product from or by the plants of the invention and/or parts, e.g. seeds, of these plants.

In a further embodiment the method comprises the steps a) growing the plants of the invention, b) removing the harvestable parts as defined above from the plants and c) producing said product from or by the harvestable parts of the invention.

Preferably the products obtained by said method comprises an exogenous nucleic acid molecule consisting of or comprising a nucleic acid selected from the group consisting of:

(i) a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 9, 1, 3, 8, 11-18, 19, 21, 23, 25, 27, 29, 31, or 33, or a functional fragment, derivative, orthologue, or paralogue thereof, or a splice variant thereof;

(ii) a nucleic acid encoding a RLK1 protein having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 10, 2, 20, 22, 24, 26, 28, 30, 32, or 34, or a functional fragment, derivative, orthologue, or paralogue thereof; preferably the RLK1 protein has essentially the same biological activity as a RLK1 protein encoded by SEQ ID NO: 9, 1, 3, or 8; preferably the RLK1 protein confers enhanced fungal resistance relative to control plants; preferably the RLK1 protein has receptor like kinase activity;

(iii) a nucleic acid molecule which hybridizes with a complementary sequence of any of the nucleic acid molecules of (i) or (ii) under high stringency hybridization conditions; preferably encoding a RLK1 protein; preferably wherein the nucleic acid molecule codes for a polypeptide which has essentially identical properties to the polypeptide described in SEQ ID NO: 10 or 2; preferably the encoded protein confers enhanced fungal resistance relative to control plants; and (iv) a nucleic acid encoding the same RLK1 protein as the RLK1 nucleic acids of (i) to (ii) above, but differing from the RLK1 nucleic acids of (i) to (ii) above due to the degeneracy of the genetic code;

or wherein the product obtained by said method comprises a RLK1 protein encoded by any one of the RLK1 nucleic acids of (i) to (iv).

The product may be produced at the site where the plant has been grown, the plants and/or parts thereof may be removed from the site where the plants have been grown to produce the product. Typically, the plant is grown, the desired harvestable parts are removed from the plant, if feasible in repeated cycles, and the product made from the harvestable parts of the plant. The step of growing the plant may be performed only once each time the methods of the invention is performed, while allowing repeated times the steps of product production e.g. by repeated removal of harvestable parts of the plants of the invention and if necessary further processing of these parts to arrive at the product. It is also possible that the step of growing the plants of the invention is repeated and plants or harvestable parts are stored until the production of the product is then performed once for the accumulated plants or plant parts. Also, the steps of growing the plants and producing the product may be performed with an overlap in time, even simultaneously to a large extend or sequentially. Generally the plants are grown for some time before the product is produced.

In one embodiment the products produced by said methods of the invention are plant products such as, but not limited to, a foodstuff, feedstuff, a food supplement, feed supplement, fiber, cosmetic and/or pharmaceutical. Foodstuffs are regarded as compositions used for nutrition and/or for supplementing nutrition. Animal feedstuffs and animal feed supplements, in particular, are regarded as foodstuffs.

In another embodiment the inventive methods for the production are used to make agricultural products such as, but not limited to, plant extracts, proteins, amino acids, carbohydrates, fats, oils, polymers, vitamins, and the like.

It is possible that a plant product consists of one or more agricultural products to a large extent.

Methods for Breeding/Methods for Plant Improvement/Methods Plant Variety Production The transgenic plants of the invention may be crossed with similar transgenic plants or with transgenic plants lacking the nucleic acids of the invention or with non-transgenic plants, using known methods of plant breeding, to prepare seeds. Further, the transgenic plant cells or plants of the present invention may comprise, and/or be crossed to another transgenic plant that comprises one or more exogenous nucleic acids, thus creating a "stack" of transgenes in the plant and/or its progeny. The seed is then planted to obtain a crossed fertile transgenic plant comprising the RLK1 nucleic acid. The crossed fertile transgenic plant may have the particular expression cassette inherited through a female parent or through a male parent. The second plant may be an inbred plant. The crossed fertile transgenic may be a hybrid. Also included within the present invention are seeds of any of these crossed fertile transgenic plants. The seeds of this invention can be harvested from fertile transgenic plants and be used to grow progeny generations of transformed plants of this invention including hybrid plant lines comprising the exogenous nucleic acid.

Thus, one embodiment of the present invention is a method for breeding a fungal resistant plant comprising the steps of (a) crossing a transgenic plant described herein or a plant obtainable by a method described herein with a second plant;
(b) obtaining a seed or seeds resulting from the crossing step described in (a);
(c) planting said seed or seeds and growing the seed or seeds to plants; and
(d) selecting from said plants the plants expressing an RLK1 protein, preferably encoded by
  (i) an exogenous nucleic acid having at least 60% identity with SEQ ID NO: 9, 1, 3, 8, 11-18, 19, 21, 23, 25, 27, 29, 31, or 33, a functional fragment thereof, an orthologue or a paralogue thereof, or a splice variant thereof;
  (ii) an exogenous nucleic acid encoding a protein having at least 60% identity with SEQ ID NO: 10, 2, 20, 22, 24, 26, 28, 30, 32, or 34, or a functional fragment thereof, an orthologue or a paralogue thereof; preferably the encoded protein confers enhanced fungal resistance relative to control plants;
  (iii) an exogenous nucleic acid capable of hybridizing under stringent conditions with with a complementary sequence of any of the nucleic acids according to (i) or (ii); preferably encoding a RLK1 protein; preferably wherein the nucleic acid molecule codes for a polypeptide which has essentially identical properties to the polypeptide described in SEQ ID NO: 10 or 2; preferably the encoded protein confers enhanced fungal resistance relative to control plants; and/or by
  (iv) an exogenous nucleic acid encoding the same RLK1 protein as any of the nucleic acids of (i) to (iii) above, but differing from the nucleic acids of (i) to (iii) above due to the degeneracy of the genetic code.

Another preferred embodiment is a method for plant improvement comprising (a) obtaining a transgenic plant by any of the methods of the present invention;
(b) combining within one plant cell the genetic material of at least one plant cell of the plant of (a) with the genetic material of at least one cell differing in one or more gene from the plant cells of the plants of (a) or crossing the transgenic plant of (a) with a second plant;
(c) obtaining seed from at least one plant generated from the one plant cell of (b) or the plant of the cross of step (b);
(d) planting said seeds and growing the seeds to plants; and
(e) selecting from said plants, plants expressing the nucleic acid encoding the RLK1 protein; and optionally
(f) producing propagation material from the plants expressing the nucleic acid encoding the RLK1 protein.

The transgenic plants may be selected by known methods as described above (e.g., by screening for the presence of one or more markers which are encoded by plant-expressible genes co-transferred with the RLK1 gene or screening for the RLK1 nucleic acid itself).

According to the present invention, the introduced RLK1 nucleic acid may be maintained in the plant cell stably if it is incorporated into a non-chromosomal autonomous replicon or integrated into the plant chromosomes. Whether present in an extra-chromosomal nonreplicating or replicating vector construct or a vector construct that is integrated into a chromosome, the exogenous RLK1 nucleic acid preferably resides in a plant expression cassette. A plant expression cassette preferably contains regulatory sequences capable of driving gene expression in plant cells that are functional linked so that each sequence can fulfill its function, for example, termination of transcription by polyadenylation signals. Preferred polyadenylation signals are those originating from *Agrobacterium tumefaciens* t-DNA such as the gene 3 known as octopine synthase of the Ti-plasmid pTiACH5 (Gielen et al., 1984, EMBO J. 3:835) or functional equivalents thereof, but also all other terminators functionally active in plants are suitable. As plant gene expression is very often not limited on transcriptional levels, a plant expression cassette preferably contains other functional linked sequences like translational enhancers such as the overdrive-sequence containing the 5'-untranslated leader sequence from tobacco mosaic virus increasing the polypeptide per RNA ratio (Gallie et al., 1987, Nucl. Acids Research 15:8693-8711). Examples of plant expression vectors include those detailed in: Becker, D. et al., 1992, New plant binary vectors with selectable markers located proximal to the left border, Plant Mol. Biol. 20:1195-1197; Bevan, M. W., 1984, Binary *Agrobacterium* vectors for plant transformation, Nucl. Acid. Res. 12:8711-8721; and Vectors for Gene Transfer in Higher Plants; in: Transgenic Plants, Vol. 1, Engineering and Utilization, eds.: Kung and R. Wu, Academic Press, 1993, S. 15-38.

Examples

The following examples are not intended to limit the scope of the claims to the invention, but are rather intended to be exemplary of certain embodiments. Any variations in the exemplified methods that occur to the skilled artisan are intended to fall within the scope of the present invention.

Example 1: General Methods

The chemical synthesis of oligonucleotides can be affected, for example, in the known fashion using the phosphoamidite method (Voet, Voet, 2nd Edition, Wiley Press New York, pages 896-897). The cloning steps carried out for the purposes of the present invention such as, for example, restriction cleavages, agarose gel electrophoresis, purification of DNA fragments, transfer of nucleic acids to nitrocellulose and nylon membranes, linking DNA fragments, transformation of *E. coli* cells, bacterial cultures, phage multiplication and sequence analysis of recombinant DNA, are carried out as described by Sambrook et al. Cold Spring Harbor Laboratory Press (1989), ISBN 0-87969-309-6. The sequencing of recombinant DNA molecules is carried out with an MWG-Licor laser fluorescence DNA sequencer following the method of Sanger (Sanger et al., Proc. Natl. Acad. Sci. USA 74, 5463 (1977)).

Example 2: Cloning of Overexpression Vector Constructs

A complex cDNA library was produced from *Arabidopsis thaliana* (ecotype Col-0) RNA by using the Superscript II cDNA synthesis kit (Invitrogen). All steps of cDNA preparation and purification were performed according as described in the manual.

First, the RLK1 sequence from 5'UTR to 3'UTR (including the full-length HCP5) was specifically amplified from the cDNA by PCR as described in the protocol of the Phusion hot-start polymerase (Finnzymes). The composition of the PCR (according to the protocol of the Phusion hot-start polymerase) was as follows: 1×PCR buffer, 1 mM of each dNTP, 100 ng cDNA of *Arabidopsis thaliana* (var Columbia-0, see above), 40 pmol forward primer, 40 pmol reverse primer, 1 µl Phusion hot-start polymerase.

The amplification cycles were as follows:
1 cycle of 30 seconds at 98° C., followed by 35 cycles of in each case 10 seconds at 98° C., 30 seconds at 58° C. and 30 seconds at 72° C., followed by 1 cycle of 10 minutes at 72° C., then 14° C.

The primers (as shown in SEQ ID NO: 4 and 5) were designed in a way that the specifically bind to sequences in the 5' UTR upstream of the start ATG and in the 3'UTR downstream of the stop codon of the HCP-5 coding sequence.

```
i) foward primer:
                                    (SEQ ID NO: 4)
5'-GGCTGGAGGCTGGAGATTATTTGG-3' ii) reverse primer:
                                    (SEQ ID NO: 5)
5'-AAGGCATGGTCGGTGCTATC-3'
```

The amplified fragment was eluated and purified from an 1% agarose gel by using the Nucleospin Extract II Kit (Macherey und Nagel, dueren, Germany). To generate a cDNA fragment that contains attB sites for further GATEWAY (Invitrogen) cloning, a Re-PCR was performed using the Phusion hot-start polymerase (Finnzymes).

The composition of the PCR (according to the protocol of the Phusion hot-start polymerase) was as follows: 1×PCR buffer, 1 mM of each dNTP, 10-50 ng template DNA derived from the previous PCR, 40 pmol forward primer, 40 pmol reverse primer, 1 µl Phusion hot-start polymerase.

The amplification cycles were as follows:
cycle of 30 seconds at 98° C., followed by 35 cycles of in each case 10 seconds at 98° C., 30 seconds at 70° C. and 60 seconds at 72° C., followed by 1 cycle of 10 minutes at 72° C., then 14° C.

The primer sequences were designed to specifically amplify the RLK1 ORF (Start-ATG to stop) and to add attB sites for GATEWAY® (Invitrogen, Life Technologies, Carlsbad, Calif., USA) mediated cloning of the plant transformation vector:

```
i) foward primer:
                                    (SEQ ID NO: 6)
5'-GGGGACAAGTTTGTACAAAAAAGCAGGCTATGAGACTTT
ACTTATC-3' ii) reverse primer:
                                    (SEQ ID NO: 7)
5'-GGGGACCACTTTGTACAAGAAAGCTGGGTTTATTTACTC
CTATCATCGTCG-3'
```

The amplified fragment was cloned into a Gateway pEN-TRY-B vector (Invitrogen, Life Technologies, Carlsbad, Calif., USA) by using a conventional GATEWAY® BP-reaction according to the manual of the supplier (Invitrogen). The BP reaction was performed in a way that the full-length RLK1 fragment is located in sense direction between the attL1 and attL2 recombination sites.

It is also possible to generate all DNA fragments mentioned in this invention by DNA synthesis (Geneart, Regensburg, Germany).

Figure 2:
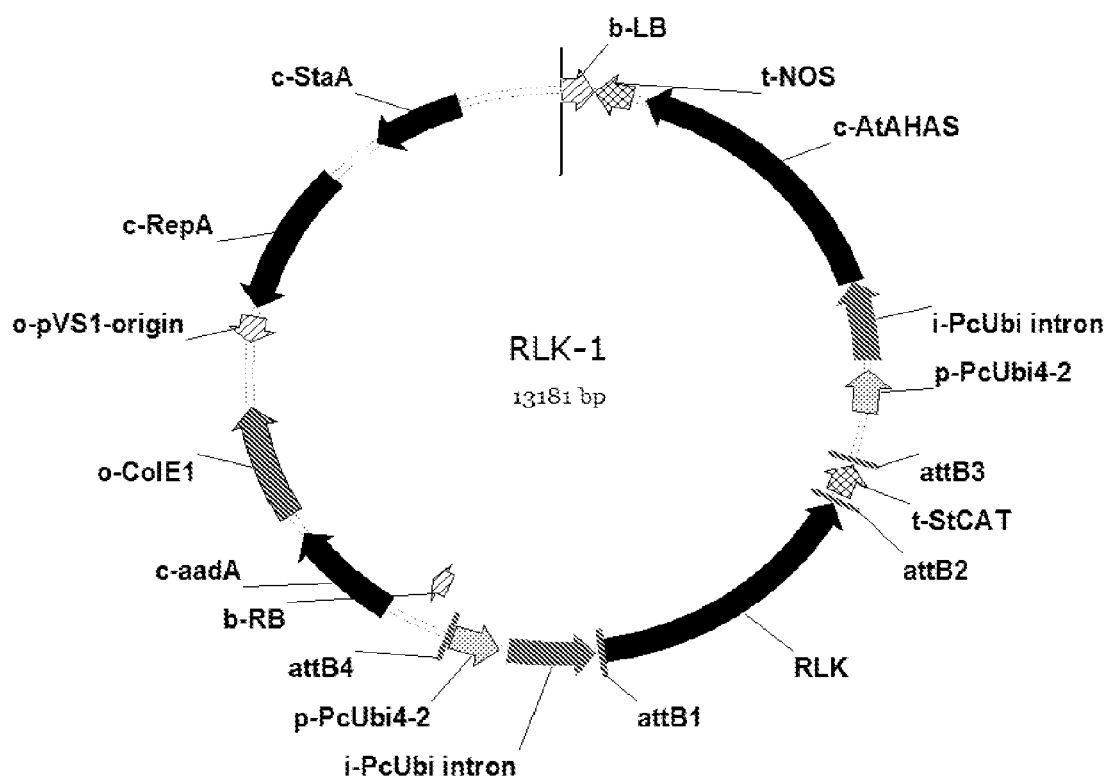
FIG. 2 shows the schematic illustration of the plant transformation vector harboring the RLK1 nucleic acid under control of the parsley ubiquitine promoter.

To obtain the binary plant transformation vector, a triple LR reaction (Gateway system, Invitrogen, Life Technologies, Carlsbad, Calif., USA) was performed according to manufacturer's protocol by using a pENTRY-A vector containing a parsley ubiquitine promoter, the RLK1 gene in a pENTRY-B vector and a pENTRY-C vector containing the terminator of the cathepsin D inhibitor gene from *Solanum tuberosum*. As target a binary pDEST vector was used which is composed of: (1) a Spectinomycin/Streptomycin resistance cassette for bacterial selection, (2) a pVS1 origin of replication in Agrobacteria, (3) a pBR322 origin of replication for stable maintenance in *E. coli*, and (4) between the right and left border an AHAS selection under control of a pcUbi-promoter (see FIG. 2). The recombination reaction was transformed into *E. coli* (DH5alpha), mini-prepped and screened by specific restriction digestions. A positive clone from each vector construct was sequenced and submitted soy transformation.

Example 3: Soy Transformation

The expression vector constructs (see example 2) were transformed into soy. 3.1 Sterilization and Germination of Soy Seeds Virtually any seed of any soy variety can be employed in the method of the invention. A variety of soybean cultivar (including Jack, Williams 82, Jake, Stoddard and Resnik) is appropriate for soy transformation. Soy seeds were sterilized in a chamber with a chlorine gas produced by adding 3.5 ml 12N HCl drop wise into 100 ml bleach (5.25% sodium hypochlorite) in a desiccator with a tightly fitting lid. After 24 to 48 hours in the chamber, seeds were removed and approximately 18 to 20 seeds were plated on solid GM medium with or without 5 µM 6-benzyl-aminopurine (BAP) in 100 mm Petri dishes. Seedlings without BAP are more elongated and roots develop, especially secondary and lateral root formation. BAP strengthens the seedling by forming a shorter and stockier seedling.

Seven-day-old seedlings grown in the light (>100 µEinstein/m$^2$s) at 25° C. were used for explant material for the three-explant types. At this time, the seed coat was split, and the epicotyl with the unifoliate leaves have grown to, at minimum, the length of the cotyledons. The epicotyl should be at least 0.5 cm to avoid the cotyledonary-node tissue (since soycultivars and seed lots may vary in the developmental time a description of the germination stage is more accurate than a specific germination time).

For inoculation of entire seedlings, see Method A (example 3.3.1 and 3.3.2) or leaf explants, see Method B (example 3.3.3).

For method C (see example 3.3.4), the hypocotyl and one and a half or part of both cotyledons were removed from each seedling. The seedlings were then placed on propagation media for 2 to 4 weeks. The seedlings produce several branched shoots to obtain explants from. The majority of the explants originated from the plantlet growing from the apical bud. These explants were preferably used as target tissue.

3.2—Growth and Preparation of *Agrobacterium* Culture

*Agrobacterium* cultures were prepared by streaking *Agrobacterium* (e.g., *A. tumefaciens* or *A. rhizogenes*) carrying the desired binary vector (e.g. H. Klee. R. Horsch and S. Rogers 1987 *Agrobacterium*-Mediated Plant Transformation and its further Applications to Plant Biology; Annual Review of Plant Physiology Vol. 38: 467-486) onto solid YEP growth medium (YEP media: 10 g yeast extract, 10 g Bacto Peptone, 5 g NaCl, Adjust pH to 7.0, and bring final volume to 1 liter with H2O, for YEP agar plates add 20 g Agar, autoclave) and incubating at 25° C. until colonies appeared (about 2 days). Depending on the selectable marker genes present on the Ti or Ri plasmid, the binary vector, and the bacterial chromosomes, different selection compounds were be used for *A. tumefaciens* and *A. rhizogenes* selection in the YEP solid and liquid media. Various *Agrobacterium* strains can be used for the transformation method.

After approximately two days, a single colony (with a sterile toothpick) was picked and 50 ml of liquid YEP was inoculated with antibiotics and shaken at 175 rpm (25° C.) until an OD$_{600}$ between 0.8-1.0 is reached (approximately 2 d). Working glycerol stocks (15%) for transformation are prepared and one-ml of *Agrobacterium* stock aliquoted into 1.5 ml Eppendorf tubes then stored at −80° C.

The day before explant inoculation, 200 ml of YEP were inoculated with 5 µl to 3 ml of working *Agrobacterium* stock in a 500 ml Erlenmeyer flask. The flask was shaken overnight at 25° C. until the OD$_{600}$ was between 0.8 and 1.0. Before preparing the soy explants, the Agrobacteria were pelleted by centrifugation for 10 min at 5,500×g at 20° C. The pellet was resuspended in liquid CCM to the desired density (OD$_{600}$ 0.5-0.8) and placed at room temperature at least 30 min before use.

3.3—Explant Preparation and Co-Cultivation (Inoculation)
3.3.1 Method A: Explant Preparation on the Day of Transformation Seedlings at this time had elongated epicotyls from at least 0.5 cm but generally between 0.5 and 2 cm. Elongated epicotyls up to 4 cm in length had been successfully employed. Explants were then prepared with: 1) with or without some roots, ii) with a partial, one or both cotyledons, all preformed leaves were removed including apical meristem, and the node located at the first set of leaves was injured with several cuts using a sharp scalpel.

This cutting at the node not only induced *Agrobacterium* infection but also distributed the axillary meristem cells and damaged pre-formed shoots. After wounding and preparation, the explants were set aside in a Petri dish and subsequently co-cultivated with the liquid CCM/*Agrobacterium* mixture for 30 minutes. The explants were then removed from the liquid medium and plated on top of a sterile filter paper on 15×100 mm Petri plates with solid co-cultivation medium. The wounded target tissues were placed such that they are in direct contact with the medium.

3.3.2 Modified Method A: Epicotyl Explant Preparation

Soyepicotyl segments prepared from 4 to 8 d old seedlings were used as explants for regeneration and transformation. Seeds of soya cv. L00106CN, 93-41131 and Jack were germinated in ⅒ MS salts or a similar composition medium with or without cytokinins for 4 to 8 d. Epicotyl explants were prepared by removing the cotyledonary node and stem node from the stem section. The epicotyl was cut into 2 to 5 segments. Especially preferred are segments attached to the primary or higher node comprising axillary meristematic tissue.

The explants were used for *Agrobacterium* infection. *Agrobacterium* AGL1 harboring a plasmid with the gene of interest (GOI) and the AHAS, bar or dsdA selectable marker gene was cultured in LB medium with appropriate antibiotics overnight, harvested and resuspended in a inoculation medium with acetosyringone. Freshly prepared epicotyl segments were soaked in the *Agrobacterium* suspension for 30 to 60 min and then the explants were blotted dry on sterile filter papers. The inoculated explants were then cultured on a coculture medium with L-cysteine and TTD and other chemicals such as acetosyringone for increasing T-DNA delivery for 2 to 4 d. The infected epicotyl explants were then placed on a shoot induction medium with selection agents such as imazapyr (for AHAS gene), glufosinate (for bar gene), or D-serine (for dsdA gene). The regenerated shoots were subcultured on elongation medium with the selective agent.

For regeneration of transgenic plants the segments were then cultured on a medium with cytokinins such as BAP, TDZ and/or Kinetin for shoot induction. After 4 to 8 weeks, the cultured tissues were transferred to a medium with lower concentration of cytokinin for shoot elongation. Elongated shoots were transferred to a medium with auxin for rooting and plant development. Multiple shoots were regenerated.

Many stable transformed sectors showing strong cDNA expression were recovered. Soybean plants were regenerated from epicotyl explants. Efficient T-DNA delivery and stable transformed sectors were demonstrated.

3.3.3 Method B: Leaf Explants

For the preparation of the leaf explant the cotyledon was removed from the hypocotyl. The cotyledons were separated from one another and the epicotyl is removed. The primary leaves, which consist of the lamina, the petiole, and the stipules, were removed from the epicotyl by carefully cutting at the base of the stipules such that the axillary meristems were included on the explant. To wound the explant as well as to stimulate de novo shoot formation, any pre-formed shoots were removed and the area between the stipules was cut with a sharp scalpel 3 to 5 times.

The explants are either completely immersed or the wounded petiole end dipped into the *Agrobacterium* suspension immediately after explant preparation. After inoculation, the explants are blotted onto sterile filter paper to remove excess *Agrobacterium* culture and place explants with the wounded side in contact with a round 7 cm Whatman paper overlaying the solid CCM medium (see above). This filter paper prevents *A. tumefaciens* overgrowth on the soy-explants. Wrap five plates with Parafilm™ "M" (American National Can, Chicago, Ill., USA) and incubate for three to five days in the dark or light at 25° C.

3.3.4 Method C: Propagated Axillary Meristem

For the preparation of the propagated axillary meristem explant propagated 3-4 week-old plantlets were used. Axillary meristem explants can be pre-pared from the first to the fourth node. An average of three to four explants could be obtained from each seedling. The explants were prepared from plantlets by cutting 0.5 to 1.0 cm below the axillary node on the internode and removing the petiole and leaf from the explant. The tip where the axillary meristems lie was cut with a scalpel to induce de novo shoot growth and allow access of target cells to the *Agrobacterium*. Therefore, a 0.5 cm explant included the stem and a bud.

Once cut, the explants were immediately placed in the *Agrobacterium* suspension for 20 to 30 minutes. After inoculation, the explants were blotted onto sterile filter paper to remove excess *Agrobacterium* culture then placed almost completely immersed in solid CCM or on top of a round 7 cm filter paper overlaying the solid CCM, depending on the *Agrobacterium* strain. This filter paper prevents *Agrobacterium* overgrowth on the soy-explants. Plates were wrapped with Parafilm™ "M" (American National Can, Chicago, Ill., USA) and incubated for two to three days in the dark at 25° C.

3.4—Shoot Induction

After 3 to 5 days co-cultivation in the dark at 25° C., the explants were rinsed in liquid SIM medium (to remove excess *Agrobacterium*) (SIM, see Olhoft et al 2007 A novel *Agrobacterium rhizogenes*-mediated transformation method of soy using primary-node explants from seedlings in Vitro Cell. Dev. Biol.—Plant (2007) 43:536-549; to remove excess *Agrobacterium*) or Modwash medium (1× B5 major salts, 1× B5 minor salts, 1×MSIII iron, 3% Sucrose, 1× B5 vitamins, 30 mM MES, 350 mg/L Timentin™ pH 5.6, WO 2005/121345) and blotted dry on sterile filter paper (to prevent damage especially on the lamina) before placing on the solid SIM medium. The approximately 5 explants (Method A) or 10 to 20 (Methods B and C) explants were placed such that the target tissue was in direct contact with the medium. During the first 2 weeks, the explants could be cultured with or without selective medium. Preferably, explants were transferred onto SIM without selection for one week.

For leaf explants (Method B), the explant should be placed into the medium such that it is perpendicular to the surface of the medium with the petiole imbedded into the medium and the lamina out of the medium.

For propagated axillary meristem (Method C), the explant was placed into the medium such that it was parallel to the surface of the medium (basipetal) with the explant partially embedded into the medium.

Wrap plates with Scotch 394 venting tape (3M, St. Paul, Minn., USA) were placed in a growth chamber for two weeks with a temperature averaging 25° C. under 18 h light/6 h dark cycle at 70-100 $\mu E/m^2 s$. The explants remained on the SIM medium with or without selection until de novo shoot growth occurred at the target area (e.g., axillary meristems at the first node above the epicotyl). Transfers to fresh medium can occur during this time. Explants were transferred from the SIM with or without selection to SIM with selection after about one week. At this time, there was considerable de novo shoot development at the base of the petiole of the leaf explants in a variety of SIM (Method B), at the primary node for seedling explants (Method A), and at the axillary nodes of propagated explants (Method C).

Preferably, all shoots formed before transformation were removed up to 2 weeks after cocultivation to stimulate new growth from the meristems. This helped to reduce chimerism in the primary transformant and increase amplification of transgenic meristematic cells. During this time the explant may or may not be cut into smaller pieces (i.e. detaching the node from the explant by cutting the epicotyl).

3.5—Shoot Elongation

After 2 to 4 weeks (or until a mass of shoots was formed) on SIM medium (preferably with selection), the explants were transferred to SEM medium (shoot elongation medium, see Olhoft et al 2007 A novel *Agrobacterium rhizogenes*-mediated transformation method of soy using primary-node explants from seedlings. In Vitro Cell. Dev. Biol. Plant (2007) 43:536-549) that stimulates shoot elongation of the shoot primordia. This medium may or may not contain a selection compound.

After every 2 to 3 weeks, the explants were transferred to fresh SEM medium (preferably containing selection) after carefully removing dead tissue. The explants should hold together and not fragment into pieces and retain somewhat healthy. The explants were continued to be transferred until the explant dies or shoots elongate. Elongated shoots >3 cm were removed and placed into RM medium for about 1 week (Method A and B), or about 2 to 4 weeks depending on the cultivar (Method C) at which time roots began to form. In the case of explants with roots, they were transferred directly into soil. Rooted shoots were transferred to soil and hardened in a growth chamber for 2 to 3 weeks before transferring to the greenhouse. Regenerated plants obtained using this method were fertile and produced on average 500 seeds per plant.

After 5 days of co-cultivation with *Agrobacterium tumefaciens* transient expression of the gene of interest (GOI) was widespread on the seedling axillary meristem explants especially in the regions wounding during explant preparation (Method A). Explants were placed into shoot induction medium without selection to see how the primary-node responds to shoot induction and regeneration. Thus far, greater than 70% of the explants were formed new shoots at this region. Expression of the GOI was stable after 14 days on SIM, implying integration of the T-DNA into the soy genome. In addition, preliminary experiments resulted in the formation of cDNA expressing shoots forming after 3 weeks on SIM.

For Method C, the average regeneration time of a soy plantlet using the propagated axillary meristem protocol was 14 weeks from explant inoculation. Therefore, this method has a quick regeneration time that leads to fertile, healthy soy plants.

Example 4: Pathogen Assay 4.1. Growth of Plants

10 $T_1$ plants per event were potted and grown for 3-4 weeks in the phytochamber (16 h-day-und 8 h-night-Rhythm at a temperature of 16 and 22° C. und a humidity of 75%) till the first 2 trifoliate leaves were fully expanded.

4.2 Inoculation

The plants were inoculated with *P. pachyrhizi*.

In order to obtain appropriate spore material for the inoculation, soybean leaves which had been infected with rust 15-20 days ago, were taken 2-3 days before the inoculation and transferred to agar plates (1% agar in H2O). The leaves were placed with their upper side onto the agar, which allowed the fungus to grow through the tissue and to produce very young spores. For the inoculation solution, the spores were knocked off the leaves and were added to a Tween-H2O solution. The counting of spores was performed under a light microscope by means of a Thoma counting chamber. For the inoculation of the plants, the spore suspension was added into a compressed-air operated spray flask and applied uniformly onto the plants or the leaves until the leaf surface is well moisturized. For macroscopic assays we used a spore density of $1-5 \times 10^5$ spores/ml. For the microscopy, a density of $>5 \times 10^5$ spores/ml is used. The inoculated plants were placed for 24 hours in a greenhouse chamber with an average of 22° C. and >90% of air humidity. The following cultivation was performed in a chamber with an average of 25° C. and 70% of air humidity.

Example 5: Microscopical Screening

For the evaluation of the pathogen development, the inoculated leaves of plants were stained with aniline blue 48 hours after infection.

The aniline blue staining serves for the detection of fluorescent substances. During the defense reactions in host interactions and non-host interactions, substances such as phenols, callose or lignin accumulated or were produced and were incorporated at the cell wall either locally in papillae or in the whole cell (hypersensitive reaction, HR). Complexes were formed in association with aniline blue, which lead e.g. in the case of callose to yellow fluorescence. The leaf material was transferred to falcon tubes or dishes containing destaining solution II (ethanol/acetic acid 6/1) and was incubated in a water bath at 90° C. for 10-15 minutes. The destaining solution II was removed immediately thereafter, and the leaves were washed 2× with water. For the staining, the leaves were incubated for 1.5-2 hours in staining solution II (0.05% aniline blue=methyl blue, 0.067 M di-potassium hydrogen phosphate) and analyzed by microscopy immediately thereafter.

The different interaction types were evaluated (counted) by microscopy. An Olympus UV microscope BX61 (incident light) and a UV Longpath filter (excitation: 375/15, Beam splitter: 405 LP) are used. After aniline blue staining, the spores appeared blue under UV light. The papillae could be recognized beneath the fungal appressorium by a green/yellow staining. The hypersensitive reaction (HR) was characterized by a whole cell fluorescence.

Example 6: Evaluating the Susceptibility to Soybean Rust

The progression of the soybean rust disease was scored by the estimation of the diseased area (area which was covered by sporulating uredinia) on the backside (abaxial side) of the leaf. Additionally the yellowing of the leaf was taken into account (for scheme see FIG. 1).

At all 42 $T_1$ soybean plants (5 independent events, 8-10 plants each) expressing the RLK1 protein were inoculated with spores of *Phakopsora pachyrhizi*. The macroscopic disease symptoms caused by *P. pachyrhizi* on the inoculated soybean plants were scored 14 days after inoculation.

The average of the percentage of the leaf area showing fungal colonies or strong yellowing/browning on all leaves was considered as diseased leaf area. At all 42 soybean $T_1$ plants expressing RLK1 (expression checked by RT-PCR) were evaluated in parallel to non-transgenic control plants. Non-transgenic soy plants grown in parallel to the transgenic plants were used as control. The average of the diseased leaf area is shown in FIG. 7 for plants exogenously expressing RLK1 compared with wildtype plants. Overexpression of RLK1 reduces the diseased leaf area in comparison to non-transgenic control plants by 29.0% In average over all events generated. This data clearly indicates that the in-planta expression of the RLK1 expression vector construct lead to a lower disease scoring of transgenic plants compared to non-transgenic controls. So, the expression of RLK1 (as shown in SEQ ID NO: 1) in soybean significantly (*:p<0.05) increases the resistance of soybean against soybean rust.

The invention claimed is:

1. A method for preventing, delaying or reducing spreading of *Phakopsora* infections, the method comprising:
   growing a transgenic soybean plant in the presence of a fungal pathogen of the genus *Phakopsora*, wherein the plant comprises an exogenous nucleic acid encoding a receptor-like kinase 1 (RLK1) protein having at least 72% identity to SEQ ID NO: 2 or 10, wherein the RLK1 protein confers increased resistance against *Phakopsora* thereto in comparison to a wild type soybean plant, and wherein the exogenous nucleic acid is in functional linkage with a heterologous promoter;
   wherein spread of *Phakopsora* infection is prevented, reduced, or delayed.

2. The method of claim 1, wherein the promoter is a constitutive promoter, a pathogen-inducible promoter, a mesophyll-specific promoter or an epidermis-specific promoter.

3. The method of claim 1, wherein the exogenous nucleic acid encodes an RLK1 protein comprising an amino acid sequence having at least 80% identity to SEQ ID NO: 2 or 10.

4. The method of claim 1, wherein the exogenous nucleic acid encodes an RLK1 protein comprising an amino acid sequence having at least 90% identity to SEQ ID NO: 2 or 10.

5. The method of claim 1, wherein the exogenous nucleic acid encodes an RLK1 protein comprising an amino acid sequence having at least 95% identity to SEQ ID NO: 2 or 10.

6. The method of claim 1, wherein the exogenous nucleic acid encodes an RLK1 protein comprising an amino acid sequence having at least 98% identity to SEQ ID NO: 2 or 10.

7. The method of claim 1, wherein the exogenous nucleic acid encodes an RLK1 protein comprising an amino acid sequence having at least 99% identity to SEQ ID NO: 2 or 10.

8. The method of claim 1, wherein the exogenous nucleic acid encodes an RLK1 protein comprising an amino acid sequence having 100% identity to SEQ ID NO: 2 or 10.

* * * * *